US007943296B2

(12) United States Patent
Silberbach et al.

(10) Patent No.: US 7,943,296 B2
(45) Date of Patent: May 17, 2011

(54) METHODS OF SCREENING USING A NATRIURETIC PEPTIDE RECEPTOR

(75) Inventors: Michael Silberbach, Lake Oswego, OR (US); Charles T. Roberts, Portland, OR (US); Nathan Airhart, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 104 days.

(21) Appl. No.: 12/096,581

(22) PCT Filed: Oct. 30, 2006

(86) PCT No.: PCT/US2006/042356
§ 371 (c)(1),
(2), (4) Date: Oct. 15, 2008

(87) PCT Pub. No.: WO2007/070175
PCT Pub. Date: Jun. 21, 2007

(65) Prior Publication Data
US 2009/0312247 A1    Dec. 17, 2009

Related U.S. Application Data

(60) Provisional application No. 60/749,198, filed on Dec. 9, 2005.

(51) Int. Cl.
| | |
|---|---|
| *C07K 14/58* | (2006.01) |
| *C07K 14/475* | (2006.01) |
| *C07K 14/705* | (2006.01) |
| *C12Q 1/66* | (2006.01) |
| *C12N 5/07* | (2010.01) |
| *C12N 5/16* | (2010.01) |
| *G01N 33/53* | (2006.01) |

(52) U.S. Cl. ............. 435/4; 435/7.1; 435/7.2; 435/7.21; 435/8; 530/350; 800/3

(58) Field of Classification Search ................. None
See application file for complete search history.

(56) References Cited

U.S. PATENT DOCUMENTS
2005/0113286 A1   5/2005  Schreiner et al.
2005/0272650 A1*  12/2005 Mohapatra ...................... 514/12
2008/0214437 A1*  9/2008  Mohapatra et al. ............... 514/2

OTHER PUBLICATIONS

Potter et al. Natriuretic peptides: their stuctures, receptors, physiologic functions and therapeutic applications. Handb Exp Pharmacol 191):341-366, 2009.*
Fujio et al. Regulation of natriuretic peptide receptor A and B expression by transforming growth factor-beta1 cultured aortic smooth muscle cells. Hypertension 23: 908-913, 1994.*
Kaupp et al. Cyclic nucleotide-gated ion channels. Physiol Rev 82: 769-824, 2002.*
Matulef et al. Cyclic nucleotide-gated ion channels. Annu Rev Cell Dev Biol 19: 23-44, 2003.*
Airhart et al. Soluble natriuretic peptide receptor-related fragment (sNRF), an alternative product of the natriuretic peptide receptor gene, regulates receptor function. Circulation 114: II, 666, abstract 3152; 2006).*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Accession No. NP_000897, Oct. 18, 2005.
Airhart et al., "Atrial Natriuretic Peptide Induces Natriurectic Peptide Receptor-cGMP-Dependent Protein Kinase Interaction," *J. Biol. Chem.* 278:38693-38698, 2003.
Cogan et al., "Plasticity of Vascular Smooth Muscle α-Actin Gene Transcription," *J. Biol. Chem.* 270:11310-11321, 1995.
Crooke, "Antisense Oligonucleotides as Therapeutics for Hyperlipidaemias," *Expert Opin. Biol. Ther.* 5:907-917, 2005.
Fan et al., "Down-Regulation Does not Mediate Natriuretic Peptide-Dependent Desensitization of a Natriuretic Peptide Receptor (NPR)-A or NPR-B: Guanylyl Cyclase-Linked Natriuretic Peptide Receptors Do Not Internalize," *Mol. Pharmacol.* 67:174-183, 2005.
Gunawardena, "Multisite Protein Phosphorylation Makes a Good Threshold but can be a Poor Switch," *Proc. Natl. Acad. Sci. USA* 102:14617-14622, 2005.
Johnson et al., "Identification and Validation of the Mitochondrial $F_1F_0$-ATPase as the Molecular Target of the Immunomodulatory Benzodiazepine Bz-423," *Chem. Biol.* 12:485-496, 2005.
Mucke, "Cardiovascular and Renal Developments: Patent Highlights Jan. to Jun. 2006," *Curr. Opin. Invest. Drugs* 7:792-798, 2006.

(Continued)

*Primary Examiner* — Bridget E Bunner
(74) *Attorney, Agent, or Firm* — Klarquist Sparkman, LLP

(57) ABSTRACT

This disclosure provides an intracellular fragment of natriuretic peptide receptor A (NPRA), referred to herein as soluble natriuretic peptide receptor-related fragment (sNRF). It is shown herein that sNRF causes NP resistance. Based on these observations, methods of treating a cardiovascular disorder by inhibiting the activity of sNRF are disclosed. Assays are provided that use sNRF to screen agents for their ability to increase the biological activity of an NPR, for example agents that increase the sensitivity of NPR for NPs (such as atrial natriuretic peptide, ANP), or that decrease growth factor deleterious effects, or combinations thereof. Also provided are agents identified using the disclosed assays, and methods of using the agents, for example to treat or diagnose a cardiovascular disorder, such as heart failure.

21 Claims, 7 Drawing Sheets

OTHER PUBLICATIONS

Patel et al., "Cardiac-Specific Attenuation of a Natriuretic Peptide A Receptor Activity Accentuates Adverse Cardiac Remodeling and Mortality in Response to Pressure Overload," *Am. J. Physiol. Hear Circ. Physiol.* 289:H777-H784, 2005.

Piggott et al., "Natriuretic Peptides and Nitric Oxide Stimulate cGMP Synthesis in Different Cellular Compartments," *J. Gen. Physiol.* 128:3-14, 2006.

Potter and Hunter, "Guanylyl Cyclase-Linked Natriuretic Peptide Receptors: Structure and Regulation," *J. Biol. Chem.* 276:6057-6060, 2001.

Silberbach and Roberts, "Natriuretic Peptide Signalling Molecular and Cellular Pathways to Growth Regulation," *Cell. Signal.* 13:221-231, 2001.

Thompson and Garbers, "Dominant Negative Mutations of the Guanylyl Cyclase-A Receptor," *J. Biol. Chem.* 270:425-430, 1995.

Wang et al., "AAV Delivery of Mineralocorticoid Receptor shRNA Prevents Progression of Cold-Induced Hypertension and Attenuates Renal Damage," *Gene Ther.* 13:1097-1103, 2006.

* cited by examiner

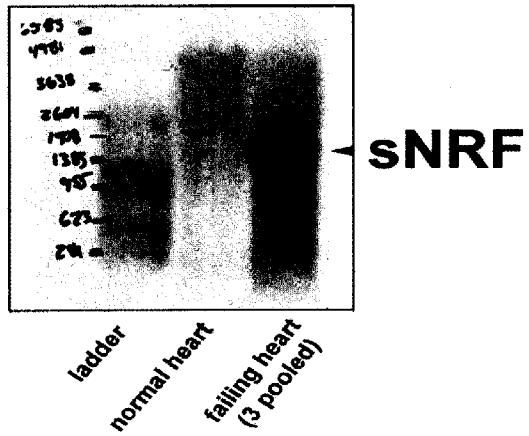
FIG. 3
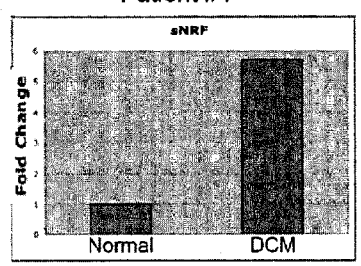
FIG. 4A
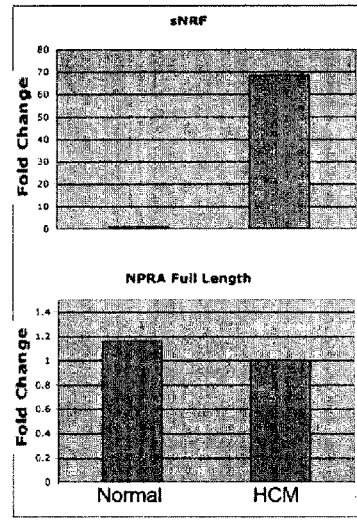
FIG. 4B
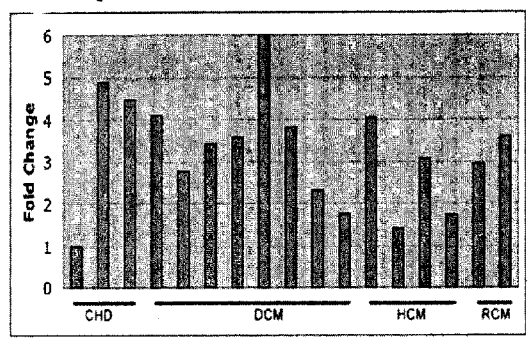
FIG. 4C
FIG. 4D

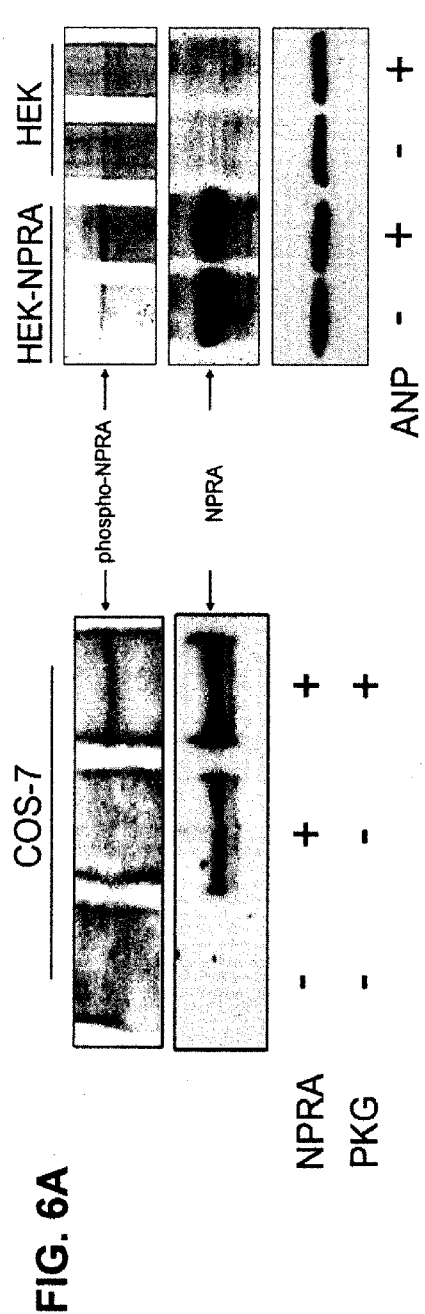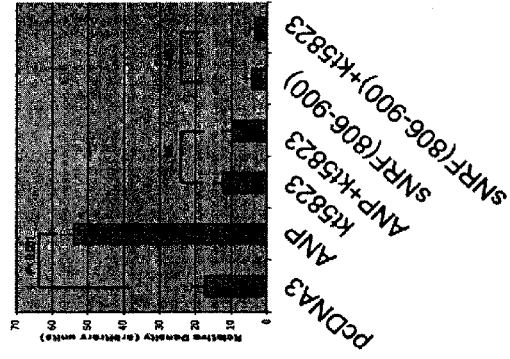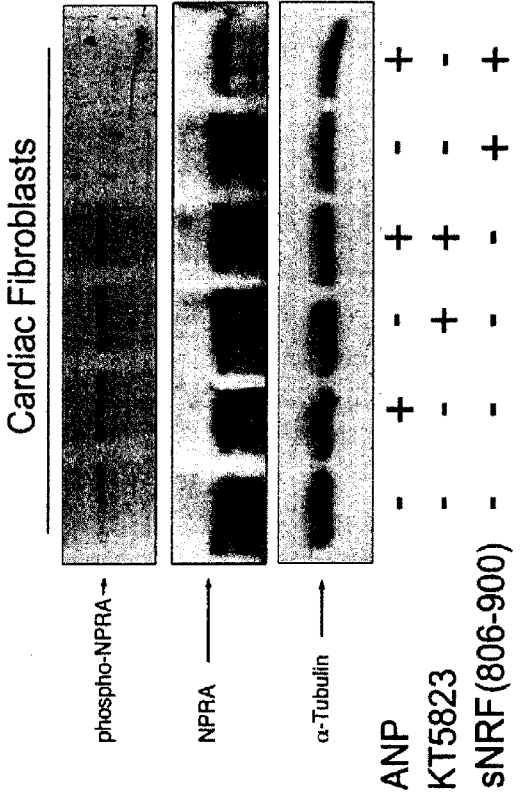

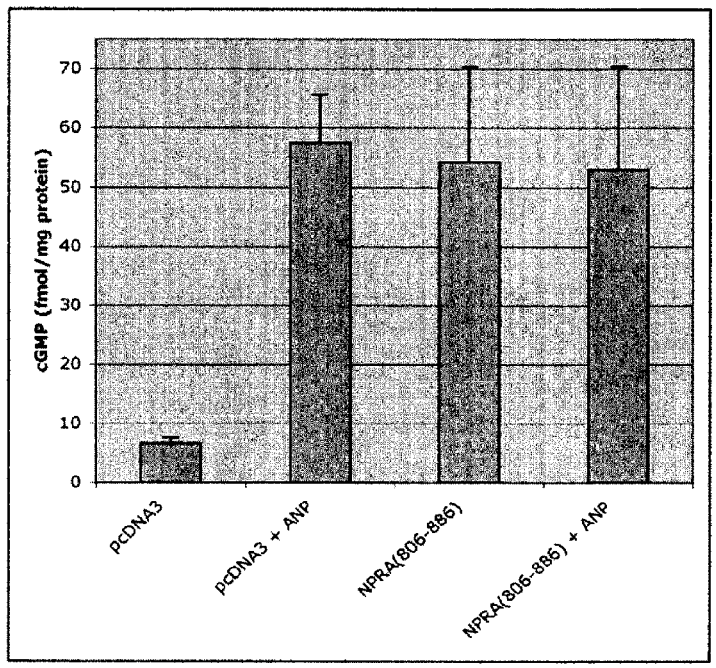
FIG. 7
FIG. 8A
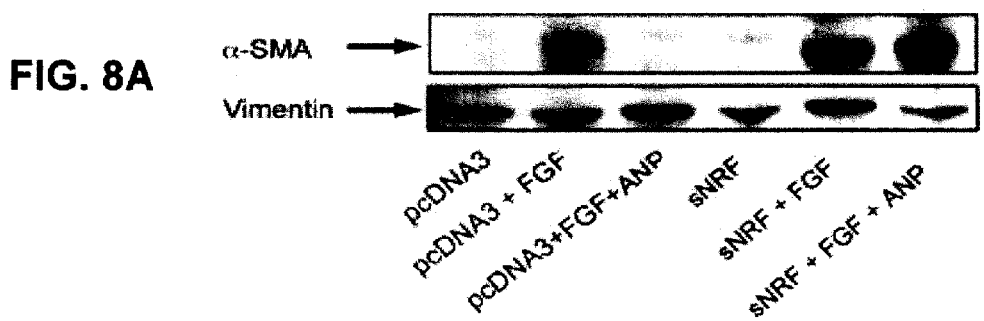
FIG. 8B
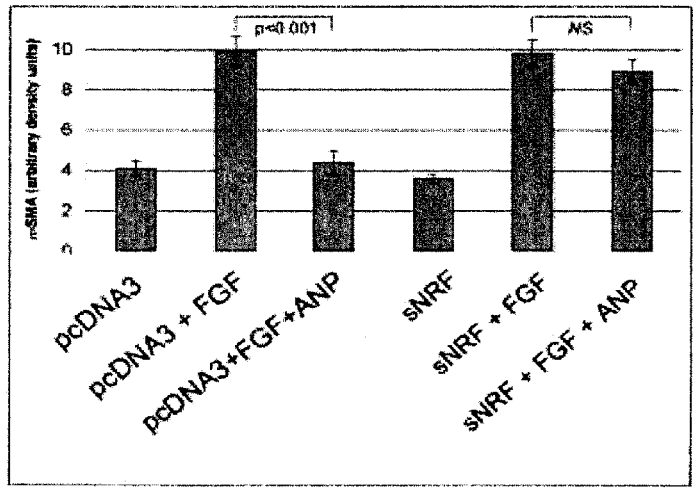

METHODS OF SCREENING USING A NATRIURETIC PEPTIDE RECEPTOR

CROSS-REFERENCE TO RELATED APPLICATIONS

This is the U.S. National Stage of International Application No. PCT/US2006/042356, filed Oct. 30, 2006, which was published in English under PCT Article 21(2), which in turn claims the benefit of U.S. Patent Application No. 60/749,198 filed Dec. 9, 2005, herein incorporated by reference.

FIELD

This application relates to methods of treating and diagnosing a cardiovascular disorder, such as heart failure, methods of identifying agents that can increase the biological activity of a natriuretic peptide receptor (such as NPRA or NPRB) or can inhibit biological activity of natriuretic peptide-related fragments (such as sNRF), agents identified using the method, and methods of using the agents to treat a cardiovascular disorder.

BACKGROUND

The proliferation and differentiation of cardiac fibroblasts (CFs) are critical for the heart's adaptation to pathological stresses (Heling et al., *Circ. Res.* 86:846-53, 2000). Specifically, CF activity immediately after myocardial infarction (Cameron et al., *Endocrinol.* 141:4690-7, 2000) and during cardiac remodeling (Katz, *J. Cell. Mol. Med.* 7:1-10, 2003; Brown et al., *Annu. Rev. Pharmacol. Toxicol.* 45:657-87, 2005) leads to myocardial fibrosis and the elaboration of collagen and extracellular matrix, the degree of which largely determines the outcome of clinical heart failure (Brown et al., *Annu. Rev. Pharmacol. Toxicol.* 45:657-87, 2005; Bax et al., *Circulation.* 110:1118-22, 2004).

Atrial (ANP) and brain (BNP) natriuretic peptide (NPs) are produced in the heart and potently inhibit CFs through their ability to bind and activate the ubiquitous NP receptor, known as natriuretic peptide receptor A or NPRA (Silberbach and Roberts, *Cell. Signal.* 13:221-31, 2001). Thus, the NP-NPRA system serves as an endogenous defense against maladaptive cardiac hypertrophy (Molkentin, *J. Clin. Invest.* 111: 1275-7, 2003; Silberbach et al., *J. Biol. Chem.* 274:24858-64, 1999). However, in the clinical setting of heart failure, receptor resistance limits these beneficial downstream effects (Fan et al., *Mol. Pharmacol.* 67:174-83, 2005; Tsutamoto et al., *Circ.* 87:70-5, 1993; Nakamura et al., *Am. Heart J.* 135:414-20, 1998; Kuhn et al., *Cardiovasc. Res.* 64:308-14, 2004). Monogenetic mouse models mimic the condition of heart failure-induced NPRA resistance, in which either cardiac-restricted NPRA deletion (Holtwick et al., *J. Clin. Invest.* 111: 1399-407, 2003) or expression of a dominant-negative NPRA mutant produces load-independent cardiac hypertrophy and fibrosis (Patel et al., *Am. J. Physiol. Heart Circ. Physiol.* 289:H777-84, 2005). However, in vivo, desensitization of the NPRA receptor is not likely due to such mutations. Therefore, models of the in vivo situation are needed, for example to identify agents that are likely to restore function to NPRA in vivo.

NPRA exists as a homodimer prior to ligand binding. Phosphorylated NPRA is active, and decreased phosphorylation causes receptor desensitization. However, a specific NPRA kinase has not been identified (Potter and Hunter, *J. Biol. Chem.* 276:6057-60, 2001). NP binding to the extracellular domain is thought to induce a conformational change in the receptor that results in the juxtaposition of the C-terminal guanylyl cyclase domains of the respective NPRA monomers, leading to the generation of 5'-cyclic-guanosine-monophosphate (cGMP). cGMP serves as a second messenger that activates cGMP-dependent protein kinase I (PKG). PKG mediates many NP downstream effects such as cardiac hypertrophy and fibrosis (Silberbach and Roberts, *Cell. Signal.* 13:221-31, 2001) and promotes cardiomyocyte survival (Kato et al., *J. Clin. Invest.* 115:2716-30, 2005).

While searching for distal PKG binding partners, an association between PKG and a C-terminal fragment of NPRA (NPRA$^{(820-1061)}$) was identified (Airhart et al., *J. Biol. Chem.* 278:38693-8, 2003). PKG I is a cytosolic serine-threonine kinase that is expressed in a variety of tissues, including the heart and peripheral vasculature. Small quantities of membrane-associated PKG I in NPRA over-expressing HEK 293 cells (HEK-NPRA cells), which increased significantly following NP treatment.

Although administration of recombinant NPs has been recently approved by the FDA, use of such compounds is limited due to NPRA resistance, which always occurs in heart failure. In addition, the use of such recombinant NPs may have deleterious long-term effects that lead to kidney failure and increased hospital mortality. Therefore, there is a need to identify additional compounds that can be used to treat cardiovascular diseases, such as heart failure.

SUMMARY

In heart failure, the beneficial effects of natriuretic peptides (NPs), including inhibition of growth factor-induced cardiac fibrosis, are blunted. Dysregulation of the NP system is, in part, due to NP receptor (NPRA) unresponsiveness. The inventors have identified an intracellular fragment of natriuretic peptide receptor A (NPRA), called soluble natriuretic peptide receptor-related fragment (sNRF), which appears to cause NP resistance. The sNRF mRNA is the result of transcription initiation in intron 15 of the NPRA gene on human chromosome 1, and encodes a cytosolic protein comprised of more than half of the intracellular portion of NPRA. It is demonstrated herein that sNRF regulates NPRA activation and inhibits NPs' ability to reverse the harmful cardiac effects of growth factors, such as fibroblast growth factor (FGF) and transforming growth factor-β1 (TGF-β1).

Based on these observations, methods of treating a cardiovascular disorder, such as heart failure, by decreasing or inhibiting the biological activity of sNRF are disclosed. In particular examples, such methods can include administration of a therapeutically effective amount of an agent that substantially decreases expression of sNRF, such as an inhibitory RNA molecule. One skilled in the art will appreciate that complete inhibition of sNRF biological activity is not required, as decreases that have beneficial effects on one or more symptoms of a cardiovascular disorder (such as heart failure) are sufficient.

Methods are disclosed for using sNRF (for example when expressed in a cardiac cell) to screen for agents that increase the biological activity of NPRA/B, decreased the deleterious cardiac effects of growth factors, or combinations thereof, for example by increasing the sensitivity of NPRA/B to NP ligand. In particular examples, the method includes contacting a cell (such as a cardiac fibroblast (CF)) with one or more test agents, a growth factor, and NP (such as ANP), and determining whether the test agent increases biological activity of NPRA/B, decreases the deleterious growth factor effects, or both. Such agents can be used to treat, such as inhibit or prevent, cardiovascular disease. In particular examples, such agents can also be used to diagnose or determine the severity of a cardiovascular disease.

The cell used in the assay, such as a CF cell, includes a molecule that can provide a signal indicating the presence or absence of NPRA/B biological activity (such as a promoter operably linked to a reporter nucleic acid sequence or a cyclic nucleotide-gated (CNG) channel), NPR (for example a native or recombinant (or both) NPRA or NPRB), and a sNRF that interferes with binding of cGMP-dependent kinase I (PKG) to NPR. In particular examples, the promoter operably linked to a reporter nucleic acid sequence is responsive to one or more growth factors whose downstream effects are modulated by NP. For example, the deleterious biological activities of a growth factor can be decreased in the presence of NP.

A high throughput approach can be used to screen molecules (such as peptides, RNAi, or other small molecules) for their ability to counteract inhibitory effect due to the presence of sNRF that interferes with binding of PKG to NPR (such as SEQ ID NO: 4, 6, 38, 40 or 42), interferes with other biological actions of sNRF (such as sNRFs ability to enhance the activity of deleterious growth factor molecules, for example TGFβ1), or combinations thereof. The molecules that are identified by such a screen are candidates for drugs that promote PKG-NPRA association and phosphorylation of NPRA and enhance the beneficial effects of the NP system, drugs that inhibit the deleterious biological activities of a growth factor, or both.

In particular examples determining whether the test agent increases biological activity of the NPRA/B or interferes with the biological activity of a growth factor includes detecting a signal (such as a fluorescent or chemiluminescent signal) generated from a protein encoded by a reporter nucleic acid sequence. Detection of an alteration in the signal compared to a reference value (such as the signal present in an absence of the test agent) indicates that the test agent increases biological activity of the NPRA/B or interferes with the biological activity of a growth factor. For example, if in the presence of the test agent the signal is significantly altered (such as decreased) relative to the signal in the absence of the test agent, this indicates that the test agent may increase biological activity of NPRA/B or interfere with the biological activity of a growth factor. In another example, determining whether the test agent increases biological activity of the NPRA/B or interferes with the biological activity of a growth factor includes detecting a signal (such as a fluorescent or chemiluminescent signal) that results from cyclic nucleotide-gate (CNG) channel activity, such as detecting the influx of calcium or manganese through the channel. Detection of an alteration in the signal compared to a reference value (such as the signal present in an absence of the test agent) indicates that the test agent increases biological activity of the NPRA/B, while detection of no significant alteration in the signal compared to a reference value (such as a change of less than 5%, such as less than 1% as compared to the signal present in an absence of the test agent) indicates that the test agent decreases deleterious growth factor effects.

Examples of types of agents that can be identified include the following. First are agents that bind to a molecule that is conformationally similar to the NPR association domain on PKG (NAD). These agents may compete with PKG binding to the expressed fragment and thereby promote PKG interaction with NPR. Some of these agents may serve to reduce or inhibit the action of an endogenous molecule (such as sNRF) that inhibits PKG-NPRA association or alters the sub-cellular location of PKG. Second are agents that bind to a PKG association domain on NPR (PAD) and thereby enhance NPR activity. In particular examples, these agents can be selected for further analysis. Third are agents that have affinity for both NAD and PAD. These agents may promote the association of NPR and PKG to a greater extent than they promote the association of sNRF and PKG. In particular examples, agents identified using the disclosed methods are selected for further analysis, for example testing in an animal model.

Agents identified as candidates to treat cardiovascular disease where PKG NPRA/B interaction is dysregulated or growth factor biological actions are enhanced can be further analyzed. For example, one or more test agents can be administered to a laboratory mammal having cardiovascular disease where NPRA/B-PKG association is dysregulated, and then determining whether the test agent treats the cardiovascular disease. Alternatively, one or more test agents can be administered to a laboratory mammal having cardiovascular disease because growth factor action is enhanced, and then determining whether the test agent treats the cardiovascular disease.

Also provided by the present disclosure are agents identified using the disclosed assays.

Methods are provided of treating a subject having cardiovascular disease (or having an increased risk of developing cardiovascular disease), for example by administration of a therapeutically effective amount of one or more therapeutic agents identified using the disclosed methods.

Also disclosed are methods of using compounds identified using the methods to diagnose cardiovascular disease in a subject. Individuals with latent or subclinical cardiovascular disease would respond to a therapeutically effective amount of one or more therapeutic agents identified using the disclosed methods. Those not responding would not have dysregulation of NPR-PKG association or do not have increased deleterious growth factor actions.

Also provided are methods of using sNRF to diagnose a cardiovascular disorder, for example to determine the severity of heart failure.

The present disclosure also provides sNRF protein and nucleic acid sequences. For example, exemplary sNRF protein sequences are shown in SEQ ID NOS: 4, 6, 8, 38, 40 and 42, and exemplary sNRF nucleic acid sequences are shown in SEQ ID NOS: 3, 5, 7, 37, 39, and 41.

The foregoing and other objects, features, and advantages of the invention will become more apparent from the following detailed description, which proceeds with reference to the accompanying figures.

BRIEF DESCRIPTION OF THE DRAWINGS

FIG. 3 is a digital image of a Northern blot containing total mRNA extracted from human heart hybridized with a probe to the 215-nt intron-15 sequence of NPRA. A prominent band can be seen at approximately 1.5 kb.

FIG. 4A is a bar graph showing the relative expression of sNRF in poly(A)$^+$ mRNA extracted from an explanted heart from a patient with dilated cardiomyopathy (DCM) compared to poly(A)+ mRNA extracted from a post-mortem specimen from a patient who died from a non-cardiac cause.

FIG. 4B is a bar graph showing that sNRF and full-length NPRA are differentially regulated in heart failure. Upper panel shows the relative expression of total sNRF mRNA extracted from the explanted heart of a patient with hypertrophic cardiomyopathy compared to "normal" heart total mRNA. Lower panel shows the relative expression of full-length mRNA using a Taqman probe targeted to exon 7 and 8 exonic sequences that are not present in the sNRF mRNA.

FIG. 4C shows the results of quantitative RT-PCR of total RNA using either a sNRF-specific or NPRA-specific probe on each of three explanted failing hearts (patients #3, 4, 5). Values represent fold change relative to the lowest value.

FIG. 4D is a bar graph showing the variable sNRF expression in childhood heart failure. Data are fold change relative to the first heart. (CHD=congenital heart disease, DCM=dilated cardiomyopathy, HCM=hypertrophic cardiomyopathy, RCM=restrictive cardiomyopathy).

FIG. 6A is a digital image of a Western blot showing that PKG phosphorylates NPRA.

FIG. 6B is a digital image of a Western blot showing NP-dependent phosphorylation of NPRA in HEK293 that overexpress NPRA. Phosphorylation is inhibited by the PKG inhibitor KT5823. No phosphorylation is observed in control cells that do not express NPRA.

FIGS. 6C and 6D are (C) a digital image of a Western blot showing in CF cells expressing endogenous NPRA, NP-dependent phosphorylation, and (D) quantification of the signals in FIG. 6C by scanning densitometry (data are the mean±SEM of 4 identical experiments). NP dependent phosphorylation is inhibited by the PKG inhibitor KT5823 and sNRF$^{(806-900)}$.

FIG. 7 is a bar graph showing that sNRF mimics NP receptor unresponsiveness observed in heart failure.

FIG. 8A is a digital image of a Western immunoblot showing that sNRF$^{(806-900)}$ reverses ANP inhibition of FGF-induced α-SMA expression. Representative Western immunoblot probed with anti-α-SMA antibody, stripped and re-probed with anti-vimentin antibody.

FIG. 8B is a bar graph showing the quantification of the signals from FIG. 8A obtained by scanning densitometry and normalized to vimentin. Data are the mean±SE of 6 identical experiments.

SEQUENCE LISTING

The nucleic and amino acid sequences listed in the accompanying sequence listing are shown using standard letter abbreviations for nucleotide bases, and three letter code for amino acids. Only one strand of each nucleic acid sequence is shown, but the complementary strand is understood as included by any reference to the displayed strand.

SEQ ID NOS: 1 and 2 show an exemplary full-length NPRA mRNA and protein sequence, respectively (GenBank Accession No. NM_000906).

SEQ ID NOS: 3-6 show exemplary intracellular NPRA fragments that can bind PKG (SEQ ID NOs: 4 and 6) and the corresponding mRNA sequences (SEQ ID NO: 3 and 5).

SEQ ID NOS: 7 and 8 show an exemplary NPRA fragment (sNRF$^{(806-860)}$, SEQ ID NO: 8) that only includes the NPRA hinge domain, and does not specifically bind PKG. The corresponding mRNA sequence is shown in SEQ ID NO: 7.

SEQ ID NOS: 9 and 10 show primers that can be used to generate a 5'-FLAG epitope-tagged sNRF$^{(806-1061)}$ fragment.

SEQ ID NOS: 9 and 11 show primers that can be used to generate a 5'-FLAG epitope-tagged sNRF$^{(806-900)}$ fragment.

SEQ ID NOS: 9 and 12 show primers that can be used to generate a 5'-FLAG epitope-tagged sNRF$^{(806-860)}$ fragment.

SEQ ID NOS: 13 and 14 show an exemplary sNRF coding sequence and the corresponding siRNA sequence, respectively, that can be used to inhibit sNRF expression.

SEQ ID NOS: 15 and 16 show an exemplary sNRF coding sequence and the corresponding siRNA sequence, respectively, that can be used to inhibit sNRF expression.

SEQ ID NOS: 17 and 18 show an exemplary sNRF coding sequence and the corresponding siRNA sequence, respectively, that can be used to inhibit sNRF expression.

SEQ ID NOS: 19 and 20 show an exemplary sNRF coding sequence and the corresponding siRNA sequence, respectively, that can be used to inhibit sNRF expression.

SEQ ID NOS: 21 and 22 show an exemplary sNRF coding sequence and the corresponding siRNA sequence, respectively, that can be used to inhibit sNRF expression.

SEQ ID NOS: 23 and 24 show an exemplary sNRF coding sequence and the corresponding siRNA sequence, respectively, that can be used to inhibit sNRF expression.

SEQ ID NOS: 25 and 26 show an exemplary sNRF coding sequence and the corresponding siRNA sequence, respectively, that can be used to inhibit sNRF expression.

SEQ ID NOS: 27 and 28 show an exemplary sNRF coding sequence and the corresponding siRNA sequence, respectively, that can be used to inhibit sNRF expression.

SEQ ID NOS: 29 and 30 show an exemplary sNRF coding sequence and the corresponding siRNA sequence, respectively, that can be used to inhibit sNRF expression.

SEQ ID NOS: 31 and 32 show an exemplary sNRF coding sequence and the corresponding siRNA sequence, respectively, that can be used to inhibit sNRF expression.

Figure 2:
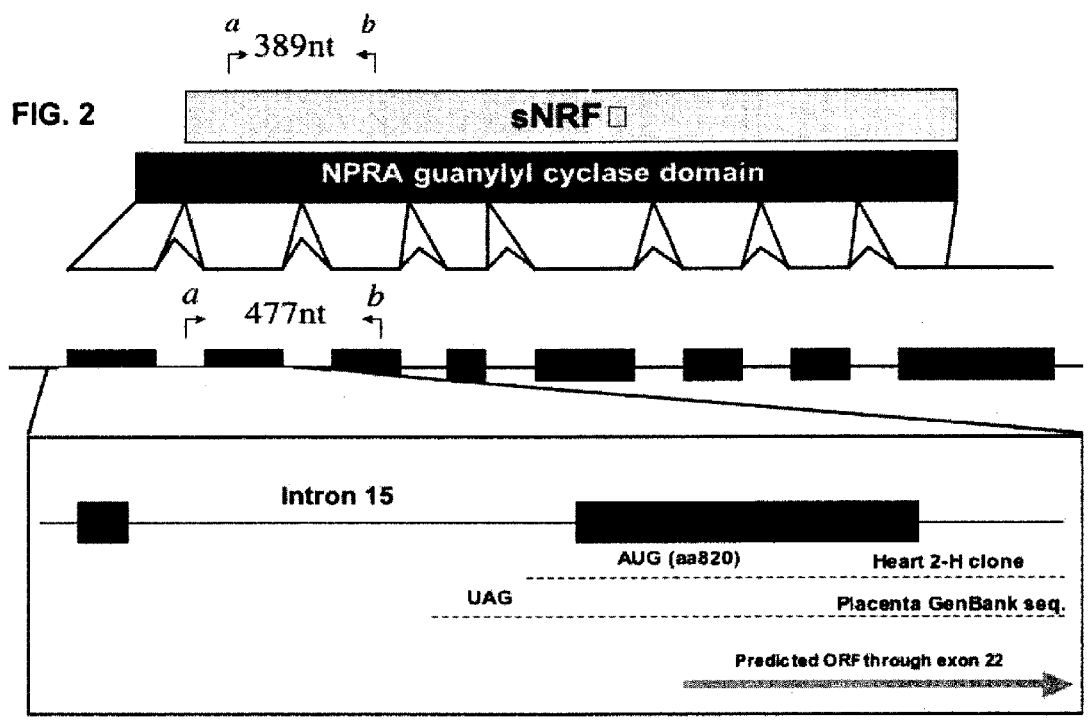
FIG. 2 is a schematic drawing showing the proposed sNRF transcription pattern. Forward primer "a" corresponds to intron 15 sequence and reverse primer "b" skips intron 16 and is complementary to exon 17 sequence. RT-PCR with primers "a" and "b" produces a 387-bp product. These primers can be employed to identify sNRF expression specifically and will not recognize NPRA because NPRA mRNA contains no intron 15 sequence.

SEQ ID NOS: 33 and 34 show forward and reverse primers, respectively, that can be used to amplify sNRF using PCR (primers "a" and "b" in FIG. 2).

SEQ ID NO: 35 shows an NPRA intron 15-specific probe that can be used for Northern blotting of RNA.

SEQ ID NO: 36 shows a TaqMan probe containing a 5' label (FAM) and a 3' label (TAMRA) that can be used to quantitate sNRF expression using real-time PCR.

SEQ ID NO: 37 shows a partial genomic sequence of an exemplary sNRF, that includes intron 15 (nucleotides 1-215) and a partial coding sequence (nucleotides 256-816).

SEQ ID NO: 38 shows the sequence encoded by SEQ ID NO: 37, and provides an exemplary sNRF protein.

SEQ ID NOS: 39-40 show an exemplary sNRF (sNRF$^{(820-1061)}$) that can bind PKG (SEQ ID NO: 40) and the corresponding cDNA sequence (SEQ ID NO: 39).

SEQ ID NOS: 41-42 show an exemplary sNRF (sNRF$^{(820-900)}$) that can bind PKG (SEQ ID NO: 42) and the corresponding cDNA sequence (SEQ ID NO: 41).

SEQ ID NOS: 43 and 44 show forward and reverse primers, respectively, that can be used to amplify sNRF using quantitative real-time PCR (primers "a" and "b" in FIG. 2).

DETAILED DESCRIPTION

Abbreviations and Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and reference to "comprising a test agent" includes reference to one or more test agents and equivalents thereof known to those skilled in the art, and so forth. The term "or" refers to a single element of stated alternative elements or a combination of two or more elements, unless the context clearly indicates otherwise. For example, the phrase "A or B" refers to A, B, or a combination of both A and B.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

ANP atrial natriuretic peptide
α-SMA alpha smooth muscle actin
CF cardiac fibroblast
CNG channel cyclic nucleotide-gated channel
NP natriuretic peptide
NPRA natriuretic peptide receptor A
NPRA/B natriuretic peptide receptor A, NPRB, or both
PKG cGMP-dependent protein kinase I
siRNA short interfering or interrupting RNA
sNRF soluble natriuretic peptide receptor-related fragment Administer: To provide or give a subject an agent, such as composition that includes the agent, by any effective route. Exemplary routes of administration include, but are not limited to, oral, injection (such as subcutaneous, intramuscular, intradermal, intraperitoneal, and intravenous), sublingual, rectal, transdermal, intranasal, and inhalation routes. In particular examples, agents (such as those identified using the disclosed methods) are administered to a subject having cardiovascular disease or having an increased risk for developing cardiovascular disease. In one example, one or more agents that substantially decrease the biological activity of sNRF (for example decrease sNRF expression), is administered to a subject having cardiovascular disease or having an increased risk for developing cardiovascular disease.

Alpha smooth muscle actin (α-SMA) promoter: A nucleic acid sequence that can promote the expression of α-SMA (an actin isoform that is a marker for myofibroblasts in the diseased heart), in vivo. In addition, an α-SMA promoter sequence can drive the expression of a nucleic acid sequence operably linked to it in the presence of a growth factor in vitro.

Includes any α-SMA promoter nucleic acid molecule from any organism, such as a mammal. This description includes α-SMA promoter variants that retain the ability to drive the expression of a nucleic acid sequence operably linked downstream of the promoter in the presence of a growth factor. For example, α-SMA promoters can promote the expression of a reporter nucleic acid sequence operably linked to the promoter, in the presence of a growth factor (such as TGF-β).

Nucleic acid α-SMA promoter sequences are publicly available. One particular example of an α-SMA promoter that can be used is disclosed in Wang et al. (*J. Clin. Invest.* 100: 1425-39, 1997) (the mouse SMC α-actin promoter fragment SMP8 (−1074 bp, 63 bp of 5'UT and 2.5 kb of intron 1).

Antisense, Sense, and Antigene: Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a particular dsDNA target (such as sNRF, for example intron 15 of NPRA). These molecules can be used to interfere with gene expression, such as expression of sNRF.

Binding: A specific interaction between two or more molecules, such that the two or more molecules interact. Therefore to "interfere with binding" refers to disrupting this interaction, for example a disruption of at least 50%, at least 75%, or at least 90%.

For example, binding can occur between a NPR and PKG, and between NPR (such as NPRA or NPRB) and a particular NP ligand, such as ANP or BNP. The binding is a non-random binding reaction, for example between two proteins. Binding can be specific and selective, so that one molecule is bound preferentially when compared to another molecule. Binding specificity of one agent for another agent is typically determined from the reference point of the ability of the agent to differentially bind a specific agent and an unrelated agent, and therefore distinguish between two different agents.

In particular examples, two compounds are said to specifically bind when the binding constant for complex formation between the components exceeds about $10^4$ L/mol, for example, exceeds about $10^6$ L/mol, exceeds about $10^8$ L/mol, or exceeds about $10^{10}$ L/mol. The binding constant for two components can be determined using methods that are well known in the art.

Cardiac fibroblast (CF): A fibroblast of the heart that can produce extracellular matrix proteins (such as collagen). CFs can be obtained from a primary culture (for example using the method of Simpson, *Circulation Res.* 56:884-94, 1985), or can be obtained from a commercial source, for example Cell Applications, Inc., San Diego, Calif. (human or rat CF cells derived from normal heart tissue).

Cardiovascular disease: Any disorder that affects the heart or the vasculature. Particular conditions include, but are not limited to: angina pectoris; arrhythmia; cardiac fibrosis; congenital cardiovascular disease; coronary artery disease (CAD); dilated cardiomyopathy; heart attack (myocardial infarction); heart failure; hypertrophic cardiomyopathy; systemic hypertension from any cause; edematous disorders caused by liver or renal disease; mitral regurgitation; myocardial tumors; myocarditis; rheumatic fever; Kawasaki disease; Takaysu arteritis; cor pulmonale; primary pulmonary hypertension; amyloidosis; hemachromatosis; toxic effects on the heart due to poisoning; Chaga's disease; heart transplantation; cardiac rejection after heart transplantation; cardiomyopathy of chachexia; arrhythmogenic right ventricular dysplasia; cardiomyopathy of pregnancy; Marfan Syndrome; Turner Syndrome; Loeys-Dietz Syndrome; familial biscuspid aortic valve or any inherited disorder of the heart or vasculature, or combinations thereof.

In some examples, cardiovascular disease is caused by a decrease in the biological activity of NPRA, for example a decrease in the sensitivity of NPRA for NP ligands such as ANP. In some examples, cardiovascular disease is caused by an increase in the biological activity of a growth factor (such as FGF or TGFβ1), for example in situations where growth factor action is enhanced by the biological activity of sNRF.

In particular examples, cardiovascular disease is treated by administration of one or more of the agents identified using the methods disclosed herein. In one example, cardiovascular disease is treated by administration of one or more agents that substantially decrease the biological activity of sNRF (for example decrease sNRF expression).

Conservative substitution: One or more amino acid substitutions (for example 1, 2, 5, 8, or 10 amino acid residues) for amino acid residues having similar biochemical properties. Typically, conservative substitutions have little to no impact on the activity of a resulting peptide. For example, a conservative substitution is an amino acid substitution in an intracellular NPRA peptide fragment, such as sNRF, that does not substantially affect the ability of the peptide to bind to PKG. In a particular example, a conservative substitution is an amino acid substitution in a sNRF, such as a conservative substitution in SEQ ID NO: 4, 6, 38, 40 or 42 that does not significantly alter the ability of the peptide to bind to NPRA or the ability of the peptide to reduce NPs' inhibitory effect on deleterious growth factor effects.

An alanine scan can be used to identify amino acid residues in a peptide (such as a sNRF, such as SEQ ID NO: 4, 6, 38, 40 or 42) that can tolerate substitution. In one example, activity is not altered by more than 25%, for example not more than 20%, for example not more than 10%, when an alanine, or other conservative amino acid (such as those listed below), is substituted for one or more native amino acids.

In a particular example, the activity of a sNRF is not substantially altered if the amount of cGMP produced by NPRA in the presence of the sNRF peptide fragment is not reduced by more than about 25%, such as not more than about 10%, than an amount of cGMP produced by NPRA in the presence of the sNRF containing one or more conservative amino acid substitutions, as compared to an amount of cGMP production in the presence of a native sNRF sequence.

A peptide can be produced to contain one or more conservative substitutions by manipulating the nucleotide sequence that encodes that peptide using, for example, standard procedures such as site-directed mutagenesis or PCR. Alternatively, a peptide can be produced to contain one or more conservative substitutions by using standard peptide synthesis methods.

Substitutional variants are those in which at least one residue in the amino acid sequence has been removed and a different residue inserted in its place. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

Decrease: To reduce the quality, amount, or strength of something.

In one example, a therapy decreases cardiovascular disease (such as cardiac fibrosis, myocyte apoptosis or expression of inflammatory cytokines), or one or more symptoms associated with cardiovascular disease (such as decreased urine output, decreased ability to exercise, dyspnea, decrease peripheral edema due to fluid retention, and all other signs or symptoms of heart failure known by skilled clinicians), for example as compared to the response in the absence of the therapy. In a particular example, a therapy decreases cardiovascular disease or a symptom of cardiovascular disease, subsequent to the therapy, such as a decrease of at least 10%, at least 20%, at least 50%, or even at least 90%. Such decreases can be measured using routine clinical methods. Examples of such therapies include administration of therapeutically effective amounts of agents identified using the methods disclosed herein or administration of therapeutically effective amounts of agents that substantially decrease the biological activity of sNRF (such as a sNRF siRNA molecule).

Decrease activity: An agent is said to "decrease activity" of a sNRF when contact of the agent results in decreased biological activity of the sNRF as compared to an amount of biological activity of sNRF not previously contacted with the agent. Decreasing the activity of a sNRF does not require complete inhibition of sNRF activity. For example, a decrease in biological activity of at least 25%, such as at least 50%, or at least 75%, when compared to no treatment with the agent indicates that the agent can decrease the biological activity of the sNRF.

In one example, decreasing the activity of sNRF increases the sensitivity of the NPRA/B receptor for NPs, such as ANP, as compared to the sensitivity in the absence of the agent that decreases the activity of sNRF. For example, this increased sensitivity can result in increased cGMP levels in response to NP treatment. In some examples, binding of NP to NPR having increased sensitivity to NP, increases at least 25% when compared to sensitivity in the absence of the agent, such as increases of at least 50%, at least 75%, at least 80%, at least 90%, at least 100%, or even at least 200%. Cyclic-GMP levels can be measured in whole cell lysates by enzyme immuno-absorbance assay (EIA) or cGMP cyclase activity assays where crude membranes are assayed in the presence of ATP and $[\alpha\text{-}^{32}P]GTP$ (for example as described in Airhart et al., *J. Biol. Chem.* 278:38693-8, 2003).

In another or in an additional example, an agent is said to decrease the activity of sNRF when contact of the agent with NPRA/B, or PKG, or both NPRA/B and PKG results in a decrease in the production of $\alpha$-SMA as measured by Western immunoblot, as compared to production in the absence of the agent, such as a decrease of at least 25% when compared to the absence of the agent, such a decrease of at least 50%, at least 60%, at least 75%, at least 80%, or at least 90%.

In another or in an additional example, an agent is said to decrease the activity of sNRF when contact of the agent with a cardiofibroblast under conditions that mimic heart failure results in a decrease in the deleterious growth factor effects (such as proliferation of the cells, and expression of collagen, extracellular matrix, and $\alpha$-SMA), as compared to production in the absence of the agent, such as a decrease of at least 25% when compared to the absence of the agent, such a decrease of at least 50%, at least 60%, at least 75%, at least 80%, or at least 90%.

In a clinical setting an agent is said to decrease the activity of sNRF when treatment of a subject with the agent results in the typical response of a patient as if sNRF expression was not increased, for example as if NPRA/B is not desensitized, if deleterious growth factor effects were not observed, or combinations thereof. Such a subject might have normalized blood pressure, increased urine output, suppression of numerous neuroendocrine markers of heart failure such as angiotensin, aldosterone, endothelin, renin, the sympathetic nervous system, or other growth factors, combing programmed cell death (apoptosis), decreased cardiac fibrosis, decrease in cardiac filling pressures, improvement of cardiac output, lessening of angina pectoris and in general diminution of the typical signs and symptoms of cardiovascular disease.

Enhance: To improve the quality, amount, or strength of something.

In one example, a therapy enhances the sensitivity of a NPRA/B to binding by NP ligands (such as ANP or BNP), if the biological activity of NPRA/B increases in the presence of NPs and the therapy, as compared to the biological activity of NPRA/B in the presence of NPs and absence of the therapy. In a particular example, a therapy enhances the sensitivity of NPRA/B to binding by NP ligands if the biological activity of NPR increases subsequent to the therapy, such as an increase of at least 10%, at least 20%, at least 50%, or even at least 90%. Such enhancement can be measured using the methods disclosed herein, for example determining an amount of cGMP using an enzyme immunoabsorbance (EIA) assay. Examples of such therapies include administration of therapeutically effective amounts of agents identified using the methods disclosed herein or administration of therapeutically effective amounts of agents that substantially decrease the biological activity of sNRF (such as a sNRF siRNA molecule).

Expression: With respect to a gene sequence, refers to transcription of the gene and, as appropriate, translation of the resulting mRNA transcript to a protein. Thus, expression of a protein coding sequence results from transcription and translation of the coding sequence.

Growth factor: Substances that responsible for regulating cell proliferation, development, migration, or differentiation. In some examples, growth factors include those whose expression is increased in response to cardiovascular disease, such as heart failure. For example, a growth factor can be one whose biological activity is modulated (such example activated or repressed) in the presence of NPs, such as ANP. In a particular example, a growth factor is one whose biological activity is decreased in the presence ANP.

Particular examples of growth factors that can be used in the screening methods provided herein include, but are not limited to, epidermal growth factor (EGF), fibroblast growth factor (FGF), erythropoietin (EPO), growth hormone (GH), insulin-like growth factor, hematopoietic cell growth factor (HCGF), platelet-derived growth factor (PDGF), vascular endothelial growth factor (VEGF), and transforming growth factors (such as TGF-β).

A deleterious growth factor affect or growth factor deleterious effects is a negative consequence to a cardiac cell (such as a cardiac fibroblast) in the presence of growth factors, such as FGF and TGFβ1. Examples of such negative consequences are those that can cause cardiovascular disease (such as heart failure), for example cellular proliferation, expression of collagen, extracellular matrix, and α-SMA, or combinations thereof. In particular examples, such negative consequences can be decreased in the presence of NP, but are negated in the presence of sNRF.

Heart failure: The condition that results when the cardiac output is insufficient to meet the metabolic needs of the body. This can occur when the heart muscles contract or relax abnormally. With heart failure, the cardiac output may be decreased and the cardiac chamber filling pressures increase. The chambers of the heart also increase in size in order to hold more blood to pump through the body. When the cardiac output decreases the kidneys often respond by causing the body to retain fluid (water) and sodium. If fluid builds up in the arms, legs, ankles, feet, lungs or other organs, the body's tissues becomes congested (edema). Therefore, heart failure can be characterized by one or more of the following symptoms: total body fluid overload, over-activation of a variety of deleterious hormones (such as catecholamines including neuroepinephine and epinephrine; vasoconstricting hormones angiotensin II and endothelin, inflammatory agents such as cytokines, fibroblast growth factor, transforming growth factor beta, and numerous others), and maladaptive thickening of the heart muscle (hypertrophy) that involves cardiac fibrosis. Causes of heart failure include, but are not limited to, coronary disease, heart attack, non-ischemic cardiomyopathy, as well as conditions that stress the heart (such as high blood pressure, valve disease, thyroid disease, kidney disease, diabetes or cardiac malformations).

Early heart failure (compensated heart failure) occurs when natriuretic peptides (NPs) and other systems effectively oppose the effects of fluid overload, hormonal activation, and maladaptive hypertrophy. Decompensated heart failure occurs when NP action is overwhelmed (in spite of the presence of high circulating NP levels), which can result in death.

In particular examples, heart failure is treated by administration of therapeutically effective amounts one or more of the agents identified using the methods disclosed herein. In some examples, heart failure is treated by administration of therapeutically effective amounts of agents that increase the activity of NPR, substantially decrease the biological activity of sNRF (such as a sNRF siRNA molecule or other chemical compounds), decrease growth factor deleterious effects, or combinations thereof.

Increase activity: An agent is said to "increase activity" of a natriuretic peptide receptor (NPR, such as NPRA/B) when contact of the agent with a desensitized or substantially inactive NPRA/B results in increased biological activity of the desensitized NPRA/B, as compared to an amount of biological activity of a desensitized NPRA/B not previously contacted with the agent. Increasing the activity of a desensitized NPRA/B does not require restoration of 100% of activity present when the receptor is sensitized. For example, an increase in biological activity of at least 25% when compared to no treatment with the agent indicates that the agent can increase the biological activity of the desensitized NPRA/B.

In one example, increasing the activity of NPRA/B (such as desensitized NPRA/B) increases the sensitivity of the receptor for NPs, such as ANP, as compared to the sensitivity in the absence of the agent. For example, this increased sensitivity can result in increased cGMP levels in response to NP treatment. In some examples, binding of NP to NPR having increased sensitivity to NP, increases at least 25% when compared to sensitivity in the absence of the agent, such as increases of at least 50%, at least 75%, at least 80%, at least 90%, at least 100%, or even at least 200%. Cyclic-GMP levels can be measured in whole cell lysates by enzyme immunoabsorbance assay (EIA) or cGMP cyclase activity assays where crude membranes are assayed in the presence of ATP and [α-$^{32}$P]GTP (for example as described in Airhart et al., *J. Biol. Chem.* 278:38693-8, 2003).

In another or in an additional example, an agent is said to increase the activity of NPRA/B (such as desensitized NPRA/B) when contact of the agent with NPRA/B, or PKG, or both NPRA/B and PKG results in a decrease in the production of α-SMA as measured by Western immunoblot, as compared to production in the absence of the agent. For example, production of an intracellular marker of NPRA/B function (such as cGMP or α-SMA) by an NPRA/B having increased biological activity, can increase or decrease by at least 25% when compared to production of an intracellular marker of NPRA/B function in the absence of the agent, such as changes of at least 50%, at least 60%, at least 75%, at least 80%, or at least 90%. Determining an amount of production of an intracellular marker of NPRA/B function can be performed using the methods disclosed herein.

In a clinical setting an agent is said to increase the activity of NPRA/B (such as desensitized NPRA/B) when treatment of a subject with the agent results in the typical response of a patient as if the NPRA/B is not desensitized. Such a subject might have normalized blood pressure, increased urine output, suppression of numerous neuroendocrine markers of heart failure such as angiotensin, aldosterone, endothelin, renin, the sympathetic nervous system, or other growth factors, combing programmed cell death (apoptosis), decreased cardiac fibrosis, decrease in cardiac filling pressures, improvement of cardiac output, lessening of angina pectoris and in general diminution of the typical signs and symptoms of cardiovascular disease.

Mammal: Includes both human and non-human mammals. Similarly, the terms "patient," "subject," and "individual" includes living multicellular vertebrate organisms, such as human and veterinary subjects.

MicroRNA (miR): A small non coding RNA sequence that directs post transcriptional regulation of gene expression through interaction with a homologous mRNA. MiRs can inhibit translation, or can direct cleavage of target mRNAs. Therefore, miRs can be used to decrease or inhibit expression of sNRF, for example to treat heart failure. In particular examples, miRs are about 21-26 nucleotides in length.

Natriuretic peptide (NP): A family of peptide hormones that regulate mammalian blood volume and blood pressure, and which are natural antagonists to the renin-angiotensin-aldosterone system. Members include atrial (ANP), brain (BNP), and C-type (CNP) natriuretic peptides. ANP and BNP are released primarily from the heart, while CNP is released primarily from noncardiac tissues (such as the endothelium).

ANP is a 28 amino acid peptide (for example see amino acids 124 to 151 of GenBank Accession No. AAA35529) that is synthesized, stored, and released by atrial myocytes in response to atrial distension, angiotensin II stimulation, endothelin, and sympathetic stimulation (beta-adrenoceptor mediated). Therefore, elevated levels of ANP are found during hypervolemic states (elevated blood volume) and congestive heart failure.

Natriuretic peptide receptor (NPR): A family of receptors that specifically bind to NPs. Natriuretic peptide receptor A (NPRA) and B (NPRB) are members of the transmembrane guanylyl cyclase family that mediate the effects of natriuretic peptides via the second messenger cyclic GMP (cGMP). ANP and BNP are extracellular ligands for NPRA, while CNP is an extracellular ligand for NPRB. When ANP, BNP or CNP bind to NPRA or NPRB, an increase in guanylate cyclase activity results leading to production of cGMP. NPRC is not linked to guanylyl cyclase and serves as a clearance receptor.

The NPRA and NPRB receptors (NPRA/B) are composed of an extracellular ligand binding, transmembrane, protein kinase-like, hinge, and catalytic domains. The location of such domains is publicly available. For example, NPRA and NPRB have an about 450 amino acid extracellular ligand binding domain, a 21 amino acid hydrophobic membrane-spanning region, and about 566-568 intracellular amino acids (which can be divided into a juxtamembrane region of about 250 amino acids (kinase homology domain), a 41 amino acid hinge region, and an about 250 amino acid guanylyl cyclase catalytic domain). In a particular example, in human NPRA, the extracellular ligand binding domain includes amino acids 54-415, the transmembrane domain includes amino acids 477-493, the protein kinase-like domain includes amino acids 547-804, hinge domain includes amino acids 805-848, and the catalytic domain includes amino acids 840-1023 (amino acids refer to SEQ ID NO: 2).

NPRs are present in most tissues of the body including cardio-myocytes and fibroblasts. Binding of NP ligands (such as ANP and BNP) to NPRs (such as NPRA) in cells of the heart reduce or inhibit the biological activity of growth factors that are present during heart failure (such as FGF, EGF, and TGF-$\beta$). Therefore, the biological activity of NPR provides a cardioprotective function, by limiting the hypertrophic and fibrotic response to pressure overload, suppressing the neuroendocrine mileu of heart failure, inhibiting programmed cell death (apoptosis) in cardiomyocytes thus potentially reducing mortality. In particular examples, such activity is achieved upon binding of NPs to the extracellular domain of NPR.

In living subjects NPRA/B function can assessed by measuring the circulating levels or urinary levels of cGMP in response to NP infusion. A typical bioassay of NPR function is to measure changes in forearm vascular resistance in response to NP infusion. Other common bioassays can be the urine output response to NP infusion. In the hospital setting favorable changes in cardiac filling pressure, decrease in the pain associated with angina pectoris and improved sense of well-being can be measured.

NPRA and NPRB protein and nucleic acid sequences are publicly available, for example from EMBL or GenBank. For example, GenBank Accession Nos. AAH63304 and AAA66945 provide human and mouse NPRA protein sequences, respectively. GenBank Accession Nos. BC063304 and L31932 provides human and mouse NPRA nucleic acid sequences, respectively. One particular example of a full-length NPRA protein sequence is shown in SEQ ID NO: 2.

Nucleic acid molecule: Encompasses both RNA and DNA including, without limitation, cDNA, genomic DNA, mRNA. Includes synthetic nucleic acid molecules, such as those that are chemically synthesized or recombinantly produced. The nucleic acid molecule can be double-stranded or single-stranded. Where single-stranded, the nucleic acid molecule can be the sense strand or the antisense strand. In addition, nucleic acid molecules can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a reporter sequence). Generally, operably linked DNA sequences are contiguous and, where necessary to join two protein coding regions, in the same reading frame.

Peripheral administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Pharmaceutical agent or drug: A chemical compound or composition capable of inducing a desired therapeutic effect when administered to a subject, alone or in combination with another therapeutic agent(s) or pharmaceutically acceptable carriers. In a particular example, a pharmaceutical agent treats heart failure, for example by reducing one or more signs or symptoms of heart failure.

Promoter: An array of nucleic acid control sequences that direct transcription of a nucleic acid molecule, such as a reporter sequence. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

The term includes endogenous promoter sequences as well as exogenous promoter sequences. In one example, the promoter is an inducible promoter, such as a promoter responsive to a particular stimulus. In a particular example, the inducible promoter is one that is responsive to the presence of a growth factor that is responsive to NPs, such as epidermal growth factor (EGF), fibroblast growth factor (FGF), or TGF-β1. Particular examples of promoters that are responsive to a growth factor that is responsive to NPs include, but are not limited to: alpha smooth muscle actin promoter (α-SMA), pro alpha 2(I) collagen promoter, β-myosin heavy chain promoter, or an atrial natriuretic peptide promoter.

Recombinant: A recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid molecule was isolated.

Reporter: A molecule that produces a detectable signal when a target molecule present. In particular examples, a detectable molecule produces a calorimetric signal, for example a luminescent or fluorescent signal. Methods of detecting such signals are known in the art, and can include, but are not limited to, ELISA, spectrophotometry, flow cytometry, or microscopy.

In particular examples, a reporter is a nucleic acid sequence that produces a detectable protein when expressed. A reporter nucleic acid molecule can include a promoter, the structural sequence of the reporter gene, and the sequences required for the formation of functional mRNA. Upon introduction of the reporter construct into cells, expression levels of the reporter gene can be monitored, for example by assaying for the reporter protein's enzymatic activity, or by measuring production of the protein directly (for example if the protein is a fluorescent or luminescent protein, such as green fluorescent protein (GFP), fluorescence or luminescence can be detected). Particular examples include, but are not limited to: luciferase, β-galactosidase, chloramphenicol acetyltransferase (CAT), GFP (or variants thereof such as E-GFP). Sequences for such reporter molecules are well-known in the art. For example, a promoter (such as one that is responsive to growth factors that are modulated by NPs) can be inserted into these plasmids that include the indicated reporter: p-lacZ (beta-galactosidase reporter), p-luc (firefly luciferase reporter) and p-cat (chloramphenicol acetyl transferase).

In other particular examples, a reporter is molecule that can detect the presence of another molecule, such the ability of fura-2 to detect the presence of $Ca^{2+}$ or $Mn^{2+}$ influx through a CNG channel. For example, ANP can increase cGMP levels, thereby activating CNG channels, as detected by the presence $Ca^{2+}$ or $Mn^{2+}$ by measuring fura-2 levels.

RNA interference (RNAi): A post-transcriptional gene silencing mechanism mediated by double-stranded RNA (dsRNA). Introduction of dsRNA into cells, such as siRNA compounds, induces targeted degradation of RNA molecules with homologous sequences. RNAi compounds can be used to modulate transcription, for example, by silencing genes, such as sNRF (for example by targeting nucleotides 1-215 of SEQ ID NO: 37). In certain examples, an RNAi molecule is directed against a target, such as sNRF, and is used to treat heart failure.

Short interfering or interrupting RNA (siRNA): Double-stranded RNAs that can induce sequence-specific post-transcriptional gene silencing, thereby decreasing or even inhibiting gene expression. In some examples, siRNA molecules are about 19-23 nucleotides (nt) in length, such as 21-23 nt. In particular examples, siRNA molecules are at least 21 nt, for example at least 23 nt in length. In one example, an siRNA molecule is an siRNA duplex composed of 21-nt sense and 21-nt antisense strands, paired in a manner to have a 2-nt 3' overhang on both strands. In another example, an siRNA is 19 nt in length having two dT overhangs at the N- and C-terminal ends. In a particular example, an siRNA molecule selectively binds to intron 15 of NPRA, thereby decreasing expression of sNRF.

In one example, siRNA triggers the specific degradation of homologous RNA molecules, such as mRNAs, within the region of sequence identity between both the siRNA and the target RNA (such as sNRF RNA). For example, WO 02/44321 discloses siRNAs capable of sequence-specific degradation of target mRNAs when base-paired with 3' overhanging ends. The direction of dsRNA processing determines whether a sense or an antisense target RNA can be cleaved by the produced siRNA endonuclease complex. Thus, siRNAs can be used to modulate transcription, for example, by silencing genes, such as sNRF, for example to treat heart failure. Particular exemplary siRNA molecules that can be used to silence sNRF expression include those shown in SEQ ID NOS: 14, 16, 18, 20, 22, 24, 26, 28, 30, and 32.

Signal: A detectable change in a physical quantity or impulse that provides information. In the context of the disclosed methods, examples include light, such as light of a particular quantity or wavelength. In certain examples the signal is the disappearance of a physical event, such as quenching of light.

sNRF (soluble natriuretic peptide receptor-related fragment): An intracellular fragment of NPRA that interferes with binding of cGMP-dependent kinase I (PKG) to NPR. In some examples, sNRF does not include a kinase homology domain. In some examples, sNRF does not include a hinge domain.

In particular examples, a sNRF protein includes a sequence of at least 60 contiguous amino acids from the intracellular region of NPRA, for example at least 70 contiguous amino acids, at least 80 contiguous amino acids, or at least 90 contiguous amino acids from the intracellular region of NPRA (such as at least 60, at least 70, at least 80, or at least 90 contiguous amino acids of residues 806 to 1061 of SEQ ID NO: 2 or residues 820-1061 of SEQ ID NO: 2). Particular examples include, but are not limited to, the sequences provided in SEQ ID NOS: 4, 6, 38, 40 and 42, as well as variants thereof that retain the biological activity of these fragments.

Subject: Living multicellular vertebrate organisms. Includes human and veterinary subjects, such as dogs, cats, cows, horses, sheep, rodents, and birds.

Test agent: Any peptide, organic compound, inorganic compound, nucleic acid molecule (such as an RNAi) or other molecule of interest. In particular examples, a test agent can permeate a cell membrane (alone or in the presence of a carrier). In particular examples, a test agent is one whose ability to treat one or more symptoms of heart failure is desired to be determined, for example its ability to decrease the biological activity of sNRF.

Therapeutically effective amount: An amount of an agent (alone or in combination with other therapeutically effective agents) sufficient to achieve a desired biological effect. In one example, it is an amount that is effective to increase the activity of a NPRA/B, such as a desensitized NRPA receptor. In one example, it is an amount that is effective to decrease the deleterious growth factor effects. In particular examples, increasing the activity of NPRA/B or decreasing deleterious growth factor effects alters the production of an intracellular marker of NPRA/B function (such as cGMP or α-SMA), increases the sensitivity of NPR for NP ligands, such as in a CF cell of a subject to whom it is administered. In a particular example, the activity of NPRA/B is increased or the deleterious growth factor effects decreased (or both) by decreasing the activity of sNRF, for example by decreasing expression of sNRF.

In a particular example, it is an amount of an agent effective to increase the activity of NPRA/B by at least 25%, at least 50%, at least 75%, or at least 90%, for example as compared to an amount of activity prior to treatment. In other or additional examples, it is an amount effective to increase production of an intracellular marker of NPRA/B function, such as increase in production of α-SMA by at least 25%, at least 50%, at least 75%, or even at least 90% as compared to an amount of production prior to treatment. In other or additional examples, it is an amount effective to decrease production of an intracellular marker of NPRA/B function, such as a decrease in production of cGMP by at least 25%, at least 50%, at least 75%, or even at least 90% as compared to an amount of production prior to treatment. In other or additional examples, it is an amount effective to increase the sensitivity of NPRA/B for NP ligands by at least 25%, at least 50%, at least 75%, or at least 90% as compared to an amount of sensitivity of NPRA/B for NP ligands prior to treatment. In some examples, it is an amount of an agent effective to decrease deleterious growth factor effects by at least 25%, at least 50%, at least 75%, or at least 90%, for example as compared to an amount of activity prior to treatment. In other or additional examples, it is an amount effective to decrease the biological activity of sNRF, such as the detectable expression of sNRF, by at least 25%, at least 50%, at least 75%, or at least 90% as compared to an amount of activity prior to treatment.

In some examples, it is an amount of a therapeutic agent (alone or in combination with other therapeutically effective agents) that can increase the activity of NPRA/B, decrease deleterious growth factor effects, decrease the activity of sNRF, or combinations thereof, to improve signs or symptoms of a disease caused by decreased NPRA/B activity. In particular examples a therapeutically effective amount improves one or more signs or symptoms of cardiovascular disease, for example such a condition associated with desensitized NPRA/B or increased growth factor activity, such as heart failure.

An effective amount of an agent that increases the activity of NPRA/B, decrease deleterious growth factor effects, decrease the activity of sNRF, or combinations thereof, can be administered in a single dose, or in several doses (for example daily, weekly, or monthly) during a course of treatment. However, the effective amount of agent may be dependent on the source of agent administered, the subject being treated, the severity and type of disease being treated, and the manner of administration. For example, a therapeutically effective amount of a therapeutic agent disclosed herein (such as one that increases the activity of NPRA/B or decreases deleterious growth factor effects) can vary from about 1 μg/kg body weight to about 20 μg/kg body weight per dose, about 1 μg/kg body weight to about 10 μg/kg body weight per-dose, about 10 μg/kg body weight to about 20 μg/kg body weight per dose, or about 1-2 μg agent/kg body weight/dose. In another example, a therapeutically effective amount of an RNAi nucleic acid molecule (such as an siRNA, antisense, or miR) that decreases the activity of sNRF can vary from about 1 mg/kg body weight to about 100 mg/kg body weight per dose, about 1 mg/kg body weight to about 10 mg/kg body weight per dose, about 10 mg/kg body weight to about 20 mg/kg body weight per dose, or about 1-2 mg/kg body weight/dose.

To assess restoration or increased NPRA/B activity, decreased deleterious growth factor effects, or combinations thereof, (for example to assess decreased sNRF biological activity), the methods disclosed herein can be used to compare a subject before and after treatment. For example, expression of intracellular markers of NPRA/B function, sensitivity of NPRA/B to NP ligands, and the effect on signs and symptoms of cardiovascular disease can be determined using the methods described below. Similarly, the methods disclosed herein can be used to compare a subject before and after treatment.

Transduce, Transform, or Transfect: To introduce a nucleic acid molecule into a cell, such as an siRNA or other inhibitor nucleic molecule specific for sNRF. These terms encompass all techniques, by which a nucleic acid molecule can be introduced into a cell, including but not limited to, transfection with viral vectors, transformation with plasmid vectors, and introduction of naked DNA by electroporation, lipofection, and particle gun acceleration. A transfected or transformed cell is a cell into which has been introduced a nucleic acid molecule by molecular biology techniques, such as a transformed CF that includes a recombinant promoter operably linked to a reporter nucleic acid molecule. In particular examples the nucleic acid molecule becomes stably replicated by the cell, for example by incorporation of the nucleic acid molecule into the cellular genome, or by episomal replication.

Treating a disease: "Treatment" refers to a therapeutic intervention that ameliorates a sign or symptom of a disease or pathological condition, such a sign or symptom of cardiovascular disease. Treatment can also induce remission or cure of a condition, such as a cardiovascular disease. In particular examples, treatment includes preventing a disease, for example by inhibiting the full development of a disease, such as preventing development of cardiovascular disease (for example heart failure). Prevention of a disease does not require a total absence of cardiovascular disease. For example, a decrease of at least 10%, at least 25% or at least 50% can be sufficient.

Under conditions sufficient for: A phrase that is used to describe any environment that permits the desired activity.

In one example, includes culturing cells (such as CFs) sufficient to allow the desired activity. In particular examples, the desired activity is increasing the biological activity of NPRA/B in the cell, decreasing the deleterious growth factor action on cardiovascular disease, or combinations thereof.

In another example, includes administering an agent (such as one identified using the disclosed methods) to a subject sufficient to allow the desired activity. In particular examples, the desired activity is increasing the biological activity of NPRA in a cell (such as a CF), decreasing the deleterious growth factor action in a cell (such as a CF), or combinations thereof.

Unit dose: A physically discrete unit containing a predetermined quantity of an active material (such as a therapeutic agent identified using the disclosed methods) calculated to individually or collectively produce a desired effect. A single unit dose or a plurality of unit doses can be used to provide the desired effect, such as treatment of heart failure.

Variant sequence: A native sequence, such as a native sNRF sequence, that is modified at one or more nucleotides or one or more amino acids. Exemplary variants include mutants (such as sequences that include one or more nucleotide or amino acid substitutions, deletions, insertions, or combinations thereof), fragments (such as a fragment that retains the biological activity of the native protein), fusions (for example fusion to a sequence that permits purification of a protein, such as a His-tag), or combinations thereof. Ideally, variant sequences retain the biological activity of the native sequence (for example the same ability to disrupt PKG-NPRA association as the native sequence).

Vector: A nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the art. In a particular example, a vector includes a promoter operably linked upstream from a reporter nucleic acid sequence.

The pleiotrophic beneficial effects of natriuretic peptides (NPs), including diuresis, vasodilation, promotion of cardiomyocyte survival, inhibition of cardiac hypertrophy, inhibition of cardiac fibroblast proliferation, inhibition of smooth muscle proliferation, inhibition of the sympathetic nervous system, and inhibition of aldosterone synthesis, has fostered enthusiasm for the use of synthetic human NPs as a heart failure therapy. However, in heart failure, the beneficial effects of NPs, including inhibition of growth factor-induced cardiac fibrosis, are blunted. Heart failure itself was initially postulated to be an NP-deficient state. Later, when massively high circulating NP levels were observed in heart failure patients, it became evident that the heart, vasculature, and kidneys were, in fact, NP-resistant. The mechanism of NP resistance in heart failure is currently unknown.

It is shown herein that a soluble, C-terminal fragment of the NPRA gene (named soluble natriuretic peptide receptor-related fragment, or sNRF) likely causes NP resistance. The sNRF mRNA is the result of transcription initiation in intron 15 of the NPRA gene on human chromosome 1, and encodes a cytosolic protein comprised of more than half of the intracellular portion of NPRA.

It is shown herein that cGMP-dependent protein kinase I (PKG) associates with NPRA and phosphorylates it in a ligand-dependent fashion. The association between PKG and NPRA is involved in the ligand-dependent receptor guanylyl cyclase activation, as well as NPRA's ability to reduce or inhibit growth factor-induced CF differentiation. The interaction of PKG and NPRA can be disrupted in the presence of sNRF, indicating that the PKG-NPRA association is a component of NPRA activation and that the failure or reduction of PKG-NPRA association is involved in the desensitization of NPRA in a variety of cardiac diseases. When the interaction between PKG and NPR is disrupted, NPR becomes insensitive to the presence of NP ligand, thus decreasing the activity of NPR.

sNRF regulates NPRA activation and inhibits NPs' ability to reverse the harmful cardiac effects of FGF and transforming growth factor-$\beta_1$ (TGF-$\beta_1$). sNRF appears to amplify TGF-$\beta_1$ effects that, in turn, may promote heart failure. Thus, sNRF expression mimics the hormonal milieu of heart failure produced by NPRA knockout, and it is proposed that sNRF plays a role in the progression of heart failure. The observations presented herein indicate that dysregulation of PKG-NPRA association and the resulting inhibition of NPRA phosphorylation may be the mechanism of clinical NPRA resistance. Without wishing to be bound to a particular theory, it is proposed that in the presence of sNRF (which interferes with the PKG-NPRA association), PKG can no longer interact with or phosphorylate NPRA. As a result, the presence of NP has no effect on the NPR. Alternatively sNRF may act by potentiating the deleterious effect of a growth factor, for example a TGFβ1 effect on cardiovascular diseases, independently of sNRF effects on NPR.

Based on these observations, methods of treating heart failure by administration of agents that interfere with sNRF biological activity (such as RNAi molecules specific for sNRF), agents that increase the biological activity of NPR (such as NPRA), agents that inhibit the potentiation of growth factor deleterious effects, or combinations thereof. Also provided are methods of screening for agents that increase the biological activity of NPR, agents that inhibit the potentiation of growth factor deleterious effects, or both, such as sNRF-inhibiting small molecules. In particular examples, such agents can treat heart failure by restoring or enhancing the beneficial effects of the NP system or inhibiting the deleterious effects of growth factors. Such agents may increase the affinity of PKG for NPRA or NPRB (referred to herein as NPRA/B). In particular examples, these agents may activate NPRA/B independently of ligand, re-sensitize the receptor to ligand action, decrease the biological effects of sNRF, decrease the deleterious effects of growth factors, or combinations thereof. It is also possible to treat heart failure by inhibiting interference of the NPRA interference with PKG-NPRA association, for example by administering an inhibitor of sNRF. Similarly, it is possible to provide models of heart failure in an animal by administering agents (such as sNRF) that interfere with PKG-NPRA association, agents that increase harmful growth factor actions, or combinations thereof.

Methods of Treating Cardiovascular Disease

Based on the results herein, it is proposed that prolonged NP exposure increases sNRF expression, and that decreasing the biological activity of sNRF (or increasing the biological activity of NPRA or NPRB, for example by increasing the sensitivity of NPRA for ANP) will rescue NP responsiveness in human CFs. The present disclosure provides methods of treating cardiovascular disease, for example by restoring NPs' beneficial effects in NP-resistant cells. In some examples, the cardiovascular disease to be treated results from a ligand-induced desensitization of NPRA, results from other ill-effects of increased sNRF expression (such as the harmful effects of growth factor action that are potentiated by sNRF expression), or combinations thereof. In particular examples, the method includes inhibiting or decreasing the biological activity of sNRF (such as its ability to desensitize NPRA), increasing the biological activity of NPR (such as its sensitivity to NP), decreasing or inhibiting growth factor effects that are increased by sNRF, or combinations thereof.

Particular cardiovascular diseases that can be treated using the disclosed methods include, but are not limited to: angina pectoris; arrhythmia; cardiac fibrosis, congenital cardiac malformations; coronary artery disease (CAD); dilated cardiomyopathy; heart attack (myocardial infarction); heart failure; hypertrophic cardiomyopathy; systemic hypertension from any cause, edematous disorders caused by liver or renal disease, mitral regurgitation, myocardial tumors, myocarditis, rheumatic fever, Kawasaki disease, Takaysu arteritis, cor pulmonale, primary pulmonary hypertension, amyloidosis, hemachromatosis, toxic effects on the heart due to poisoning, Chaga's disease, heart transplantation, cardiac rejection after heart transplantation, cardiomyopathy of chachexia, arrhythmogenic right ventricular dysplasia, cardiomyopathy of pregnancy, or cardiovascular manifestations of Marfan Syndrome; Turner Syndrome; Loeys-Dietz Syndrome, familial biscuspid aortic valve, or any inherited disorder of the heart or vasculature, or combinations thereof.

Inhibiting sNRF

Methods of inhibiting the biological activity of a nucleic acid or protein sequence are known in the art. Although particular examples of such methods are provided herein for illustrative purposes, the disclosure is not limited to such methods. In particular examples, inhibiting the biological activity of sNRF does not require a 100% reduction. For example, decreases of at least 20%, at least 40%, at least 50%, at least 60%, at least 75%, at least 80%, at least 90%, at least 95%, or at least 99%, as compared to a control (such as an amount of activity in a cell not treated with a therapeutic agent), can be sufficient.

One particular method that can be used to decrease the biological activity of a sNRF nucleic acid or protein sequence is to decrease or disrupt transcription or translation of an mRNA encoding sNRF in the cell. Decreased expression of sNRF will result in a decreased amount of sNRF available for desensitizing NPR.

Based on the disclosed sNRF nucleic acid sequences (for example see SEQ ID NOS: 3, 5, 7, 37, 39, and 41), including variants, fusions and fragments of such sequences, methods that can be used to interrupt or alter transcription of such nucleic acid molecules include, but are not limited to, site-directed mutagenesis (including mutations caused by a transposon or an insertional vector), providing a DNA-binding protein that binds to the coding region of the protein (thus blocking or interfering with RNA polymerase or another protein involved in transcription), disrupting expression of sNRF coding sequence (for example by functionally deleting the coding sequence, such as by a mutation, insertion, or deletion), altering the amino acid sequence or overall shape of sNRF protein, degrading sNRF protein, or combinations thereof.

Various inactive and recombinant DNA-binding proteins, and their effects on transcription, are discussed in Lewin, *Genes VII*. Methods that can be used to interrupt or alter translation of a nucleic acid molecule include, but are not limited to, using an antisense RNA, ribozyme or an siRNA that binds to a messenger RNA transcribed by the nucleic acid encoding sNRF. Such methods can be used to decrease or inhibit expression of sNRF, to treat heart failure.

For example, the amount mRNA can be decreased in the cell by contacting the mRNA with a therapeutically effective amount of a molecule that binds to sNRF messenger RNA, for example molecules that are complementary to intron 15 of NPRA (nucleotides 1-215 of SEQ ID NO: 37). Examples of such complementary molecules include antisense RNA, ribozyme, triple helix molecule, miR, or siRNA that is specific for the mRNA, for example by administering to the cell the antisense RNA, ribozyme, triple helix molecule, miR, or siRNA. In one example, antisense RNA, triple helix molecule, ribozyme, miR, or siRNA molecules are contacted with the cell under conditions that permit the molecule to be introduced into the cell. In a particular example, an expression vector that transcribes one or more antisense RNA, ribozyme, triple helix molecule, miR, or siRNA sequences that recognize a sNRF mRNA sequence is used to transform cells.

Particular siRNA, antisense, and ribozyme molecules are disclosed herein. For example, any of the disclosed siRNA molecules (14, 16, 18, 20, 22, 24, 26, 28, 30, or 32), or combinations thereof, such as at least 2, at least 3, or at least 4 of these sequences (such as 2, 3, 4, 5, 6, 7, 8, 9 or 10 of these), can be used at therapeutically effective amounts to decrease an amount of sNRF mRNA in the cell. In one example, the therapeutic molecule is a duplex (such as a duplex s formed by SEQ ID NOS: 13 and 14, 15 and 16, 17 and 18, 19 and 20, 21 and 22, 23 and 24, 25 and 26, 27 and 28, 29 and 30, or 31 and 32). However, this disclosure is not limited to the use of particular molecules that decrease mRNA.

Molecules that bind sNRF and prevent it from binding PKG or prevent its potentiating effect on growth factor action can be used to treat a cardiovascular disorder, such as heart failure. In particular examples, decreasing the biological activity of sNRF includes decreasing the interaction between sNRF and PKG. For example, to decrease the interaction between sNRF and PKG an agent that decreases, inhibits, or disrupts the interaction (for example, a binding interaction) between a sNRF and PKG can be administered (for example to a subject in need of therapy). Agents that recognize sNRF or PKG or portion thereof, can prevent binding of sNRF and PKG, thereby decreasing or inhibiting NPR desensitization or decrease sNRF's harmful effect on growth factor action. Examples of such agents include, but are not limited to, an anti-protein binding agent that specifically binds to sNRF or PKG, such as an antibody, peptide, or chemical.

Using Agents Identified by the Disclosed Screening Method

Agents identified using the methods disclosed herein can be used to treat a cardiovascular disorder. For example, one or more identified agents can be administered in a therapeutically effective amount to a subject having cardiovascular disease, or to a subject having an increased risk for developing cardiovascular disease. Such agents can be administered alone, or in the presence of a pharmaceutically acceptable carrier. In addition, agents identified using the disclosed methods can be administered in combination with other therapies.

Pre-Screening Subjects

In particular examples, the method includes determining whether the subject has cardiovascular disease or is at an increased risk for developing cardiovascular disease. Methods of determining whether a subject has heart disease or has an increased risk of developing heart disease in the future are known in the art. For example, serum levels of ANP, BNP, or cGMP can be detected in a sample obtained from the subject, wherein a serum level of >50-100 pg/ml for ANP, a serum level of >50-10 pg/ml for BNP, or serum level >8 pg/ml for cGMP, indicates that the subject has cardiovascular disease or is at an increased risk for developing cardiovascular disease.

Subjects known or found to have cardiovascular disease or an increased risk for developing cardiovascular disease are then administered a therapeutically effective amount of the therapeutic agent(s) disclosed herein.

Modes of Administration and Dosages

In one example, a therapeutically effective amount of an agent that decreases the biological activity of sNRF (for example by decreasing expression of sNRF mRNA) or increases the biological activity of NPRA/B, or decreases deleterious growth factor affects, or combinations thereof, is contacted with a cell, for example by administration to a subject. Such an agent can be used for prophylactic or therapeutic purposes.

For example, antisense oligonucleotides, ribozymes, triple helix molecules, miRs, and siRNA molecules that recognize sNRF can be administered to the subject to disrupt expression of sNRF. In a particular example, an expression vector including antisense RNA, ribozyme, triple helix molecule, miR, or siRNA molecules that targets sNRF nucleic acid sequence is introduced intravenously to a subject in a therapeutically effective amount. Uptake of the vector and expression of the antisense RNA, ribozyme, triple helix molecule, miR, or siRNA within cardiac cells (such as CF cells), offers a prophylactic or therapeutic effect by decreasing expression of sNRF within those cells, thus treating the cardiovascular disorder. In particular examples, expression of the antisense RNA, ribozyme, triple helix molecule, miR, or siRNA is under control of a promoter, such as an inducible promoter. The vector, or other nucleic acid molecule, can be introduced into a subject by any standard molecular biology method and can be included in a composition that includes a pharmaceutically acceptable carrier.

Screening Assays

Natriuretic peptides (NPs) are hormones produced by the heart that counteract heart failure pathways, such as total body fluid overload, over-activation of several hormones (such as angiotensin, aldosterone, endothelin, renin, the sympathetic nervous system, programmed cell death (apoptosis) and activation of inflammatory cytokines), and maladaptive thickening of the heart muscle (hypertrophy). However, ultimately, NP action is overwhelmed, chronic illness or and death can ensue. In this situation, called decompensated heart failure, despite very high circulating NP levels, NP actions are blunted, in part because the NPR (such as NPRA/B) becomes resistant to circulating NPs. Therefore, treatments are needed that overcome this ligand-induced NPR desensitization. For example, agents that permit reinvigoration of the NPRA/B, such that it becomes either responsive to the high levels of NPs in the circulation (for example by increasing the sensitivity of the receptor for NP ligands such as ANP or BNP), could be used to treat cardiovascular disease, such as heart failure.

The results provided herein demonstrate that sNRF controls NPRA resistance to the presence of NPs and potentiates the harmful effects of certain growth factors (such as FGF and TGFβ1). Therefore, sNRF provides a target for the identification of therapeutic agents. Specifically, sNRF and variants thereof have been identified that are capable of modulating NPRA's sensitivity to NPs or modulating the harmful action of certain growth factors (such as FGF and TGFβ1). These peptides associate (either directly or indirectly via other molecules) with PKG. It is shown herein that NPRA associates with PKG, and that association is involved in for maintaining the structure and function of the normal receptor complex. Thus, sNRF behaves as a decoy peptide or competitive inhibitor of the interaction between PKG and NPRA that maintains responsiveness of the receptor to NP ligands or behaves as a carrier/binding protein that regulates the sub-cellular location of PKG in the cell. It is also shown herein that sNRF affects downstream NP action. For example, sNRF represses NP's inhibitory action on cardiac fibroblast proliferation and differentiation through its ability to competitively bind PKG.

Based on these observations, methods are provided for screening test agents for their ability to increase the biological activity of a natriuretic peptide receptor (NPR), such as NPRA/B, to decrease sNRF-induced potentiation of harmful growth factor effects, or combinations thereof. Although monogenetic mouse models of NPRA dysfunction can be used to identify agents that treat heart failure, unless they are engineered to conditionally regulate the gene of interest, the analysis of down stream effects is complicated by redundant systems that continue to be expressed as the animal develops. The reductionist approach taken here permits a focused analysis of NPRA desensitization.

Exemplary test agents include proteins, nucleic acid molecules (such as RNAi) organic compounds, or inorganic compounds. In one example, increasing the biological activity of NPR, such as NPRA/B, includes increasing the sensitivity of the receptor for NPs (such as ANP or BNP). For example, an increase in the sensitivity of NPRA/B for ANP or BNP in the presence of the test agent, such as an increase of at least 25%, at least 50%, at least 90%, or at least 95%, indicates that the test agent can increase the biological activity of NPRA/B. In particular examples, this increase is relative to a reference value or a control, such as an amount of activity in the absence of the test agent. Methods for measuring the sensitivity of NPR for NP ligands are disclosed herein. For example a cGMP assay can be used.

In particular examples, the method includes contacting one or more test agents, growth factors, and NPs, with a cell under conditions that permit the test agent to interact with NPRA/B present in the cell. Exemplary cells include cardiac cells, such as cardiac myocytes or cardiac fibroblasts (CF). Subsequently, a determination as to whether the test agent increased biological activity of the NPRA/B, or decreased sNRF-induced potentiation of harmful growth factor effects, or both, is made. The cells include a reporter (such as a recombinant nucleic acid molecule that encodes a protein that permits for a determination of NPRA/B biological activity), NPRA or NPRB, and an intracellular fragment of NPRA that interferes with binding of cGMP-dependent kinase I (PKG) to NPR. The NPRA or NPRB in the cell can be native or recombinant.

In a particular example, the reporter is a recombinant promoter operably linked to a reporter nucleic acid sequence. For example, the promoter can be responsive to growth factors that are modulated by NP. In anther example, the reporter is a recombinant CNG channel expressed in the cell, whose activity can be detected by measuring the presence of $Ca^{2+}$ or $Mn^{2+}$, for example using fura-2.

Many different assays are available for determining whether the test agent increased biological activity of NPRA/B, decreased sNRF-induced potentiation of harmful growth factor effects, or combinations thereof. In one example, the method includes detecting a signal generated from a reporter (such as protein encoded by a reporter nucleic acid sequence or the influx of $Ca^{2+}$ or $Mn^{2+}$ through a recombinant CNG channel), wherein a change in the signal compared to the signal present in an absence of the test agent indicates that the test agent is an agent that increases biological activity of the NPRA/B, decreases sNRF-induced potentiation of harmful growth factor effects, or combinations thereof. For example, the presence of a decreased signal in the presence of the test agent as compared to a reference signal (such as a signal present in the absence of the test agent) indicates that the test agent is an agent that increases biological activity of NPRA/B. As the mechanism of sNRF-induced potentiation of harmful growth factor effects is not likely cGMP, inhibition of this pathway would not likely result in a decrease in cGMP. Therefore, while the use of a luciferase reporter (or other reporter operably linked to α-SMA) would show "quenching" of the signal in the presence of a sNRF-inhibiting agent (such as one that decreased sNRF-induced potentiation of harmful growth factor effects), the use of a CNG channel (that depends on modulation of cGMP) would not be affected.

In a particular example, the signal is a colorimetric signal (such as fluorescence or luminescence), or expression of a growth supplement in the presence of a nutrient deficient culture medium. Methods of detecting such signals are known in the art, and can include, but are not limited to, ELISA, spectrophotometry, flow cytometry, or microscopy.

In one particular example, the assay is a method for identifying agents that increase the biological activity of NPRA, NPRB, or both. In some examples, the method includes contacting a cell (such as a CF cell) with one or more test agents, with TGF-β, and with ANP or BNP. In specific examples, the cells include a recombinant α-SMA promoter operably linked upstream to a reporter nucleic acid sequence, NPRA/B, and a recombinant sequence comprising or consisting of SEQ ID NO: 4, 6, 38, 40 or 42. The method further includes measuring a signal produced by a protein encoded by the reporter nucleic acid sequence (such as luciferase) and determining whether the signal produced in the presence of the test agent is altered as compared to the signal in the absence of the test agent, where a change in the signal indicates that the test agent increases biological activity of NPRA, NPRB, or both. Such agents can be selected for further analysis, and in some examples are used to treat cardiovascular disease.

In another particular example, the assay is a method for identifying agents that increase the biological activity of NPRA, NPRB, or both. In some examples, the method includes contacting a cell (such as a CF cell) with one or more test agents, with TGF-β, and with ANP or BNP. In specific examples, the cells include a recombinant CNG channel (for example a cell infected with an adenovirus encoding the CNGA2 subunit, see Fagan et al., *J. Biol. Chem.* 274:12445-53, 1999, herein incorporated by reference), NPRA/B, and a recombinant sequence comprising or consisting of SEQ ID NO: 4, 6, 38, 40 or 42. The method further includes measuring a signal produced by influx of $Ca^{2+}$ or $Mn^{2+}$ (for example by measuring intracellular $Ca^{2+}$ or $Mn^{2+}$ using fura 2) and determining whether the signal produced in the presence of the test agent is altered as compared to the signal in the absence of the test agent, where a change in the signal (such as an increase or decrease) indicates that the test agent increases biological activity of NPRA, NPRB, or both. Such agents can be selected for further analysis, and in some examples are used to treat cardiovascular disease.

In another particular example, the assay is a method for identifying agents that decrease sNRF-induced potentiation of harmful growth factor effects. In some examples, the method includes contacting a cell (such as a CF cell) with one or more test agents, with TGF-β, and with ANP or BNP. In specific examples, the cells include a recombinant α-SMA promoter operably linked upstream to a reporter nucleic acid sequence, NPRA/B, and a recombinant sequence comprising or consisting of SEQ ID NO: 4, 6, 38, 40 or 42. The method further includes measuring a signal produced by a protein encoded by the reporter nucleic acid sequence (such as luciferase) and determining whether the signal produced in the presence of the test agent is altered as compared to the signal in the absence of the test agent, where a change in the signal indicates that the test agent decrease sNRF-induced potentiation of harmful growth factor effects. Such agents can be selected for further analysis, and in some examples are used to treat cardiovascular disease.

In another particular example, the assay is a method for identifying agents that decrease sNRF-induced potentiation of harmful growth factor effects. In some examples, the method includes contacting a cell (such as a CF cell) with one or more test agents, with TGF-β, and with ANP or BNP. In specific examples, the cells include a recombinant CNG channel (for example a cell infected with an adenovirus encoding the CNGA2 subunit, see Fagan et al., *J. Biol. Chem.* 274:12445-53, 1999, herein incorporated by reference), NPRA/B, and a recombinant sequence comprising or consisting of SEQ ID NO: 4, 6, 38, 40 or 42. The method further includes measuring a signal produced by influx of $Ca^{2+}$ or $Mn^{2+}$ (for example by measuring intracellular $Ca^{2+}$ or $Mn^{2+}$ using fura 2) and determining whether the signal produced in the presence of the test agent is altered as compared to the signal in the absence of the test agent, where no significant change in the signal (such as an increase or decrease) indicates that the test agent decreases sNRF-induced potentiation of harmful growth factor effects.

In another particular example, the method includes contacting a cell (such as a CF cell) with one or more test agents, with ANP or BNP, and optionally a growth factor.

In some examples, the disclosed assays are performed in a multiple well plate, such as a 6-, 12-, 24-, 96-, 384-, or 1536-well plate. In such examples, the cells are grown in the wells of the plate using standard tissue culture methods, and the desired agents (such as the test agents, growth factors, and NPs) added to the wells.

In some examples, test agents observed to increase the biological activity of NPRA/B, decrease sNRF-induced potentiation of harmful growth factor effects, or both, are selected. For example, such agents can be subjected to further analysis. In some examples such agents can be used to treat cardiovascular disease.

In addition to the disclosed in vitro assays, the method can include further analysis of the test agents found in vitro to increase the biological activity of the NPRA/B, decrease sNRF-induced potentiation of harmful growth factor effects, or both. For example, test agents that increase the biological activity of the NPRA/B, decrease sNRF-induced potentiation of harmful growth factor effects, or both, can be administered to a laboratory mammal having cardiovascular disease, and determining whether the test agent treats the cardiovascular disease. Animal models of cardiovascular disease are known in the art. Any route of administration can be used. Particular doses and routes can be determined by those skilled in the art. In some examples, a wide range of concentrations of the test agents are used (such as 1 nM-1 mM) for toxicity and $LD_{50}$ determinations.

Also provided by the present disclosure are agents identified using the disclosed methods.

Cells

Any type of cell can be used in the disclosed assay, as long as the cell expresses NPRA, NPRB (or both NPRA), as well as a sNRF that interferes with binding of (PKG) to NPRA. In particular examples, the cell expresses native NPRA, NPRB (or both), such as a cardiac cell. Examples of cardiac cells that can be used include cardiac myocytes or CFs. However, even in a cardiac cell, levels of NPRA/B can be increased by recombinantly expressing NPRA/B. In non-cardiac cells, such as HEK or Cos7 cells, the NPRA/B can be expressed recombinantly.

CFs express morphological and functional features of smooth muscle cells when the heart is stressed. These differentiated cells, called myofibroblasts, express microfilaments that are the force-generating elements in wound contraction (Hinz et al., *Mol Biol Cell.* 14:2508-19, 2003) and play a role in the cardiac response to myocardial infarction (Willems et al., *Am. J. Pathol.* 145:868-75, 1994), heart failure (Jaffe et al., *Adv. Exper. Med. Biol.* 430:257-66, 1997), and pulmonary vein stenosis in patients with cardiac malformations (Sadr et al., *Am. J. Cardiol.* 86:577-9, A10, 2000). The cytoskeletal protein alpha smooth muscle actin (α-SMA) has a mechanistic role in this process, and is also the principal molecular marker of CF differentiation into myofibroblasts. Undifferentiated CFs express NPRA but minimal NPs. When animals are stressed by experimental myocardial infarction or when CFs are grown in tissue culture and treated with growth factors such as TGF-β or FGF, CFs transdifferentiate into myofibroblasts, begin to express NPs, and express significant amounts of α-SMA. Thus, primary cultures of CFs are a model for screening test agents for their ability to increase biological activity of NPRA/B.

In particular examples, the CF used is a primary CF cell isolated from a mammal. For example, laboratory mammals (such as rats, mice, and rabbits) can be used as a source of cardiac tissue from which primary CFs can be obtained. Methods of generating CF cells from tissue are known in the art, and particular examples are provided herein.

One skilled in the art will appreciate that CF cells can be obtained from other sources, such as a tissue culture cell line. In one example, a CF cell expresses endogenous NPRA or NPRB. In other examples, a CF cell expresses recombinant NPRA or NPRB.

Promoters

In examples where the reporter includes a promoter operably linked to a reporter nucleic acid sequence, the promoter is ideally responsive to the presence of one or more growth factors that are modulated by NP. For example, the promoter can be one that is activated in the presence of a growth factor, wherein the activity of the growth factor is reduced in the presence of NP (such as ANP).

Particular examples of promoters that can be used include, but are not limited to: alpha smooth muscle actin (α-SMA) promoter, pro alpha 2(I) collagen promoter, β-myosin heavy chain promoter, or the atrial natriuretic peptide promoter itself.

Placement of the promoter upstream of the reporter can be achieved using standard molecular biology methods. In a particular example, the promoter is operably linked to the reporter and the resulting construct is part of a vector, which is introduced into CF cells using standard transformation methods.

Reporter Molecules

Reporter nucleic acid sequences operably linked to a promoter responsive to the presence of one or more growth factors that are modulated by NP include are those that encode a protein that produces a detectable signal when expressed, such as a calorimetric signal (for example a luminescent or fluorescent signal). Expression of a reporter can be controlled by a promoter sequence upstream of The reporter nucleic acid can include a promoter, the structural sequence of the reporter gene, and the sequences required for the formation of functional mRNA. Upon introduction of the reporter construct into cells, expression levels of the reporter gene can be monitored, for example by assaying for the reporter protein's enzymatic activity, or by measuring production of the protein directly (for example if the protein is a fluorescent or luminescent protein, such as green fluorescent protein (GFP), fluorescence or luminescence can be detected).

Particular examples include, but are not limited to: luciferase, β-galactosidase, chloramphenicol acetyltransferase (CAT), green fluorescent protein (GFP) (or variants thereof such as E-GFP). Sequences for such reporter molecules are well-known in the art. For example, a promoter that is responsive to the presence of one or more growth factors modulated by NP can be inserted into these plasmids that include the indicated reporter: p-lacZ (beta-galactosidase reporter), p-luc (firefly luciferase reporter) and p-cat (chloramphenicol acetyl transferase).

CNG Channels

In one example, the cell used in the disclosed in vitro assays includes a recombinant CNG channel (or functional subunit thereof, such as CNGA2) as the reporter. In such examples, the activity of NPRA/B is detected by measuring the presence of intracellular calcium (for example an increase in fura 2 fluorescence indicates that the NPRA/B is biologically active), or by measuring the quenching of fura 2 by manganese (for example a decrease in fura 2 fluorescence indicates that the NPRA/B is biologically active).

sNRF Molecules sNRF peptides that interfere with binding of PKG to NPR or potentiate the action of growth factors can be used to identify agents that increase the biological activity of NPR, reduce the harmful effects of growth factors in cardiovascular disease, or combinations thereof. The ability of sNRF to interfere with binding of PKG to NPR or to potentiate the action of growth factor can be determined using the methods disclosed herein. For example, immunoblotting and immunofluorescence microscopy (see Examples 7 and 10) can be used. However, it should be noted that it is not required that sNRF completely interfere with binding of PKG to NPR. For example, a reduction in detectable PKG-NPRA complexes of at least 80% can be sufficient, such as a reduction of at least 90% or at least 95%, or 100%, if sNRF acts by binding PKG and interfering with other PKG actions (for example interfering with PKG inhibition of thrombospondin expression). Similarly, in some examples the ability of sNRF to potentiate the harmful actions of a growth factor (such as FGF or TGFβ1) on cardiovascular disease can be an increase in the harmful actions of at least 10%, such as an increase of at least 20% or at least 50%.

The present disclosure provides sNRF sequences that interfere with binding of PKG to NPRA, such as SEQ ID NO: 4, 6, 38, 40 or 42. Also provided are nucleic acid molecules that encode such fragments. In particular examples, sNRF includes SEQ ID NO: 4, 6, 38, 40 or 42. In other particular examples, sNRF consists of SEQ ID NO: 4, 6, 38, 40 or 42. In some examples, sNRF includes at least 60 contiguous amino acids of the NPRA intracellular domain, such as at least 60 contiguous amino acids starting at amino acid 806 or 820 of SEQ ID NO: 2, for example at least 70 contiguous amino acids starting at amino acid 806 or 820 of SEQ ID NO: 2, at least 80 contiguous amino acids starting at amino acid 806 or 820 of SEQ ID NO: 2, or at least 90 contiguous amino acids starting at amino acid 806 or 820 of SEQ ID NO: 2. In particular examples, sNRF peptides that interfere with binding of PKG to NPRA do not include an NPRA kinase-like domain. In other or additional examples, sNRF includes an NPRA hinge domain. The location of such domains in NPRA are known in the art.

Although particular examples of sNRF that interfere with binding of PKG to NPR are disclosed, the assay is not limited to use of these sequences. For example, variants of SEQ ID NO: 4, 6, 38, 40 or 42 can be used. Particular examples of variants include the amino acid sequence shown in SEQ ID NO: 4, 6, 38, 40 or 42 having 1-10 conservative amino acid substitutions, such as 1, 2, 3, 4, 5, 6, 7, 8, 9, or 10 conservative amino acid substitutions. Particular conservative amino acid substitutions that can be made to SEQ ID NO: 4, 6, 38, 40 or 42 include but are not limited to: R1060K, F1030Y, S892T, or combinations thereof (wherein numbering refers to SEQ ID NO: 2). Particular amino acid substitutions (not necessarily conservative) that can be made to SEQ ID NO: 4, 6, 38, 40 or 42, include but are not limited to the mutations shown in FIG. 5 of Thompson and Garber (*J. Biol. Chem.* 270:425-30, 1995). Other variants of SEQ ID NO: 4, 6, 38, 40 or 42 include amino acid sequences that include 1-10 amino acid insertions or deletions to SEQ ID NO: 4, 6, 38, 40 or 42.

Methods of introducing a sNRF that interferes with binding of PKG to NPR into cells can be achieved using standard molecular biology methods. For example, a nucleotide sequence encoding for sNRF can be part of a vector (for example downstream from a promoter sequence), which can be introduced into a cell, thereby allowing expression of sNRF in the cell. Particular examples of vectors and transfection methods are disclosed; however those skilled in the art can readily adapt these teachings to use other vectors or transfection methods.

Growth Factors

Growth factors that can be used in the disclosed methods include those whose biological activity (such as expression) are altered during heart failure, and are modulated by NP. For example, growth factors include those whose biological activity (such as expression) is increased during heart failure, but whose biological activity is decrease in the presence of NP, such as ANP. In particular examples sNRF expression potentiates growth factor-induced production of α-SMA.

Particular examples of growth factors that can be used include, but are not limited to: FGF, EGF or TGF-β.

Methods of Diagnosing Cardiovascular Disease

Also provided by the present disclosure are methods of diagnosing cardiovascular disease.

In one example, the disclosed sNRF molecules are used to determine if a subject has cardiovascular disease (such as heart failure), or even determine the severity of cardiovascular disease. The method can include determining whether the subject expresses one or more of the disclosed sNRF molecules. If the subject expresses one or more of the disclosed sNRF molecules above a baseline or reference level (such as a level expected in a subject not having cardiovascular disease), this indicates that the subject has cardiovascular disease or has an increased risk of developing such disease. In particular examples, if the subject expresses any of SEQ ID NOS: 4, 6, 8, 38, 40 or 42 (or combinations thereof) above a baseline or reference level, this indicates that the subject has cardiovascular disease or has an increased risk of developing such disease. In other particular examples, if the subject expresses more of SEQ ID NO: 4 than SEQ ID NO: 6 or SEQ ID NO: 8, more of SEQ ID NO: 6 than SEQ ID NO: 8, more of SEQ ID NO: 40 than SEQ ID NO: 42, more of SEQ ID NO: 4 than SEQ ID NO: 42, more of SEQ ID NO: 40 than SEQ ID NO: 6, or more of SEQ ID NO: 40 than SEQ ID NO: 8, than this indicates a more severe form of cardiovascular disease.

Methods of determining whether a subject expresses sNRF (such as any of SEQ ID NOS: 4, 6, 8, 38, 40 or 42) are known in the art. For example, immunoassays and nucleic acid methods (such as Northern or Southern hybridization, PCR (for example quantitative PCR), and ELISA), can be used. In particular examples, a sample from the subject, such as a blood sample (or fraction thereof), cardiac tissue sample (for example from the ventricle), saliva sample, urine sample, or cheek swab sample, is analyzed for the presence of sNRF. If desired, the sample can be concentrated or purified before use. In a particular example, the sample includes cardiac tissue.

In one example, subjects with latent or subclinical cardiovascular disease will respond to a therapeutically effective amount of one or more therapeutic agents identified using the disclosed methods. Those not responding would not have dysregulation of NPR-PKG association, do not have sufficient sNRF-induced potentiation of deleterious growth factor effects, or combinations thereof. In a clinical setting an agent is said to increase the activity of NPRA/B (such as desensitized NPRA/B) when treatment of a subject with the agent results in the typical response of a patient as if the NPRA/B is not desensitized. In another clinical setting, an agent is said to decrease the activity of a growth factor (such as the deleterious effect of FGF or TGFβ1) when treatment of a subject with the agent results in the typical response of a patient as if growth factor action is not increased. Such subjects might have normalized blood pressure, increased urine output, suppression of numerous neuroendocrine markers of heart failure such as angiotensin, aldosterone, endothelin, renin, the sympathetic nervous system, or other growth factors, combing programmed cell death (apoptosis), decreased cardiac fibrosis, decrease in cardiac filling pressures, improvement of cardiac output, lessening of angina pectoris, normalization enlarged or aneurismal blood vessels, and in general diminution of the typical signs and symptoms of cardiovascular disease.

sNRF Proteins and Nucleic Acid Molecules

The present disclosure provides sNRF protein and nucleic acid sequences. For example, exemplary sNRF protein sequences are shown in SEQ ID NOS: 4, 6, 38, 40 and 42, and exemplary sNRF nucleic acid sequences are shown in SEQ ID NOS: 3, 5, 37, 39 and 41. Therefore, the disclosure provides isolated proteins that include or consist of any of SEQ ID NOS: 4, 6, 38, 40 or 42 as well as isolated nucleic acid sequences that include or consist of any of SEQ ID NOS: 3, 5, 37, 39 and 41.

However, the disclosure is not limited to these exact sequences, as one skilled in the art will appreciate that variants thereof can retain the same biological activity as these sequences. For example, a sNRF protein sequence can include one having at least 90%, at least 95%, or at least 98% sequence identity to any of SEQ ID NOS: 4, 6, 38, 40 and 42, as long as the variant retains the biological activity of sNRF, such as the ability to potentiate harmful growth factor effects, to disrupt PKG-NPR binding, or combinations thereof. Similarly, variants of the nucleic acid molecules shown in SEQ ID NOS: 3, 5, 37, 39 and 41 can still encode the identical amino acid sequence (for example due to the degeneracy of the code). In addition, variants of the disclosed sNRF nucleic acid molecules can encode a different amino acid sequence, but still encode a sNRF protein that retains sNRF biological activity. For example, a sNRF nucleic acid sequence can include one having at least 80%, at least 85%, at least 90%, at least 95%, or at least 98% sequence identity to any of SEQ ID NOS: 3, 5, 37, 39 and 41, as long as the variant encodes a protein that retains the biological activity of sNRF, such as the ability to potentiate harmful growth factor effects, to disrupt PKG-NPR binding, or combinations thereof. Methods for testing sNRF biological activity are disclosed herein.

Example 1

NPRA is Desensitized During Heart Failure

This example describes an in vitro model that mimics desensitization of NPRA observed during heart failure.

Neonatal rat CFs were transfected with an α-SMA-luciferase reporter construct driven by TGF-$\beta_1$ induction of the α-SMA promoter. After 24 hours, cells were treated daily with 100 nM TGF-$\beta_1$ for up to 4 days. On each successive day, some of the cells were treated with NP (ANP, 100 nM), and luciferase activity measured.

As shown in FIG. 1, expression of the luciferase reporter construct, driven by TGF-$\beta_1$ induction of the α-SMA promoter, was almost completely inhibited after 24 hours of NP treatment. However, progressively longer periods of NP treatment resulted in a steady decline in NP's inhibitory effects, indicating that NPRA is desensitized.

It is proposed herein that sNRF activity accounts for this NP resistance.

Example 2 sNRF is a Fragment of NPRA

This example describes the sNRF fragment of NPRA.

The genomic sequence of NPRA comprises 22 exons and introns (FIG. 2). A 816-bp partial NPRA cDNA sequence (SEQ ID NO: 37) contains the intron-15 sequence (nucleotides 1-215 of SEQ ID NO: 37), followed by contiguous exon 16-20 sequences (nucleotides 216-816 of SEQ ID NO: 37, with the coding sequence starting at nucleotide 256). This indicates that the mRNA is a fully processed, alternative transcript of the NPRA gene. The 215-nt, intron-15 sequence in this cDNA contains a stop codon 90 bases upstream of the 5' end of NPRA exon 16 that is in-frame with the NPRA open reading frame. The presence of this stop codon predicts that the protein encoded by this novel transcript would initiate at an in-frame AUG codon 45 bases downstream of the 5' end of exon 16. This NPRA fragment has been termed sNRF (soluble Natriuretic peptide Receptor-related Fragment).

Exemplary sNRF cDNA and protein sequence are provided in SEQ ID NOS: 39 and 40 (sNRF$^{(820-1061)}$), SEQ ID NOS: 41-42 (sNRF$^{(820-900)}$), SEQ ID NOS: 3 and 4 (sNRF$^{(806-1061)}$), and SEQ ID NOS: 5 and 6 (sNRF$^{(806-900)}$).

Example 3 sNRF cDNA and RNA Analysis

This example describes methods used to confirm that sNRF is an alternative NPRA gene-derived transcript initiating in intron 15, and is present in human cells.

RT-PCR of cDNA reversed-transcribed from total RNA extracted from human kidney and human genomic DNA was performed using primers corresponding to the intron-15 sequence and a 3' segment of the exon-17 sequence (see "a" and "b" in FIG. 2, SEQ ID NOS: 43 and 44, respectively). The resulting PCR product from human kidney cDNA had the predicted size of 389 bp, whereas the PCR product of human genomic DNA was 477-bp, presumably containing the additional 88-nt, intron-17 sequence.

An intron 15-specific probe (SEQ ID NO: 35) was random-primed with $^{32}$P-ATP and used to probe a Northern blot containing total RNA from normal human heart and RNA from three heart explants prior to cardiac transplantation. The 18S ribosomal bands were of equal intensity when the two groups were compared (normal versus failing heart). However, as shown in FIG. 3, a strongly hybridizing band was observed in failing heart myocardium, but not in normal heart. This 1.5-kb band is consistent with the size predicted for an alternative NPRA gene-derived transcript initiating in intron 15 (full-length NPRA mRNA is 4 kb). Therefore, sNRF and full-length NPRA transcript levels vary independently in human heart.

These results demonstrate that sNRF is a naturally occurring transcript present in the human heart.

Example 4

Differential sNRF Expression in Human Heart Failure

This example describes methods used to compare sNRF expression between normal hearts and heart failure hearts.

The increased expression of sNRF mRNA observed in the Northern blot of pooled samples of failing myocardium (FIG. 3) indicates that sNRF is up-regulated in heart failure. To confirm this hypothesis, sNRF mRNA expression was measured in five additional explanted hearts prior to heart transplantation using quantitative, real-time RT-PCR.

cDNA from reverse-transcribed poly(A)$^+$ RNA from a transplant patient with dilated cardiomyopathy (DCM) was compared to a control sample obtained from another patient shortly after death from a non-cardiac cause. Quantitative, real-time PCR was performed using primers "a" and "b" shown in FIG. 2 (SEQ ID NOS: 43 and 44). Each sample was measured in triplicate using a Taqman probe (SEQ ID NO: 36, wherein the 5' label is FAM and the 3' label is TAMRA) with values adjusted relative to an endogenous GAPDH control using an ABI 7300 real-time PCR system. As shown in FIG. 4A, a 5.7-fold increase in sNRF mRNA was observed in the DCM heart compared to the "normal" heart.

Total RNA was extracted from an explanted heart from a patient with hypertrophic cardiomyopathy. In that heart, sNRF mRNA expression was nearly 70-fold higher when compared to RNA obtained from a "normal" heart (Ambion) (FIG. 4B, upper panel). The relative expression of the full-length NPRA transcript was measured using a probe that spans exonic sequence upstream of sNRF (i.e., a probe complementary to exon 7 and 8 exonic sequence not present in sNRF). There was essentially no difference between full-length NPRA expression in the control heart compared to the patient with HCM (FIG. 4B, lower panel).

In three additional explanted failing hearts, sNRF and NPRA transcripts also exhibited independent changes in expression. Relative sNRF expression was 1, 4, and 21-fold, whereas NPRA expression levels were 1.5, 1, and 1.3-fold, respectively, in each of the failing hearts (FIG. 4C).

Total RNA extracted from 17 explanted pediatric hearts prior to transplantation was analyzed for sNRF expression as described above. Highly variable sNRF expression was also observed in myocardial samples obtained from children with a variety of cardiomyopathies (FIG. 4D).

Taken together, these data indicate that regulation of sNRF expression from its putative promoter in intron 15 is independent of NPRA expression initiated at the NPRA promoter flanking exon 1.

Example 5 sNRF and NPRA Expression in Normal and Diseased Heart Tissue

This example describes methods used to compare sNRF and full-length NPRA expression between normal hearts and diseased hearts. As shown in FIG. 4B, differential expression of sNRF, but not NPRA, was detected in normal versus diseased heart tissue. To confirm this result, more hearts were analyzed.

sNRF and full-length NPRA mRNA levels in the left ventricles of patients with and without heart failure were measured to demonstrate that sNRF gene expression correlates with heart failure. Using quantitative RT-PCR both sNRF and full-length NPRA gene expression were compared in 7 explanted hearts from patients with heart failure (patients receiving a transplant) to 4 normal hearts using the methods described in Example 4.

One skilled in the art will appreciate that "normal" heart tissue can be obtained from patients without heart failure as the primary diagnosis. For example, heart tissue can be obtained during surgery, for example from coronary artery bypass grafting where small amounts of muscle are removed when coronary arteries are dissected to connect the graft, septal myectomy for subaortic obstruction, ventricular septal defect enlargement during Rasteili-type procedures, and subaortic conal muscle resection in double-outlet right ventricle. In addition, commercial "normal" human heart mRNA is available (Ambion, Clontech, Biochain, and others).

For each subject, serum brain-type natriuretic peptide (BNP) and C-reactive protein (CRP) (an inflammatory marker that correlates with heart failure severity) levels were determined, as well as clinical heart failure NYHA status. Other data, including 6-minute walk, exercise $Vo_2$, echocardiographic parameters including left-ventricular mass, end diastolic dimensions, fractional shortening and ejection fraction, can be recorded. "Normal" patients presumably occupy NYHA classes I-3, while "heart failure" patients, having been listed for orthotopic heart transplantation, were NYHA class IV.

At the time of surgery, myocardial samples were flash-frozen in liquid nitrogen within seconds of removal and stored at −80° C. Total mRNA was extracted according to the manufacturer's protocol (RNeasy, Qiagen). Using this technique 10 µg of RNA per 10 mg of heart tissue was obtained. Quantitative RT-PCR in triplicate using sNRF-specific primers ("a" and "b", FIG. 2) and full-length NPRA-specific primers directed at exonic sequences upstream of the sNRF-unique region was performed as described in Example 4. In rare cases where less than 10 mg is available from a single patient, tissue from patients of equivalent NYHA classification can be pooled. Quantitative RT-PCR was used to measure either sNRF mRNA expression relative to GAPDH as an endogenous control or absolute mRNA levels based on interpolation from a standard curve constructed with sNRF plasmid DNA of known concentrations. Measurements were performed in triplicate, with a deviation from the median value is less than 0.2%.

Figure 5A:
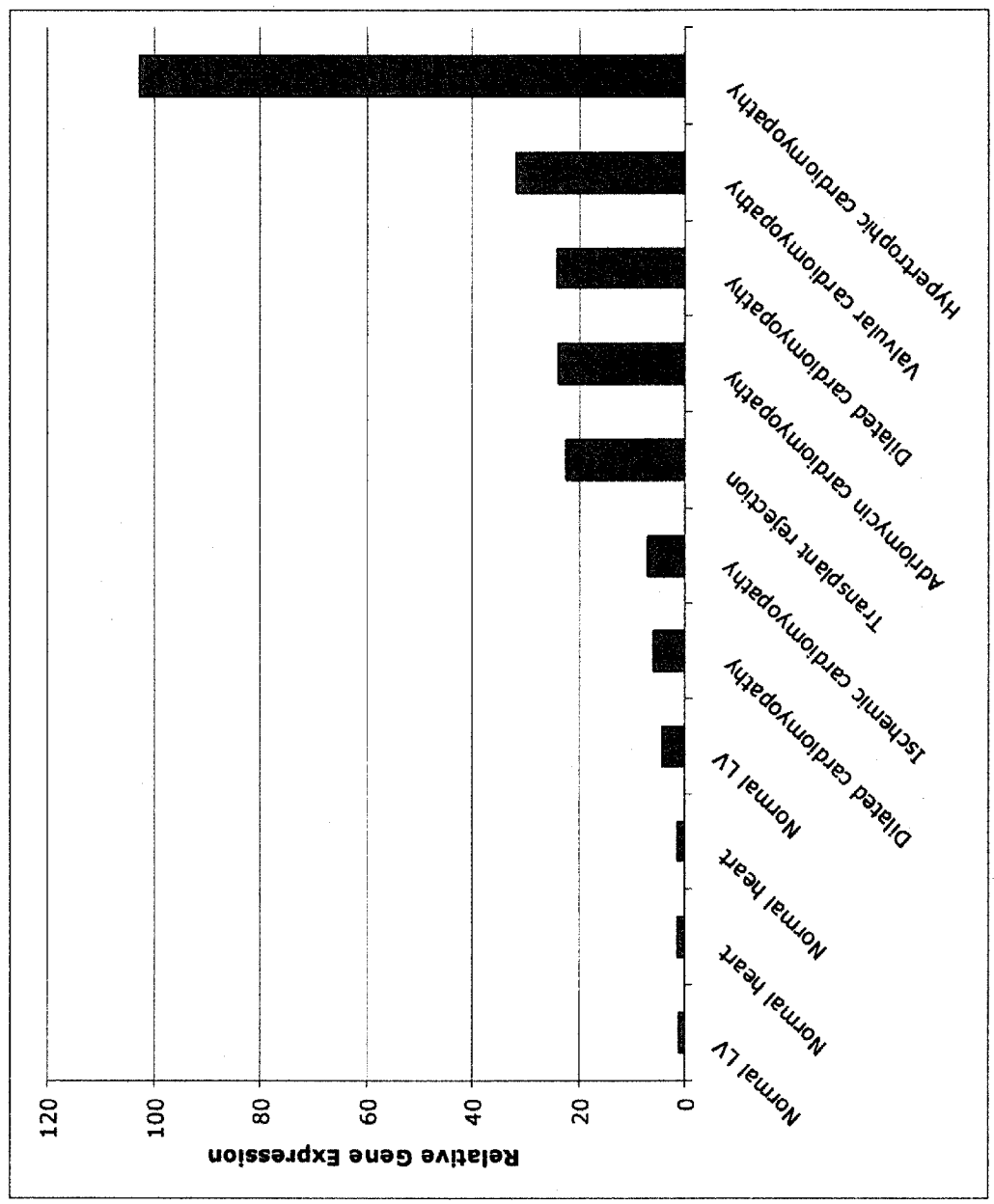
FIGS. 5A and 5B are bar graphs showing the relative amount of (A) sNRF and (B) NPRA mRNA expression in normal hearts or heart failure hearts.
Figure 5B:
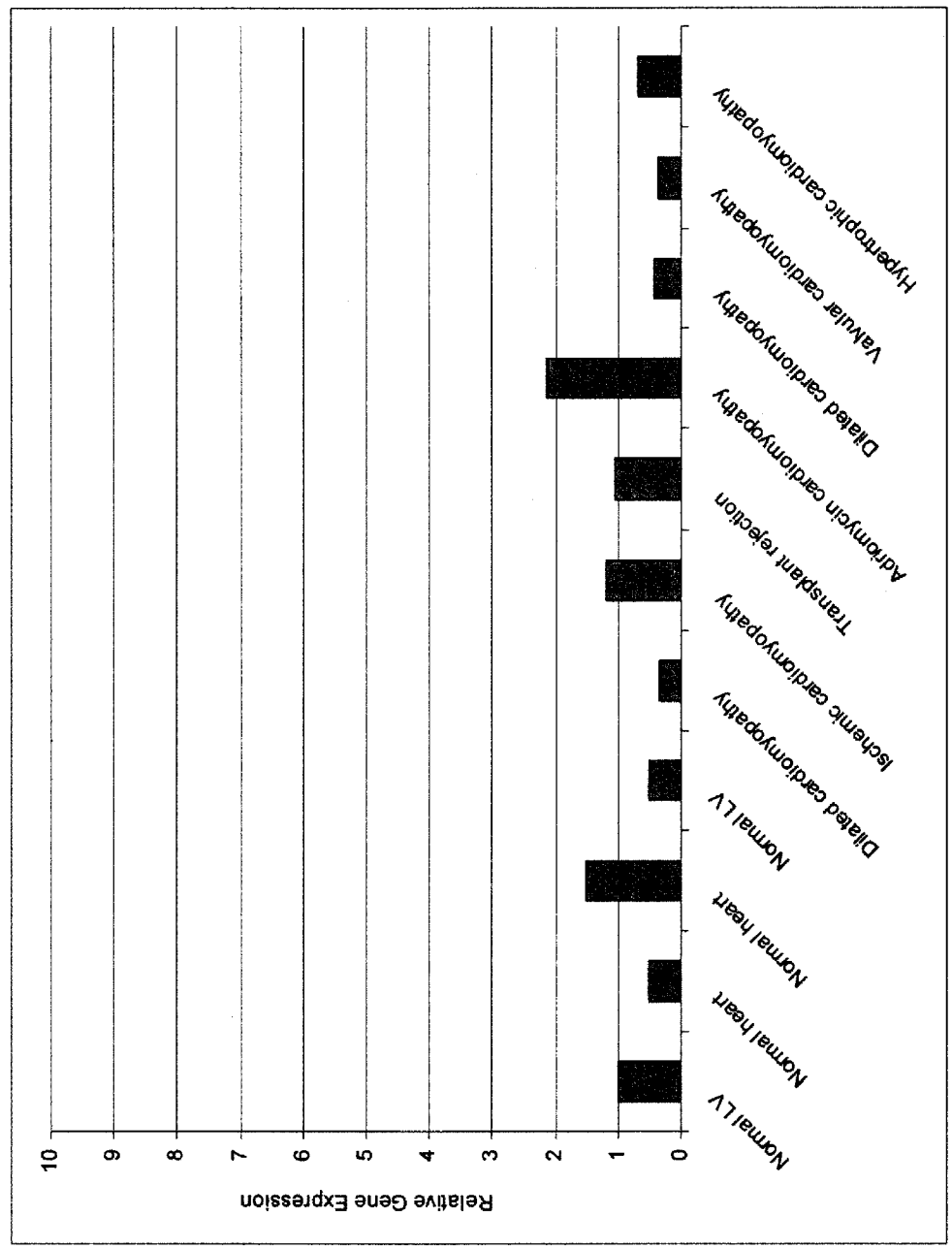

As shown in FIG. 5A, sNRF expression was significantly higher in the heart failure hearts compared to the control hearts in all cases. Also, NPRA gene expression had minimal variability (<2-fold change in all cases) and was not different when control and heart failure hearts were compared (FIG. 5B) whereas significant differential expression was observed in sNRF expression in the heart failure hearts compared to the control hearts (FIG. 5A).

Therefore, sNRF and NPRA are alternative products of the NPRA gene and sNRF (but not NPRA) is differentially regulated in human heart failure.

Similar methods can be used to measure sNRF in isolated human cardiomyocytes, and can be compared to CF sNRF levels. For example, RNA can be extracted from the myocytes that remain in the supernatant following the disassociation of the CF. Heart failure and CF and myocyte sNRF gene expression can be compared to the levels in CF and myocytes obtained from recent post-mortem individuals with no cardiac history by Northern blot.

Example 6

Determining Severity of Heart Failure with sNRF Expression

This example describes methods that can be used to correlate the severity of clinical heart failure with sNRF mRNA expression. As described in Examples 4 and 5, quantitative RT-PCR can be used to measure sNRF expression in heart tissue. The information obtained from heart failure patients (such as those described in Example 5), can be used to determine if levels of sNRF expression correlate with severity of heart failure.

Using SPSS software Version 14, analysis frequencies can be run on categorical variables (NYHA class, etc.) and descriptive analysis on continuous variables in order to locate and isolate outliers. Based on these results, transformations will be performed as appropriate. Next, sNRF expression can be compared to continuous variables (BNP, CRP, etc.) using independent t-tests and one-way ANOVAs. Chi-square will be used to assess independent categorical-type variables for co-linearity. The primary model will be a multivariate regression analysis using dummy coding for the independent categorical variables. Initial modeling will use stepwise regression to define the best sNRF predictors. Variables will be added one at a time using standard techniques (entry criterion: p value <0.10, exit criteria: p value >0.15). It is expected that NYHA class, BNP level, and CRP will be among these.

If this analysis demonstrates that myocardial sNRF mRNA expression levels are predictive of heart failure risk or predictive of significant clinical end points such as heart transplantation or death, then a logistic regression model will be employed. Logistic regression will also be used to explain confounding among the independent variables and to create associated odds ratios.

If there is a correlation between sNRF expression and severity of heart failure, routine methods of measuring sNRF expression in clinical samples can be used to assess the severity of heart failure in a patient.

Example 7

PKG and NPRA Associate in Cardiac Fibroblasts

This example describes methods used to demonstrate that cGMP-dependent protein kinase I (PKG) associates with natriuretic peptide receptor A (NPRA) in primary cardiac fibroblast (CF) cells.

A minimal PKG binding domain in NPRA was identified by expression of sNRF (sNRF$^{(806-1061)}$ (SEQ ID NO: 4), sNRF$^{(806-900)}$ (SEQ ID NO: 6) and sNRF$^{(806-860)}$ (SEQ ID NO:8)) in transfected CFs and assayed their ability to block PKG-NPRA binding. None of the fragments contained either the extracellular ligand-binding domain (amino acids 54-415) or the kinase-like domain (amino acids 547-804) of NPRA. sNRF$^{(806-1061)}$ includes both the an amphipathic helix (so-called hinge domain) and the C-terminal guanylyl cyclase domain. sNRF$^{(806-900)}$ excludes the cyclase-containing domain. sNRF$^{(806-860)}$ contains only the hinge domain.

HEK-NPRA cells were transiently transfected with insert-less pcDNA3 plasmid vector or pcDNA3-sNRF$^{(806-1061)}$. All slide wells were treated with atrial natriuretic peptide (ANP) (100 nM; Sigma-Aldrich #A1663) for 15 minutes. Cells were decorated with monoclonal flag antibody specific for FLAG-NPRA (red) and polyclonal PKG antibody (green). Overlapping regions of PKG and NPRA appeared yellow-orange. PKG staining was absent when anti-PKG antibody was pre-adsorbed with recombinant PKG protein (Calbiochem). In control experiments, no immunofluorescence was seen in the absence of primary antibody.

Expression of sNRF$^{(806-1061)}$ in HEK293 cells stably overexpressing FLAG-epitope tagged NPRA (HEK-NPRA cells) inhibited translocation of cytosolic PKG to the plasma membrane, indicating that sNRF$^{(806-1061)}$ interferes with PKG NPRA association. Although PKG-sNRF$^{(806-1061)}$ co-localization could be readily seen in CFs, inhibition of translocation was more difficult to appreciate in these smaller cells expressing only endogenous NPRA. Therefore, expression of sNRF$^{(806-1061)}$ blocks NP-induced PKG membrane translocation.

To demonstrate that PKG and NPRA interact in vivo, the ability of sNRF to immunoprecipitate PKG was determined in primary CF cells. Neonatal rat ventricular fibroblasts (CFs) were cultured from 1 to 2-day-old Harlan Sprague-Dawley rats as described previously (Simpson, *Circulation Res.* 56:884-94, 1985). Briefly, ventricles were dissected free from atria and quartered. Following dissociation in ADS buffer containing 1.5 mg/ml trypsin (Gibco #27250-018) and 1% DNase solution (2 mg/ml DNase type II, 150 mM NaCl) with serum neutralization the collected cells were pre-incubated in media at 37° C. for 90 minutes to allow CF attachment to the bottom of culture dishes. CFs were incubated in plating media for 48 hours, divided into 6-well culture plates or dual-well chamberslides, and grown to 50% confluency in DMEM with 10% FBS prior to use. Others have shown that cells cultured in this fashion exhibit positive staining for vimentin, negative staining for von Willebrand factor, α-smooth muscle actin, and sarcomeric actin, indicating that there is no relevant contamination of the cardiac fibroblast culture with endothelial cells, smooth muscle cells, or cardiac myocytes (Tsuruda et al., *Circ. Res.* 90:128-34, 2002).

CFs were transiently transfected with nucleic acid molecules encoding sNRF$^{(806-1061)}$, sNRF$^{(806-900)}$, or sNRF$^{(806-860)}$ using routine methods. Briefly, PCR-generated, 5'-FLAG epitope-tagged sNRFs were subcloned into the BamHI and EcoRI sites of pCDNA3 (Invitrogen) and sequenced to verify construction accuracy. The following primer sequences were used to generate 5'-FLAG epitope-tagged NPRA fragments: sNRF$^{(806-1061)}$:

```
Forward:
                                       (SEQ ID NO: 9)
GGGTGGATCCACCATGGACTACAAAGACGATGACGACAAGAGGGAGAACA
GCAGCAACAT,
Reverse:
                                       (SEQ ID NO: 10)
CGGGAATTCTCAGCCTCGGGTGCTACTCC;

sNRF(806-900):
Forward:
                                       (SEQ ID NO: 9)
GGGTGGATCCACCATGGACTACAAAGACGATGACGACAAGAGGGAGAACA
GCAGCAACAT,
Reverse:
                                       (SEQ ID NO: 11)
CGGGAATTCTGACAGGGTCACCACCTGCATGG;

sNRF(806-860):
Forward:
                                       (SEQ ID NO: 9)
GGGTGGATCCACCATGGACTACAAAGACGATGACGACAAGAGGGAGAACA
GCAGCAACAT,
Reverse:
                                       (SEQ ID NO: 12)
CGGGAATTCTGACTCAGCCACTGAGTGAGGCA.
```

The ability of the NPRA fragments to immunoprecipitate PKG was determined in the primary CF cells transfected with the 5'-FLAG epitope-tagged NPRA fragments as follows. CFs were collected and solubilized in 1 ml ice-cold IP buffer containing 50 mM Hepes, pH 7.4, 5 mM NaCl, 5 mM EDTA, 10% glycerol, 0.5% Triton X-100, and protease inhibitors (complete mini-tablet, Roche). Equal concentrations of lysate were incubated with 20 μl anti-FLAG M2 affinity gel (Sigma #F-3165) for 18 hours at 4° C. before 5 sequential 5-minute centrifugations with 1 ml fresh buffer before elution with hot SDS sample buffer (0.25 M Tris-HCL, pH 6.8, 20% glycerol, 4% SDS, 10% β-mercaptoethanol, and 0.0025% bromophenol blue). Samples were boiled for 10 minutes and 30-μL aliquots of eluate were loaded onto SDS-PAGE gels (5% acrylamide stacking phase, 7.5% or 10% acrylamide resolving phase gels). Gels were transferred to nitrocellulose using a Bio-Rad Liquid Transfer Unit in transfer buffer with 10% methanol. Before blocking (5% nonfat dry milk, TBS, 0.03% Tween) and incubation with primary antibody (Santa Cruz Biotechnology) overnight at 4° C. Blots were then washed 3 times for 5 minutes with TBST before incubation with a 1:5000 dilution of horseradish peroxidase-conjugated donkey anti-IgG antibody (Jackson Laboratories) in TBST. Bound antibody was detected with chemiluminescent substrate (Western Lightning ECL, PerkinElmer Life Sciences).

sNRF$^{(806-1061)}$ and sNRF$^{(806-900)}$, but not sNRF$^{(806-860)}$, co-immunoprecipitated PKG, indicating that both sNRF$^{(806-1061)}$ and sNRF$^{(806-900)}$ can bind PKG and potentially compete with endogenous NPRA for PKG binding. sNRF$^{(806-900)}$ failed to associate with full-length NPRA, either in the presence or absence of activated PKG, indicating that the fragment's effects are not based on its ability to dimerize with the full-length receptor.

Therefore, sNRF$^{(806-900)}$, the shortest fragment observed to associate with PKG, was used to demonstrate the effect of PKG-NPRA association on downstream actions, receptor cyclase activity, and receptor phosphorylation.

Example 8

PKG Phosphorylation of NPRA in Inhibited by sNRF

This example describes methods used to demonstrate that PKG can phosphorylate NPRA, and that this phosphorylation is inhibited by sNRF.

Phosphorylation of specific serine and threonine residues within the NPRA kinase homology domain is required for ANP-induced action. For example, it has previously been shown that deletion of the kinase homology domain itself results in ligand-independent, constitutive receptor guanylyl cyclase activity (Wedel et al., *Proc. Nat. Acad. Sci. USA* 94:459-62, 1997; Chinkers et al., *Science.* 245:1392-4, 1989).

To confirm that PKG, a serine-threonine kinase, is capable of phosphorylating NPRA, the following methods were used. Cos7 cells were transfected with a cDNA vector encoding full-length NPRA (SEQ ID NO: 2) or with an empty vector, and treated with PKG (20 U). Lysates prepared from the cell membranes of Cos7 cells were treated with recombinant PKG and then divided into two aliquots. One aliquot was incubated (30 minutes) with 8-bromo-cGMP and [$^{35}$S] ATPγS and then separated by SDS-PAGE, blotted to Immobilon membranes, and visualized by autoradiography. The other aliquot was separated similarly and then probed with anti-NPRA antisera (ABCAM ab14356).

As shown in FIG. 6A, SDS page gels demonstrated a phosphorylated 137 kD protein that corresponded to full-length NPRA.

To demonstrate that PKG phosphorylates NPRA in an ANP-dependent manner, CF cells were transfected with either insertless vector or sNRF$^{(806-900)}$ (see Example 7 and FIGS. 6C and 6D) and treated with or without ANP for 5 minutes in the presence or absence of 1 μM of the PKG inhibitor KT5823 (Alexis Biochemicals, Cat #270-087-C100). To identify receptor phosphorylation by PKG, [$^{35}$S] ATPγS was employed as a substrate. [$^{35}$S] incorporation into NPRA was analyzed according to the method previously described (Joubert et al., Biochem. 40:11096-105, 2001). Briefly, the treated CFs were scraped into 100 μl ice-cold incubation buffer (25 mM HEPES, pH 7.4, 50 mM NaCl, 5 mM MgCl$_2$, 0.2 μM okadaic acid, 1 mM Na$_3$VO$_4$, 10 mM NaH$_2$PO$_4$, 10 mM NaF, and protease inhibitors (complete mini-tablet, Roche) and lysed by repeated passage through a 22-gauge needle. Lysates were added to incubation buffer containing 1 μCi [$^{35}$S]ATPγS (specific activity >1000 Ci/mmol), final volume of 200 μl, incubated at 37° C. for 30 minutes. Proteins were analyzed by SDS-PAGE (7.5%) and subsequent autoradiography.

Since the lysates used in the kinase reaction also contained an array of protein phosphatase inhibitors, the possibility of reduced phosphatase activity as a mechanism for receptor phosphorylation or increased phosphatase activity as a major mechanism sNRF$^{(806-900)}$-induced inhibition phosphorylation was excluded. In other control experiments, PKG treatment resulted in phosphorylation of whole cell lysate preparations from HEK-NPRA cells, but not from cells expressing little or no NPRA. As shown in FIGS. 6B-5D, both KT5823 or expressed sNRF$^{(806-900)}$ protein reduced ANP-induced NPRA phosphorylation to control levels.

To ensure that the 137-kD phosphorylation band observed in the CFs after ANP treatment was, in fact, NPRA, HEK293 or HEK-NPRA were treated with ANP with or without KT5823 as described above. The lysates were divided into two aliquots. One aliquot was incubated with [$^{35}$S] ATPγS and then separated by SDS-PAGE, blotted to Immobilon membranes, and visualized by autoradiography. The other aliquot was separated similarly and then probed with anti-NPRA antisera, stripped and re-probed with anti-α-tubulin to assure equal protein loading. Robust phosphorylation of a 137-kD protein occurred in the NPRA-expressing cells, but not in control cells (FIG. 6B). Since both KT5823 and sNRF$^{(806-1061)}$ inhibit cytosolic-to-plasma membrane translocation of PKG, PKG-NPRA association appears to be required for PKG-induced NPRA phosphorylation.

Therefore, expression of sNRF$^{(806-900)}$ results in ligand-independent, constitutive cGMP generation, and PKG phosphorylation of NPRA is inhibited by sNRF. The earlier observation, that the elimination of PKG catalytic activity by KT5823 inhibits PKG translocation (Airhart et al., J. Biol. Chem. 278:38693-8, 2003), and the current observation that both KT5823 and sNRF protein expression blocks both basal and NP-induced receptor phosphorylation, indicate that PKG's kinase activity is involved in regulating receptor responsiveness. Based on these data, a model is proposed in which basal PKG-NPRA association and NPRA phosphorylation allows ligand-induced PKG translocation and receptor phosphorylation. Subsequently, NP-induced further accumulation of PKG and increased NPRA phosphorylation, in turn, amplifies cyclase activity.

In summary, these results demonstrate that the association of PKG with NPRA modulates NPRA responsiveness to NPs through PKG's NPRA kinase activity in native cardiac cells expressing only endogenous PKG and NPRA. A sNRF$^{(806-900)}$ fragment (SEQ ID NO: 6) that does not contain NPRA's extracellular ligand-binding or intracellular kinase homology domains, but does contain the hinge and a small 5' portion of the C-terminal guanylyl cyclase domain, associates either directly or indirectly with PKG. By sequestering PKG from its NPRA binding site, sNRF attenuates PKG's function as an adapter or bridging protein that has a permissive effect on ANP-induced conformational changes in NPRA and dimerization of its C-terminal cyclase domains.

These results demonstrate that PKG potently phosphorylates NPRA in an NP-dependent manner, and that a blocker of PKG activation, KT-5823, inhibited this effect. Furthermore, sNRF expression inhibits NP-induced NPRA phosphorylation. Since sNRF binds PKG and also blocks NP-dependent PKG translocation, sNRF inhibits NPRA phosphorylation and function by altering PKG's interaction with NPRA. These findings indicate that PKG plays a role in the regulation of receptor responsiveness Based on these observations, methods of (1) decreasing biological activity of sNRF to treat heart failure and (2) screening compounds for their ability to enhance the sensitivity of an NPR for NP ligands, are disclosed.

Example 9

Effect of PKG-NPRA Association on NPRA Catalytic Activity

This example describes methods used to demonstrate that expression of sNRF$^{(806-900)}$ significantly reduces CFs response to ANP.

The ability of sNRF$^{(806-900)}$ to reduce or inhibit downstream effects by modulating the intrinsic guanylyl cyclase activity of NPRA, was determined by measuring total cGMP levels in NP-treated CFs. CFs were transfected with insertless vector or sNRF$^{(806-900)}$ as described in Example 7 and treated with ANP (100 nM) for 15 minutes. cGMP concentration was determined by enzyme immunoassay using a commercial kit (Enzyme immunoassay Biotrak EIA System, Amersham Biosciences). In all experiments, cells were treated with 100 μM IBMX with or without ANP.

As shown in FIG. 7, ANP treatment significantly increased intracellular cGMP concentration in CF cells. However, sNRF$^{(806-900)}$ alone also significantly increased cGMP levels. This effect was not due to an effect on phosphodiesterase activity, because all experiments were conducted in the presence of the non-selective phosphodiesterase inhibitor, IBMX. Furthermore, since sNRF$^{(806-900)}$ does not appear to directly associate with the full-length receptor, and since this fragment lacks the guanylyl cyclase domain, it is unlikely that this effect is due to sNRF$^{(806-900)}$ functioning as a dominant negative. ANP treatment of sNRF$^{(806-900)}$-expressing cells did not lead to an additional increase in cGMP concentration, compared to the effect of sNRF$^{(806-900)}$ alone (FIG. 7).

Therefore, sNRF$^{(806-900)}$ expression in CFs leads to constitutive receptor activation and resistance to further stimulation by ANP, by isolating PKG from its NPRA binding sites. This indicates that expression of sNRF mimics desensitization of NPRA for ANP ligand that occurs during heart failure.

Example 10 sNRF Blocks NP Inhibition of bFGF-Induced Cardiac Fibrosis

This example describes methods used to demonstrate that the association of PKG with sNRF influences NPRA-mediated signaling, and that sNRF reverses ANP inhibition of bFGF-induced α-SMA expression.

The degree of CF-induced myocardial fibrosis caused by their elaboration of collagen and extracellular matrix after myocardial infarction and during cardiac remodeling largely determines the outcome of clinical heart failure. When animals are stressed by experimental myocardial infarction, or when CFs are grown in tissue culture and treated with growth factors such as TGF-β$_1$ or bFGF, they differentiate into myofibroblasts, begin to express NPs, and produce significant amounts of α-SMA. NP treatment of growth factor-stimulated CFs inhibits their proliferation and expression of collagen, extracellular matrix, and α-SMA. Thus, CFs are a model in which to determine the downstream effects of NPRA activation because they express endogenous NPRA and PKG, their NP system is closely regulated as cardiac disease develops, and, in general, CFs play a role in the development of cardiac disease.

NP's ability to inhibit growth factor-induced CF differentiation into myofibroblasts was determined as follows. CFs were transiently transfected with insertless pcDNA3 vector or pcDNA3 encoding sNRF$^{(806-900)}$ (see Example 7). The transfected CFs were then treated for 48 hours with 10 ng/ml basic fibroblast growth factor (FGF; Sigma-Aldrich #F0291) in the presence or absence of 100 nM ANP. Alpha-smooth muscle actin (α-SMA) protein expression, the principal marker of CF differentiation, was assessed by Western blotting and immunofluorescence microscopy. Vimentin staining was used as a loading control because it is expressed equally in fibroblasts and transdifferentiated myofibroblasts.

For the immunofluorescence microscopy, slide wells were treated as described in Example 7 and incubated with anti-α-SMA and anti-vimentin antibody as well as phalloidin to stain for actin. Briefly, cells were rinsed twice with phosphate-buffered saline (PBS) and fixed with 3.7% formaldehyde in PBS for 10 minutes. After fixation, cells were rinsed with PBS and permeabilized with 0.3% Triton X-100 in PBS for 10 minutes and blocked for 1 hour in 1% horse serum, 0.2% bovine serum albumin in PBS. Cells were then incubated with primary α-SMA antibody (ABCAM ab7817) and primary vimentin antibody (ABCAM ab7783) diluted in blocking solution for 1 hour and washed three times with blocking solution for 5 minutes. The cells were incubated with the appropriate fluorescent secondary antibodies for 1 hour (FITC and Cy5 conjugated-secondary donkey antibodies; Jackson Laboratories) and a 1:1000 dilution of rhodamine-phalloidin (Molecular Probes), which was used to visualize actin fibers. After three PBS washes, the cells were mounted on glass coverslips using Slowfade Antifade mounting medium (Molecular Probes). Images were acquired using a Leica DMRA Fluorescent Microscope equipped with a 40×/0.7 HCX PL Fluotar objective, Leica N3, Y5, and L5 filter cubes, a Hamamatsu Ocra-ER digital camera, and Openlab 3 software.

As shown in FIGS. 8A and 8B, treatment of CFs with growth factor significantly increased α-SMA protein expression in CFs. ANP treatment inhibited bFGF-induced α-SMA protein expression in cells transfected with insertless vector (FIGS. 8A, 8B). However, expression of sNRF$^{(806-900)}$ reversed ANP's inhibitory effect on growth factor-induced α-SMA protein expression. While the Western immunoblots demonstrated equal amounts of vimentin in all treatment groups, immunofluorescence microscopy indicated that control and FGF-treated cells had diffuse nuclear and cytosolic staining, whereas nuclear to cytosolic translocation of vimentin was observed in the presence of ANP, an effect that was inhibited by expression of sNRF$^{(806-900)}$.

Therefore, association between PKG and an intracellular domain of the NPRA C-terminus is needed for NP's inhibitory action on myofibroblast differentiation. The region on PKG that binds to NPRA is referred to the NPRA association domain on PKG (NAD), and the region on NPRA binds to PKG is referred to the PKG association domain on NPRA (PAD).

Example 11 sNRF Blocks NP Inhibition of TGF-β$_1$-Induced Cardiac Fibrosis

This example describes methods used to demonstrate that sNRF reverses ANP inhibition of TGF-β$_1$-induced α-SMA expression.

TGF-β$_1$ signaling is required for angiotensin effects in the heart, and NPs oppose TGF-β$_1$ effects in CFs. To demonstrate the effect of sNRF expression on TGF-β$_1$-induced α-SMA luciferase reporter expression, and to determine if common heart failure therapies (such as β-adrenergic blockade (propranolol), angiotensin-converting enzyme inhibition (captopril), or angiotensin receptor 1 blockade (losartan)), reversed sNRF effects, the following methods were used. CFs were transiently transfected with the α-SMA-luciferase vector and pcDNA3 control vector or pcDNA3-sNRF, then treated for 24 hours with TGF-β$_1$, ANP, and the angiotensin-converting enzyme inhibitor captopril (CAP) or the angiotensin receptor-1 blocker losartan (LOS).

Figure 1:
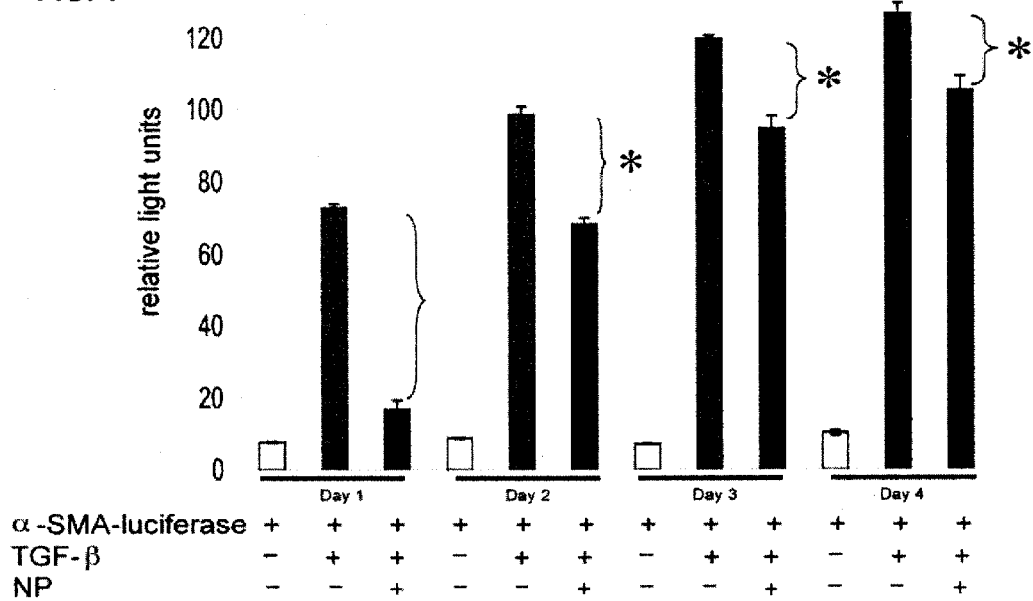
FIG. 1 is a bar graph showing that prolonged NP stimulation of CF cells causes NP resistance. Data represents mean±SE for 4 independent experiments, each performed in duplicate. *difference in luciferase expression between TGF-$β_1$ and TGF-$β_1$+NP compared today 1, $p<0.05$.
Figure 9:
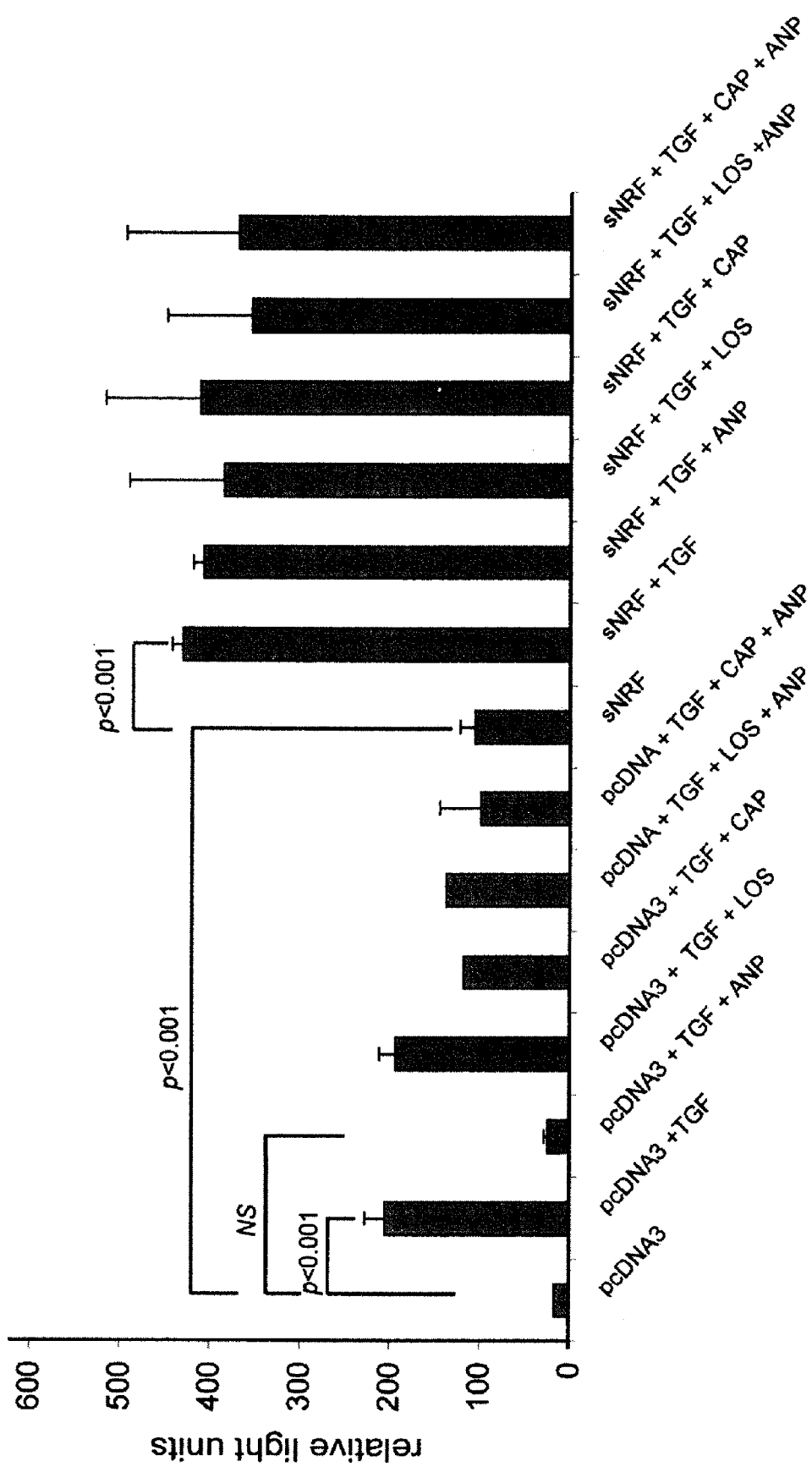
FIG. 9 is a bar graph showing that sNRF inhibits NP action and angiotensin-inhibiting drugs do not block sNRF effects. Data is mean±SEM and represents 6 separate experiments (except for LOS n=2).

As shown in FIG. 9, sNRF expression in untreated CFs significantly increased α-SMA-luciferase expression compared to non-sNRF expressing untreated cells. Furthermore, sNRF expression in TGF-β$_1$-treated cells increases α-SMA luciferase expression more than four-fold compared to TGF-β$_1$-treated control cells. sNRF expression significantly amplified reporter induction in both control and TGF-β$_1$-treated cells. NP treatment inhibits TGF-β$_1$-induced α-SMA-luciferase expression in cells that do not over-express sNRF (FIGS. 1 and 7). However, sNRF over-expression abolishes NPs' inhibitory effect. Angiotensin inhibition with either captopril or losartan had no significant inhibitory effect on this sNRF action (FIG. 7). In fact, in non-sNRF transfected cells, losartan appears to have a sNRF-like effect (losartan blocks NP-inhibition of TGF-β$_1$ induction of α-SMA-luciferase). β-adrenergic blockade also had no effect on sNRF action.

In summary, standard heart failure therapies appear to have little or no inhibitory effect on sNRF action. These data indicate that β-blockade or angiotensin inhibition will not be effective therapies against sNRF's deleterious action.

Example 12

Reducing the Biological Activity of sNRF

This example describes methods that can be used to reduce the biological activity of sNRF as a method of treating heart disease. Based on the observations described in Examples 4 and 5 (FIGS. A-D and 5A-B) showing that sNRF mRNA expression is elevated in heart disease, sNRF is a target for heart failure therapies designed to reduce or block sNRF action. Although particular methods of reducing sNRF activity by blocking expression with siRNA are described, one skilled in the art will appreciate that similar methods can be used with other agents that significantly decrease sNRF expression or activity, such as other inhibitory nucleic acid molecules.

As shown in the Examples above, sNRF expression inhibits NPs' beneficial actions, such as its ability to block the growth factor-induced differentiation of cardiac fibroblasts to myofibroblasts. The methods in this example provide methods of reducing sNRF expression using siRNA, thereby restoring NPs' beneficial effects in NP-resistant cells.

Primary fibroblast cultures can be obtained from human tissue derived from explanted heart from patients prior to orthotopic heart transplantation. As an alternative, human CFs can be purchased from ScienCell Research Laboratories (San Diego, Calif.). Non-cardiac failure human fibroblasts can be derived from discarded material from children and adults undergoing cardiac surgery. Post-mortem tissue from individuals without a cardiac history can also be obtained as a source of CFs. An additional source of heart tissue is myocardial plugs discarded after patients are placed on mechanical ventricular assist.

The neonatal rat CF culture protocol (Simpson, *Circ. Res.* 56(6):884-894, 1985), modified for human cell culture according to the method of Agocha et al. (*Cell Tissue Res.* 288(1):87-93, 1997), can be used to culture primary CF cells. The heart muscle is immediately minced and placed in ADS buffer containing 1.5 mg/ml trypsin (Gibco cat. #27250-018), collagenase (type IV, Sigma) and 1% DNase solution (2 mg/ml DNase type II in 150 mM NaCl) with serum neutralization. The collected cells are pre-incubated in media at 37° C. for 90 minutes to allow CF attachment to the bottom of culture dishes. Myocytes in the supernatant and a portion of the CFs are placed in RNA stat-60 (Iso-Tex Diagnostics, Inc.) for subsequent sNRF mRNA quantitation. The remaining CFs are either flash-frozen in liquid nitrogen and placed in −80° C. for future use, or incubated in plating media for 48 hours, divided into multi-well culture plates and grown to 50% confluency in DMEM with 10% FBS prior to transfection and/or subsequent experimental protocols. These cells can be used effectively for up to 9 passages. Experiments will be performed on passage 2 or 3 cells. To confirm that there is no relevant contamination of fibroblasts with endothelial cells, smooth muscle cells, or cardiac myocytes, cells will be stained for vimentin, for the absence of von Willebrand factor, α-SMA, and sarcomeric actin.

Small interfering (si)RNA molecules specific for sNRF can be generated as follows. The sNRF cDNA clone (GenBank Accession No. BX329044) contains a 215-nt sequence corresponding to intron 15 of the genomic NPRA sequence (nucleotides 1-215 of SEQ ID NO: 37) that is not present in the native NPRA cDNA. This sequence, therefore, presents a unique target for siRNA-directed sNRF knockdown that should have no substantial effect on full-length NPRA expression. Since single siRNA sequences may each have off-target effects or varying degrees of silencing, least two effective sNRF siRNAs, including "ON-TARGET plus" modified siRNAs thought to decrease off-target effects up to 90% (Dharmacon) are used. Sequences at the 5' end of the presumed sNRF 5'-UTR are targeted so as to avoid the intron 15-exon 16 splice acceptor site and the adjacent 5' branch point (usually ~35 nt upstream of the 3' end of the relevant intron), whose interaction with a sNRF-directed siRNA could modulate expression of the full-length NPRA mRNA. As a functional control for this possibility, quantitative RT-PCR can be used to measure native NPRA mRNA using a probe that is complementary to mRNA 5' of the sNRF sequence. In addition to specific control siRNAs, scrambled sNRF oligos or GFP siRNA can be used.

Particular exemplary siRNA molecules that can be used to silence sNRF expression include those shown in SEQ ID NO: 14, 16, 18, 20, 22, 24, 26, 28, 30 or 32 (as well as duplexes of these hybridized to their complementary sequences, such as those sequences shown in SEQ ID NO: 13, 15, 17, 19, 21, 23, 25, 27, 29, and 31, respectively).

To achieve high transfection efficiency, the transfection efficiency of several transient transfection reagents (HiPerFect, Quiagen; GeneEraser, Stratagene; FuGene 6, Roche; Lipofectin, Invitrogen) can be determined. Transfection efficiency can be determined using GAPDH siRNA (Dharmacon) and subsequent quantification of GAPDH mRNA.

Titration curves using each of the sNRF siRNA molecules can be constructed, since off-target effects are minimized at low siRNA concentrations. The titration curve can be constructed based on quantitative RT-PCR determinations of sNRF mRNA expression. The sNRF-specific primers shown in FIG. 2 ("a" and "b") will be use. As described above, two different siRNA sequences that produce at least a 50% reduction of sNRF mRNA expression when using at a maximum of 40-50 nM will be employed for subsequent methods.

Both commercial and patient-derived cells will be analyzed for α-SMA protein using Western blots probed with specific polyclonal antibody (FIG. 9) and sNRF mRNA expression. Untreated cells will likely have low levels of α-SMA. If fibroblasts cultured from failing myocardium contained increased α-SMA compared to cells derived from non-failing hearts, this would indicate their transdifferentiation into myofibroblasts. This is not impossible, since injured myocardium has increased α-SMA expression. It is more likely, however, that cultured fibroblasts will de-differentiate and express low amounts of α-SMA that are typical of unstimulated cells.

As shown in the Examples above, failing myocardium has elevated sNRF mRNA levels. This will be confirmed in cultured fibroblasts derived from failing heart compared to non-failing fibroblasts, as well as for cardiomyocytes in the supernatants obtained during CF tissue culture.

Using the methods described in Example 1, human CFs will be transfected with the α-SMA-luciferase vector with or without sNRF siRNA and treated with TGF-$\beta_1$ with or without NP, for up to 4 days. It is expected that a time-dependent increase in α-SMA-luciferase expression and sNRF mRNA concentration in the TGF-$\beta_1$+NP-treated cells, but not in the siRNA-transfected TGF-$\beta_1$+NP-treated cells, will be observed. This result would demonstrate that NP resistance is caused by sNRF.

To confirm this observation, and as an independent verification of the specificity of the siRNAs used, one of two pcDNA3 plasmid vectors that contain either 1) the sNRF open reading frame-alone or 2) a mutated sNRF 5'-UTR/intron-15 sequence that is not complementary to the effective sNRF siRNA(s) will be co-transfected. Since the sNRF siRNA targets the sNRF 5'-UTR (encoded by intron 15 of the NPRA gene), co-transfections of the sNRF plasmid (containing only the open reading frame) or the mutated sequence should both rescue the ability of prolonged NP exposure to desensitize NPRA. In the first rescue, prolonged NP exposure will result in progressively increased α-SMA-luciferase expression. In the second rescue, it is expected that over the 4-day period increasing α-SMA-luciferase expression and increasing sNRF mRNA levels in quantitative RT-PCR experiments will be observed.

If efficient sNRF siRNA oligomers cannot be designed from the 215-nt NPRA intron-15 sequence (nucleotides 1-215 of SEQ ID NO: 37), rapid amplification of 5' complementary DNA ends (5' RACE) can be used to delineate the 5' end of the sNRF mRNA. This will provide additional 5' sequence information, to which additional sNRF-specific siRNAs can be targeted using routine methods known in the art.

siRNA or other inhibitory molecules shown to be effective in vitro can be further tested in vivo, for example in a laboratory animal model for heart failure (see Example 16).

Example 13

Effect of sNRF on the TGF-$\beta_1$ Signaling Pathway

TGF-$\beta_1$ signaling plays a role in the development of cardiac hypertrophy and heart failure, and sNRF potentiates TGF-β₁'s ability to induce cardiac fibroblast differentiation. This example describes methods than can be used to determine whether this effect is due to inhibition of basal NPRA activity or through independent regulation of TGF-β₁ signaling itself, using NPRA-expressing and NPRA-deficient cells. Similar methods can be used to screen for compounds that decrease the sNRF-induced deleterious growth factor effects (such as TGF-β₁'s ability to induce cardiac fibroblast differentiation).

One explanation for the observation that sNRF potentiates TGF-β₁ activity is that sNRF-PKG association inhibits PKG action (perhaps by inhibiting nuclear translocation of PKG), thereby preventing PKG inhibition of thrombospondin transcription. As shown in FIG. 9, sNRF expression increases basal α-SMA expression and also significantly increases TGF-β₁-induced α-SMA expression compared to non-sNRF-expressing, untreated CFs. This example provides methods that can be used to determine if sNRF's TGF-β₁-potentiating effect is due to inhibition of basal NPRA activity or through a direct effect on the TGF-β₁ signaling system.

Commercial or patient-derived human CFs will be used as described in the Examples above. To determine if sNRF's potentiation of TGF-β₁ signaling is a direct effect that is independent of NPRA, NPRA gene expression will be decreased using NPRA siRNA. Multiple siRNA sequences can be evaluated (such as the exemplary siRNA duplex molecules shown in SEQ ID NOS: 13 and 14, SEQ ID NOS: 15 and 16, SEQ ID NOS: 17 and 18, SEQ ID NOS: 19 and 20, and SEQ ID NOS: 21 and 22). Transfection efficiency using GAPDH siRNA and optimal concentration will be determined as described in Example 12. NPRA protein expression will be assessed by Western immunoblotting using NPRA-specific antisera (ABCAM ab14356), and NPRA mRNA expression will be measured by quantitative RT-PCR.

NPRA-deficient cells are transfected with pcDNA3-sNRF or control vector before measurement of receptor activation. TGF-β₁ receptors initiate intracellular signal transduction by phosphorylation of members of the Smad protein family. Phospho-Smads 2 and 3 initiate transcriptional events after nuclear translocation. Therefore, following NPRA knockdown in pcDNA-sNRF-transfected cells, TGF-β₁-induced α-SMA luciferase and protein expression will be compared to cells expressing normal NPRA levels in addition to Smad phosphorylation and nuclear translocation.

In cells over-expressing sNRF, increased TGF-β₁-induced α-SMA expression in the presence of NPRA knockdown would support the conclusion that sNRF action is NPRA-independent. If this effect were due specifically to increased TGF-β₁ signaling, then Western immunoblots probed with anti-phospho-Smad (anti-Smad2-Signal Transduction Labs and anti-phospho-Smad2-Upstate Biotech.) would show increased Smad activation compared to cells not over-expressing sNRF.

If sNRF over-expression increases TGF-β₁ signaling through binding PKG and blocking PKG's inhibition of thrombospondin transcription, then sNRF over-expression in NPRA-silenced cells treated with TGF-β₁ may decrease intranuclear PKG observed using immunofluorescence microscopy (method described in Example 7) or decreased phosphorylation activity as demonstrated by in vitro PKG kinase activity assays. It is expected to observe increased thrombospondin mRNA and protein expression (anti-thrombospondin antibody, Abcam #ab2962) in sNRF over-expressing cells. The opposite would occur in sNRF-silenced and NPRA-silenced cells treated with TGF-β₁ (that is, increased nuclear PKG, increased in vitro PKG kinase activity, and decreased thrombospondin).

Example 14

Identification of Therapeutic Agents

This example provides a particular example of an in vitro assay that can be used to screen agents for their potential to treat a cardiovascular disorder, such as heart failure. For example, agents can be screened for their ability to increase the biological activity of NPRA/B, inhibit the biological activity of sNRF, decrease sNRF-induced deleterious growth factor effects (such as TGF-β₁'s ability to induce cardiac fibroblast differentiation) or combinations thereof, for example by increasing the sensitivity of NPRA/B to NPs. Agents identified via the disclosed assays can be useful, for example, in restoring or enhancing the beneficial effects of NPs, for example in treating a subject having a disease that results from decreased biological activity of NPR that results when the receptor becomes desensitized to the presence of NPs, such as cardiovascular disease. In addition, agents identified via the disclosed assays can be useful, for example, in decreasing deleterious growth factor effects, for example in treating a subject having a disease that results from sNRF-induced deleterious growth factor effects, such as cardiovascular disease.

Although particular examples are provided for screening, one skilled in the art will appreciate that variations to the disclosed method can be made, without affecting the assay. For example, other growth factors besides FGF or TGF-β can be used (such as epidermal growth factor (EGF), fibroblast growth factor (FGF), erythropoietin (EPO), growth hormone (GH), insulin-like growth factor, insulin, hematopoietic cell growth factor (HCGF), platelet-derived growth factor (PDGF), and vascular endothelial growth factor (VEGF)). In addition, other intracellular NPRA fragments can be used, such as sNRF$^{(806-1061)}$ (SEQ ID NO: 4), sNRF$^{(820-1061)}$ (SEQ ID NO: 40), or sNRF$^{(820-900)}$ (SEQ ID NO: 42).

As disclosed in the examples above, intracellular NPRA fragments (sNRF) that interfere with the association or binding between PKG and NPRA mimic the physiology of heart failure, for example by increasing cGMP levels in CFs. Therefore, screening assays that utilize sNRF can be used to identify and analyze agents for their ability to increase the biological activity of NPR or to decrease the biological activity of sNRF. In particular examples, agents identified via the disclosed assays can be useful in increasing the sensitivity of a desensitized NPR to NPs, for example in treating a subject having (or at risk for developing) cardiovascular disease. Assays for testing the effectiveness of the identified agents, are discussed below.

It is also disclosed in the examples above, that sNRF potentiates deleterious growth factor effects, such as cardiac fibroblast differentiation and expression of collagen, extracellular matrix, and α-SMA. Therefore, screening assays that utilize sNRF can be used to identify and analyze agents for their ability to decrease the biological activity of sNRF. In particular examples, agents identified via the disclosed assays can be useful in decreasing sNRF-induced potentiation of growth factor effects on cardiovascular disease, for example in treating a subject having (or at risk for developing) cardiovascular disease. Assays for testing the effectiveness of the identified agents, are discussed below.

Exemplary agents that can be screened include, but are not limited to, any peptide or non-peptide composition in a purified or non-purified form, such as peptides made of D- and/or L-configuration amino acids (in, for example, the form of random peptide libraries; see Lam et al., *Nature* 354:82-4, 1991), phosphopeptides (such as in the form of random or partially degenerate, directed phosphopeptide libraries; see, for example, Songyang et al., *Cell* 72:767-78, 1993), antibodies, nucleic acid molecules (such as RNAi molecules, for example siRNAs) and small or large organic or inorganic molecules. A test agent can also include a complex mixture or "cocktail" of molecules.

Briefly, in one example the method includes cellular expression of α-SMA-luciferase and sNRF in neonatal rat cardiac fibroblasts (sNRF-o-blasts). A TGF-$\beta_1$-induced signal is quenched after NP treatment of primary cultures of control cells (FIG. 9). In this sNRF-o-blast system, sNRF expression reverses NP-induced inhibition of the reporter signal, a model that mimics NP resistance in human heart failure. Using this assay in transiently transfected cells, a library of small molecules can be screened for lead drugs that restore NP-induced inhibition of TGF-$\beta_1$-stimulated luciferase expression.

Test agents can be screened for their ability to reverse the effects of recombinant sNRF molecules that interfere with the PKG-NPRA association. Primary CF cells are prepared using routine methods, for example as described in Example 7. However, one skilled in the art will recognize that other CF cells can be used, and other methods of preparing CF cells can be used. The CF cells are transfected with a vector that includes an α-SMA promoter operably linked to a reporter sequence. α-SMA promoter sequences are known. The α-SMA promoter sequence can be introduced upstream of luciferase, using the p-luc vector that includes that luciferase reporter sequence (for example see Liu et al., *J. Biol. Chem.* 278:48004-11, 2003). The resulting vector is transfected into CF cells using routine methods.

In addition, the CF cells include a recombinant sNRF protein that can bind PKG, such as those shown in SEQ ID NOS: 4, 6, 38, 40 or 42. sNRF can include other elements, such as a FLAG tag. In one example, sNRF (such as SEQ ID NO: 4, 6, 38, 40 or 42) is operably linked to a promoter, and can be part of a vector. In a particular example, one vector is used that includes both the promoter-sNRF and α-SMA promoter-luciferase sequences.

CF cells that include a recombinant sNRF that can bind PKG and a recombinant α-SMA promoter sequence operably linked to luciferase (or other reporter sequence), are incubated with 10 ng/ml FGF or 5 ng/ml TGF-β, and 100 nM ANP for 15 minutes at 37° C. Simultaneously, before, or after incubation with ANP, cells are contacted with one or more test agents. In particular examples, the CF cells are present in a multi-well plate, such as a 12-, 24-, 96-, 384-, or 1536-well plate. Such plating permits high-throughput screening.

Particular examples of controls that can be included are:
(1) CF cells that include a recombinant α-SMA promoter sequence operably linked to luciferase (or other reporter sequence) incubated with growth factor, but not ANP or the test agent. Such conditions should result in a positive signal from the reporter.
(2) CF cells that include a recombinant α-SMA promoter sequence operably linked to luciferase (or other reporter sequence) incubated with growth factor and ANP, but not the test agent. Such conditions should result in a negative signal from the reporter.
(3) CF cells that include a recombinant sNRF that can bind PKG (such as SEQ ID NO: 4, 6, 38, 40 or 42) and a recombinant α-SMA promoter sequence operably linked to luciferase (or other reporter sequence) incubated with growth factor and ANP, but not the test agent. Such conditions should result in a positive signal from the reporter.

Following incubation with the desired agents, the signal generated from the reporter is measured. For example, the luciferace signal generated from the cells can be detected using a spectrophotometer. Detectable luciferase (or other reporter) signal should be detected in controls (1) and (3). However, decreased or even undetectable luciferase (or other reporter) signal should be observed in control (2).

Test agents having similar luciferase (or other reporter) signal to that in controls (1) and (3) are not expected to enhance the sensitivity of NPR for NP ligands. In contrast, test agents having similar luciferase (or other reporter) signal to that in control (2), or that have significantly less than controls (1) and (3), may have the ability to enhance the sensitivity of NPR for NP ligands, and thus may be able to treat cardiovascular disease. Such agents can be selected for further examination. For example, test agents identified using this assay can be screened for their ability to bind PKG (see Example 7) or decrease sNRF-induced deleterious growth factor effects (for example see Example 10 and 13), and for their ability to treat cardiovascular disease in an animal model (see Example 16). Further more, such agents can be used to treat a subject having cardiovascular disease (see Example 18).

Example 15

Molecules for Disruption of sNRF Expression

This example describes siRNA, antisense, ribozyme, microRNA, and triple helix molecules that can be used to reduce or disrupt expression of sNRF, thereby decreasing the biological activity of sNRF. Such agents are useful for treating heart failure, for example preventing heart failure in a subject having increased risk for developing heart failure. Techniques for the production and use of such molecules are well known to those of skill in the art. For example, nucleic acid sequences can synthesized by use of an automated DNA synthesizer. Methods for using these molecules are described in Example 18.

The amount of siRNA, antisense, ribozyme, microRNA, or triple helix molecule that is effective in the treatment of a particular heart disease or condition (the therapeutically effective amount) depends on the nature of the disease or condition, and can be determined by standard clinical techniques. For example, it can be useful to use compositions to achieve sustained release of such nucleic acid molecules. In another example, liposomes containing the desired therapeutic molecule are targeted via antibodies to specific cells.

In particular examples, at least one of the particularly disclosed siRNA molecules (SEQ ID NOS: 14, 16, 18, 20, 22, 24, 26, 28, 30 or 32), alone or hybridized to its respective sense sequence (SEQ ID NOS: 15, 17, 19, 21, 23, 25, 27, 29, and 31, respectively, wherein the hybridized duplex is administered), or combinations thereof, is administered to a subject to treat heart failure. In one example, the amount of disclosed siRNA, antisense, or ribozyme RNA administered (for example in a single dose) is 1-10 mg nucleic acid molecule/kg of subject, such as 1-5 mg/kg, or 3-7 mg/kg. In particular examples, the inhibitory RNA molecule is administered intravenously. In some example, the inhibitory RNA molecule is delivered to a cell, such as a cell in a subject, using a viral vector. If desired, cells can be transfected with the desired inhibitory RNA molecule, and the cells subsequently delivered to the subject using methods known in the art.

siRNA Molecules siRNA molecules can be used to decrease or inhibit expression of sNRF, for example to decrease the ability of a pathogen to infect a cell, such as infection by an enveloped RNA virus. Exemplary siRNA compounds are provided herein, such as the exemplary siRNA antisense molecules shown in SEQ ID NOS: 14, 16, 18, 20, 22, 24, 26, 28, 30 and 32. One skilled in the art will appreciate that these antisense molecules can by hybridized to their sense strand (SEQ ID NOS: 15, 17, 19, 21, 23, 25, 27, 29, and 31, respectively), and the resulting duplex used as the therapeutic molecule. However, the disclosure is not limited to these particular siRNA molecules. Based on the disclosed sNRF sequences (such as intron 15 of NPRA, nucleotides 1-215 of SEQ ID NO: 37), one skilled in the art can generate other siRNA molecules using known methods. For example, siRNA sequences that recognize sNRF sequences can be designed and prepared by commercial entities, such as Sequitur, Inc. (Natick, Mass.) and Dharmacon (Lafayette, Colo.).

This disclosure is not limited to siRNA compounds of a particular length. A siRNA molecule specific for sNRF can be any length, such as at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, or at least 30 nucleotides.

Using the methods described herein (for example, see Example 18), siRNA compounds can be used to treat heart failure, prevent future heart failure, or combinations thereof. For example, an siRNA compound shown in any of SEQ ID NOS: 14, 16, 18, 20, 22, 24, 26, 28, 30 and 32 is incubated with its reverse complement (SEQ ID NOS: 15, 17, 19, 21, 23, 25, 27, 29, and 31, respectively), allowing hybridization of the two molecules. In particular examples, two or more, such as three or more, or four or more, siRNA compounds are introduced into a cell. For example, the duplex molecule is contacted with a cell, such as a cell of a subject in whom relief of symptoms associated with heart failure is desired, under conditions that allow the duplex to enter the cell. In particular examples, the duplex is administered ex vivo or in vitro to a cell, or administered directly to a subject. In another example, an siRNA is part of a vector, and the vector administered ex vivo or in vitro to a cell, or administered directly to a subject. In one example, the vector is the pSilencer™ 4.1-CMV vector (Ambion, Austin, Tex.).

Antisense Methods

Antisense oligonucleotides can be designed and generated using methods known in the art. For example, a sNRF genomic or mRNA sequence is examined (such as nucleotides 1-215 of SEQ ID NO: 37). Regions of the sequence containing multiple repeats, such as TTTTTTTT, are not as desirable because they will lack specificity. Several different regions can be chosen. Of those, antisense oligonucleotides are selected by the following characteristics: those having the best conformation in solution; those optimized for hybridization characteristics; and those having less potential to form secondary structures. Antisense molecules having a propensity to generate secondary structures are less desirable.

An antisense molecule that recognizes sNRF includes a sequence complementary to at least a portion of a sNRF RNA transcript. However, absolute complementarity is not required. An antisense sequence can be complementary to at least a portion of an RNA, meaning a sequence having sufficient complementarily to be able to hybridize with the RNA, forming a stable duplex; in the case of double-stranded antisense nucleic acids, a single strand of the duplex DNA may thus be tested, or triplex formation can be assayed. The ability to hybridize depends on the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In a particular example, an antisense molecule that is specific for sNRF includes at least 80% sequence identity, such as at least 90% sequence identity, to at least a fragment of a sNRF gene sequence, such as nucleotides 1-215 of SEQ ID NO: 37. In one example, the relative ability of an antisense molecule to bind to its complementary nucleic acid sequence is compared by determining the $T_m$ of a hybridization complex of the antisense molecule and its complementary strand. The higher the $T_m$ the greater the strength of the binding of the hybridized strands.

Plasmids or vectors including antisense sequences that recognize sNRF can be generated using standard methods. For example, cDNA fragments or variants coding for a sNRF protein involved in infection are PCR amplified, for example using Pfu DNA polymerase (Stratagene). The resulting sequence is cloned in antisense orientation a vector, such as pcDNA vectors (InVitrogen, Carlsbad, Calif.). The nucleotide sequence and orientation of the insert can be confirmed by sequencing using a Sequenase kit (Amersham Pharmacia Biotech). Such vectors can be administered to a cell in a therapeutic amount, such as administered to a subject, to decrease one or more symptoms of heart failure.

Generally, the term "antisense" refers to a nucleic acid molecule capable of hybridizing to a portion of a sNRF RNA sequence (such as mRNA) by virtue of some sequence complementarity. The antisense nucleic acids disclosed herein can be oligonucleotides that are double-stranded or single-stranded, RNA or DNA or a modification or derivative thereof, which can be directly administered to a cell (for example by administering the antisense molecule to the subject), or which can be produced intracellularly by transcription of exogenous, introduced sequences (for example by administering to the subject a vector that includes the antisense molecule under control of a promoter).

Antisense nucleic acids are polynucleotides, for example nucleic acid molecules that are at least 6 nucleotides in length, at least 10 nucleotides, at least 15 nucleotides, at least 20 nucleotides, at least 40 nucleotides, at least 100 nucleotides, at least 200 nucleotides, such as 6 to 100 nucleotides. However, antisense molecules can be much longer. In particular examples, the nucleotide is modified at one or more base moiety, sugar moiety, or phosphate backbone (or combinations thereof), and can include other appending groups such as peptides, or agents facilitating transport across the cell membrane (Letsinger et al., *Proc. Natl. Acad. Sci. USA* 1989, 86:6553-6; Lemaitre et al., *Proc. Natl. Acad. Sci. USA* 1987, 84:648-52; WO 88/09810) or blood-brain barrier (WO 89/10134), hybridization triggered cleavage agents (Krol et al., *BioTechniques* 1988, 6:958-76) or intercalating agents (Zon, *Pharm. Res.* 5:539-49, 1988).

Examples of modified base moieties include, but are not limited to: 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl)uracil, and 2,6-diaminopurine.

Examples of modified sugar moieties include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In a particular example, an antisense molecule is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625-41, 1987). The oligonucleotide can be conjugated to another molecule, such as a peptide, hybridization triggered cross-linking agent, transport agent, or hybridization-triggered cleavage agent. Oligonucleotides can include a targeting moiety that enhances uptake of the molecule by host cells. The targeting moiety can be a specific binding molecule, such as an antibody or fragment thereof that recognizes a molecule present on the surface of the host cell.

In a specific example, antisense molecules that recognize a sNRF nucleic acid molecule, include a catalytic RNA or a ribozyme (for example see WO 90/11364; WO 95/06764; and Sarver et al., *Science* 247:1222-5, 1990). Conjugates of antisense with a metal complex, such as terpyridylCu (II), capable of mediating mRNA hydrolysis, are described in Bashkin et al. (*Appl. Biochem Biotechnol.* 54:43-56, 1995). In one example, the antisense nucleotide is a 2'-0-methylribonucleotide (Inoue et al., *Nucl. Acids Res.* 15:6131-48, 1987), or a chimeric RNA-DNA analogue (Inoue et al., *FEBS Lett.* 215:327-30, 1987).

Ribozymes

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Methods of using ribozymes to decrease or inhibit RNA expression are known in the art (for example see Kashani-Sabet, *J. Investig. Dermatol. Symp. Proc.*, 7:76-78, 2002).

Ribozyme molecules include one or more sequences complementary to a sNRF genomic or mRNA sequence (such as complementary to nucleotides 1-215 of SEQ ID NO: 37) and include the well-known catalytic sequence responsible for mRNA cleavage (see U.S. Pat. No. 5,093,246, herein incorporated by reference).

Methods of designing and generating ribozyme molecules are known in the art. Briefly, specific ribozyme cleavage sites within a sNRF RNA target (such as nucleotides 1-215 of SEQ ID NO: 37) are identified by scanning the RNA sequence for ribozyme cleavage sites that include: GUA, GUU and GUC. Once identified, RNA sequences of between 15 and 50 ribonucleotides (such as at least 20 ribonucleotides, at least 40 ribonucleotides, for example 15-40, or 20-30 ribonucleotides) corresponding to the region of sNRF containing the cleavage site can be evaluated for predicted structural features, such as secondary structure, that may render the oligonucleotide sequence unsuitable. The suitability of candidate targets cam also be evaluated by testing their accessibility to hybridization with complementary oligonucleotides, using ribonuclease protection assays.

In particular examples, ribozymes are administered directly to a subject. In another example, a ribozyme is encoded on an expression vector, from which the ribozyme is synthesized in a cell (as in WO 9523225, and Beigelman et al. *Nucl. Acids Res.* 1995, 23:4434-42). Such a cell or the vector can be administered to a subject.

In a specific example, a vector that contains a ribozyme gene directed against sNRF, placed behind a promoter (such as an inducible promoter), is transfected into the cells of a subject, for example a subject having or susceptible to developing heart failure. Expression of this vector in a cell will decrease or inhibit sNRF RNA expression in the cell. In one example, the vector is the pSilencer™ 4.1-CMV vector (Ambion).

In a particular example, a vector includes self-cleaving tandem ribozymes (for example, 5 ribozymes encoded on a single RNA transcript). Once the tandem hammerhead transcript is synthesized, it recognizes ribozyme cleavage sites in cis within the newly synthesized transcript identical to the ribozyme target site on the cell's endogenously expressed mRNA. The tandem ribozyme then cleaves itself, liberating free ribozymes to cleave the target mRNA in the cell.

MicroRNAs

MicroRNAs (miRs) that recognize a sNRF mRNA, can be used to decrease the amount of such mRNAs in a cell. miRNAs silence at the post-transcriptional level by virtue of their sequence complementarity to target mRNAs. In particular examples, miRs are about 18-26 nucleotides in length, such as 21-26 nucleotides, such as at least 18 nucleotides. Animal miRNAs are generally thought to recognize their mRNA targets by incomplete base-pairing, leading to translational inhibition of the target.

Methods of generating or identifying microRNAs are known in the art (for example see Lagos-Quintana et al., *Science,* 294:853-8, 2001; Lagos-Quintana et al., *Curr. Biol.* 12:735-9, 2002; and Lagos-Quintana et al., *RNA* 9:175-9, 2003).

Triple Helix Molecules

Nucleic acid molecules used in triplex helix formation for sNRF are ideally single stranded and composed of deoxynucleotides. The base composition of these oligonucleotides is designed to promote triple helix formation via Hoogsteen base pairing rules, which generally require sizeable stretches of either purines or pyrimidines to be present on one strand of a duplex. Nucleotide sequences can be pyrimidine-based, which will result in TAT and CGC+ triplets across the three associated strands of the resulting triple helix. The pyrimidine-rich molecules provide base complementarity to a purine-rich region of a single strand of the duplex in a parallel orientation to that strand. In addition, nucleic acid molecules can be chosen that are purine-rich, for example contain a stretch of guanidine residues. These molecules will form a triple helix with a DNA duplex that is rich in GC pairs, in which the majority of the purine residues are located on a single strand of the targeted duplex, resulting in GGC triplets across the three strands in the triplex.

Alternatively, sNRF sequences targeted for triple helix formation are increased by creating "switchback" nucleic acid molecule. Switchback molecules are synthesized in an alternating 5'-3', 3'-5' manner, such that they base pair with one strand of a duplex first and then the other, eliminating the necessity for a sizeable stretch of either purines or pyrimidines to be present on one strand of a duplex.

sNRF inhibitory molecules shown to be effective in vitro can be further tested in vivo, for example in a laboratory animal model for heart failure (see Example 16).

Example 16

In vivo Testing of Agents

This example describes methods that can be used to test agents described in Example 14 or 15, for their ability to increase the biological activity of NPR (such as NPRA) in vivo, to decrease growth factor deleterious effects, or both, for example by decreasing the biological activity of sNRF. Although particular methods are provided, one skilled in the art that other methods can be used, such as different animals, different modes of administration, and so forth.

The ability of an agent, such as those identified using the methods provided in Example 14 or the sNRF inhibitors disclosed in Example 15, or combinations thereof, can be assessed in animal models. For example, an animal model of cardiovascular disease can be administered the selected agent, and the effects on cardiovascular disease determined.

Such animal models are known in the art. For example, Kai et al. (*Hypertens Res.* 28:483-90, 2005) disclose Wistar rats with a suprarenal aortic constriction (AC) can be used as a model of cardiac hypertrophy, and Okuda et al. (*Hypertens Res.* 28:431-8, 2005) disclose that administration of isoproterenol (ISP) at 300 mg/kg into male rats can produce progressive heart failure. In addition, Patel et al. (*Am. J. Physiol. Heart Circ. Physiol.* 289:H777-84, 2005, herein incorporated by reference) disclose transgenic mice that have cardiomyocyte-specific expression of a dominant negative mutation (HCAT C893A) in the NPRA receptor but no expression of the mutant receptor in the CF population. Thus the receptors in CFs in this model are likely to have dysregulated NPRA. Any of these animal models can be used to analyze the effects of one or more test agents on their ability to increase the activity of NPR (such as NPRA), to decrease growth factor deleterious effects, or both, for example to treat cardiovascular disease. Animals of any species, including, but not limited to, mice, rats, rabbits, guinea pigs, pigs, micro-pigs, goats, and non-human primates, such as baboons, monkeys, and chimpanzees, can be used.

In addition, such animal models can be used to determine the $LD_{50}$ and the $ED_{50}$ in animal subjects, and such data can be used to determine the in vivo efficacy of potential agents.

The mammal is administered one or more agents identified in the examples above, alone or in combination with other therapeutic agents. The amount of agent administered, and the mode of administration, can be determined by skilled practitioners. In some examples, several different doses of the potential therapeutic agent can be administered via several different routes to different test subjects, to identify optimal dose ranges and modes of administration. Subsequent to the treatment, animals are observed for decreases in signs and symptoms associated with cardiovascular disease, such as disease that results from desensitization of NPR for NPs (for example heart failure). Animal subjects can be anesthetized prior to such treatments and evaluations.

In a specific example, sNRF siRNA (0.1-10 mg/kg), such as one or more of the exemplary siRNA duplex molecules shown in SEQ ID NOS: 14, 16, 18, 20, 22, 24, 26, 28, 30, or 32 (or a duplex hybridized to its complement), is administered to Wistar rats with a suprarenal aortic constriction (AC) via intravenous administration. In some examples, the siRNA is administered before the rat receives the suprarenal AC, to determine if the siRNA can reduce the effects of suprarenal AC (for example to function as a prophylactic).

In animal models, NPR function can assessed by measuring the circulating levels or urinary levels of cGMP in response to NP infusion. A typical bioassay of NPR function is to measure changes in forearm vascular resistance in response to NP infusion. Other common bioassays can be the urine output response to NP infusion. In animal models an agent may increase the activity of NPR (such as desensitized NPR) when treatment of the animal with the agent results in the typical response of the animal as if the NPR is not desensitized. Such an animal might have normalized blood pressure, increased urine output, suppression of numerous neuroendocrine markers of heart failure such as angiotensin, aldosterone, endothelin, renin, the sympathetic nervous system, or other growth factors, combing programmed cell death (apoptosis), decreased cardiac fibrosis, decrease in cardiac filling pressures, improvement of cardiac output, and in general diminution of the typical signs and symptoms of cardiovascular disease.

A decrease in the symptoms associated with cardiovascular disease that results from desensitization of NPR for NPs, in the presence of the agent provides evidence that the agent is a therapeutic agent that can be used to increase the biological activity of NPR or decrease growth factor (such as FGF and TGFβ1) deleterious effects, and therefore can be used to treat cardiovascular disease.

Example 17

Identification of Subjects that Could Benefit from Therapy

This example describes methods that can be used to screen a subject to determine if they have cardiovascular disease, or have an increased risk of developing cardiovascular disease. One skilled in the art will appreciate that other methods can be used, and that these methods are merely exemplary to provide guidance as to particular examples that can be used.

Generally, the method includes (if not already known) performing one or more diagnostic assays that are indicative of cardiovascular disease, such as heart failure. The most straight forward method of defining those with cardiovascular disease is define subjects based on the New York Heart classification of heart failure. Physical examination will reveal typical signs and symptoms of heart failure. Measurement of NPs will reveal patients with cardiovascular disease who are likely to benefit from the presence of agents that promote NPR PKG interaction, reduce deleterious growth factor effects, for example agents that decrease expression or activity of sNRF. Those with high circulating levels of NPs (>50-100 pg/ml) or increased serum cGMP (>8 pg/ml) may benefit from treatment.

In one example, the method includes analyzing a sample obtained from the subject, such as a blood sample (or fraction thereof). Serum or other blood fractions can be prepared in the conventional manner. For example, the levels of cGMP, ANP, BNP, triglycerides, cholesterol, can be determined using routine methods. Elevated levels of cGMP, ANP, BNP, or C-reactive protein, can indicate the presence of cardiovascular disease, while elevated levels of triglycerides or cholesterol can indicate the presence of cardiovascular disease or an increased risk of developing cardiovascular disease in the future.

In a particular example, the subject is subjected to a stress test.

In another example, the subject is subjected to an angiogram.

Subjects found to have cardiovascular disease, or have an increased risk of developing cardiovascular disease, can be administered the agents identified using the methods disclosed herein (see Example 18).

Example 18

Treatment of Subjects

This example describes methods that can be used to treat a subject having a heart disease (such as heart failure), or having an increased risk of developing heart disease in the future, by administration of one or more of the agents that decrease the biological activity of sNRF (such as siRNAs, see Example 15), or one or more agents identified using the methods disclosed herein (for example see Example 14). For example, the disclosed methods can be used to increase the sensitivity of an NPR for NP ligands (such as ANP) or decrease or inhibit the deleterious effects of growth factor action, such as the effects of TGFβ1 or FGF, for example to treat or reduce the symptoms of cardiovascular disease. For example, the disclosed methods can be used to. Such a therapy can be used alone, or in combination with other therapies (such as administration of a statin or anti-coagulant).

In particular examples, the method includes screening a subject having or thought to have (or be an increased risk of developing) cardiovascular disease, to identify those subjects that can benefit from administration of the therapeutic agents disclosed herein. As described in Example 17, subjects of an unknown cardiovascular disease status can be examined to determine if they have cardiovascular disease, or have an increased risk of developing cardiovascular disease. Subjects found to (or known to) have cardiovascular disease, or have an increased risk of developing cardiovascular disease, are selected to receive one or more agents disclosed herein.

As described in Example 14, screening methods can be used to identify agents that increase the activity of NPR or decrease growth factor (such as FGF and TGFβ1) deleterious effects. These agents, such as antibodies, peptides, nucleic acid molecules, organic or inorganic compounds, as well as the RNAi molecules described in Example 15, can be administered to a subject in a therapeutically effective amount to treat heart disease. Therefore, those agents can be administered to a subject having or at risk for developing cardiovascular disease at a therapeutically effective dose, thereby relieving the symptoms associated with cardiovascular disease or to prevent cardiovascular disease. Such agents can also be administered with other therapeutic agents, such as statins or anti-coagulants. By increasing the activity of NPRA/B, decreasing the activity of sNRF, decreasing growth factor (such as FGF and TGFβ1) deleterious effects, or combinations thereof, for example by increasing the sensitivity of NPRA/B for NP (such as ANP), the subject can take advantage of the naturally high levels of NPs that occur during cardiovascular disease (such as heart failure) and thereby capitalize on the "natural defenses" provided by NPs against cardiovascular disease.

The subject can be administered a therapeutic amount of one or more of the agents identified using the methods disclosed herein. The agents can be administered at doses of 1 µg/kg body weight to about 1 mg/kg body weight per dose, such as 1 µg/kg body weight –100 µg/kg body weight per dose, 100 µg/kg body weight –500 µg/kg body weight per dose, or 500 µg/kg body weight –1000 µg/kg body weight per dose. However, the particular dose can be determined by a skilled clinician. The agent can be administered in several doses, for example continuously, daily, weekly, or monthly.

Increasing the activity of NPRA/B need not result in 100% of native of NPRA/B function (for example 100% NPR resensitization), nor 100% inhibition of deleterious growth factor actions, nor treatment of 100% of the symptoms associated with the cardiovascular disease.

Example 15 describes molecules that decrease the biological activity of sNRF (such as decrease or inhibit the expression of sNRF mRNA). Such agents can be administered to a subject in a therapeutically effective amount that decreases the biological activity of sNRF. When the activity of sNRF is decreased, for example by prematurely downregulating their protein or nucleic acid molecule levels, a reduction in one or more symptoms associated with heart failure is achieved. For example, antisense oligonucleotides, ribozymes, miRs, siRNA, and triple helix molecules that recognize a nucleic acid that encodes sNRF can therefore be used to disrupt cellular expression of sNRF. The disclosed antisense, ribozyme, triple helix, miRs, and siRNA molecules (for example at a concentration of 1-100 mg nucleic acid molecule/kg of subject, such as 1-10 mg/kg, 1-20 mg/kg, 10-50 mg/kg, or 40-80 mg/kg) can be administered to a subject alone, or in combination with other agents, such as a pharmaceutical carrier, other therapeutic agents (such as agents used to treat heart disease, such as statins and anti-coagulants), or combinations thereof. In one example, the subject is a mammal, such as mice, non-human primates, and humans.

In one example, an siRNA, ribozyme, triple helix, miR, or antisense molecule specific for sNRF is part of a vector, and the vector administered ex vivo or in vitro to a cell, or administered directly to a subject. For example, a U6 promoter that controls the expression of 21 nucleotides, followed by a stem-loop of 8 bp, followed by an additional complementary 21 bp that anneals to the first 21 nucleotides transcribed. The 21 nucleotide sequences are the siRNA that recognize sNRF (such as SEQ ID NO: 14, 16, 18, 20, 22, 24, 26, 28, 30 or 32). Transcription is halted using a stretch of 5 T's in the plasmid immediately downstream of the last desired transcribed nucleotide. In another example, the vector is the pSilencer™ 4.1-CMV vector (Ambion).

In particular examples, a subject susceptible to or suffering from heart failure, wherein decreased symptoms associated with heart failure is desired, is treated with a therapeutically effective amount of antisense, ribozyme, triple helix, miR, or siRNA molecule (or combinations thereof) that recognizes a sNRF nucleic acid sequence (for example one that is complementary to at least 20 contiguous nucleotides, such as at least 21 contiguous nucleotides, of nucleotides 1-215 of SEQ ID NO: 37). Similarly, other agents, such as an agent that specifically recognizes and interacts with (such as binds to) a sNRF protein, thereby decreasing the ability of the sNRF protein to interfere with PKG-NPR binding, decreasing growth factor deleterious effects, or both, can also be used to treat heart failure.

After the agent has produced an effect (decreased symptoms associated with heart failure), for example after 24-48 hours, the subject can be monitored for symptoms associated with heart failure.

The mode of administration can be any used in the art, such as those described in Example 19. The amount of agent administered to the subject can be determined by a clinician, and may depend on the particular subject treated. Specific exemplary amounts are provided herein (but the disclosure is not limited to such doses).

Example 19

Pharmaceutical Compositions and Modes of Administration

This example provides methods and pharmaceutical compositions that can be used to administer a therapeutic agent disclosed herein (alone or in combination with other therapeutic agents), such as those that can increase the biological activity of NPRA or NPRB, decrease growth factor deleterious effects, or combinations thereof. Such agents include those identified using the methods described in Example 14 and the RNAi molecules described in Example 15.

Administration of such compositions to a subject can begin whenever treatment of symptoms associated with cardiovascular disease associated with decreased NPRA biological activity (such as desensitization of NPRA to ANP) or associated with insufficient sNRF-induced potentiation of deleterious growth factor effects, is desired. While compositions that include such therapeutic agents are typically be used to treat human subjects, they can also be used to treat other vertebrates such as other primates, farm animals such as swine, cattle and poultry, and sport animals and pets such as horses, dogs and cats.

The pharmaceutical compositions that include a therapeutic agent (for example see Examples 14 and 15) that can increase the biological activity of NPRA or NPRB, decrease the biological activity of sNRF, reduce sNRF-induced potentiation of deleterious growth factor effects, or combinations thereof, can be formulated in unit dosage form, suitable for individual administration of precise dosages. A therapeutically effective amount of such agents can be administered in a single dose, or in multiple doses, for example daily, during a course of treatment. Compositions that include such agents can be administered whenever the effect (such as decreased symptoms of cardiovascular disease) is desired. A time-release formulation can also be utilized.

A therapeutically effective amount of a composition that includes the therapeutic agent can be administered as a single pulse dose, as a bolus dose, or as pulse doses administered over time. In specific, non-limiting examples, pulse doses of compositions that include the agent are administered during the course of a day, during the course of a week, or during the course of a month.

The therapeutically effective amount of a composition including the therapeutic agent can depend on the molecule utilized, the subject being treated, the severity and type of the affliction, and the manner of administration, and should be decided according to the judgment of the practitioner and each subject's circumstances. Therapeutically effective amounts of compositions that include the therapeutic agent are those that restore function to a desensitized NPRA or NPRB by an amount that decreases one or more symptoms of cardiovascular disease, an amount that increases the sensitivity of NPRA or NPRB for ANP or BNP (for example an increase of at least 20% or at least 50%), those that reduce sNRF-induced potentiation of deleterious growth factor effects, or combinations thereof. In vitro assays can be employed to identify optimal dosage ranges. Effective doses can be extrapolated from dose-response curves derived from in vitro or animal model test systems. For example, a therapeutically effective amount of the therapeutic agent can vary from about 0.001 µg per kilogram (kg) body weight to about 20 mg per kg body weight, such as about 1 µg to about 5 mg per kg body weight, about 2 µg to about 0.5 mg per kg body weight, about 1 µg to about 50 µg per kg body weight, about 10 µg to about 100 µg per kg body weight, or about 5 µg to about 1 mg per kg body weight. The exact dose is readily determined by one of skill in the art based on the potency of the specific compound utilized, the age, weight, sex and physiological condition of the subject.

The compositions or pharmaceutical compositions can be administered by any route, including intravenous, intraperitoneal, subcutaneous, sublingual, transdermal, intramuscular, oral, topical, transmucosal, vaginal, nasal, rectal, by pulmonary inhalation, or combinations thereof. Compositions useful in the disclosure may conveniently be provided in the form of formulations suitable for parenteral (including intravenous, intramuscular and subcutaneous), nasal, topical, or oral administration.

In some examples, compositions that include the therapeutic agent are administered in combination with (such as before, during, or following) a therapeutically effective amount of one or more other therapeutic agents, in a single composition or solution for administration together. In other cases, it may be more advantageous to administer the additional agent separately from the therapeutic agent identified using the methods disclosed herein. Compositions that include the therapeutic agent can be administered simultaneously with the additional agent(s), or administered sequentially. In one example, the other therapeutic agent is a statin, an anti-coagulant, or other agents that alleviate symptoms associated with cardiovascular disease (or risk of developing cardiovascular disease).

Therapeutic compositions can be provided as parenteral compositions, such as for injection or infusion. Such compositions are formulated generally by mixing the identified therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a the identified therapeutic agent can be suspended in an aqueous carrier, for example, in an isotonic buffer solution at a pH of about 3.0 to about 8.0, such as at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

A form of repository or "depot" slow release preparation can be used so that therapeutically effective amounts of the preparation are delivered into the bloodstream over many hours or days following transdermal injection or delivery. Such long acting formulations can be administered by implantation (for example subcutaneously or intramuscularly) or by intramuscular injection. The compounds can be formulated with suitable polymeric or hydrophobic materials (for example as an emulsion in an acceptable oil) or ion exchange resins, or as sparingly soluble derivatives, for example, as a sparingly soluble salt.

Pharmaceutical compositions that include the identified therapeutic agent as an active ingredient can be formulated with an appropriate solid or liquid carrier, depending upon the particular mode of administration chosen. The product can be shaped into the desired formulation. In one example, the carrier is a parenteral carrier, such as a solution that is isotonic with the blood of the recipient. Examples of such carrier vehicles include water, saline, Ringer's solution, glycerol and dextrose solution. Non-aqueous vehicles such as fixed oils and ethyl oleate are also useful herein, as well as liposomes. Other carriers include, but are not limited to: fillers, such as sugars, for example lactose, saccharose, mannitol or sorbitol, cellulose preparations and/or calcium phosphates, for example tricalcium phosphate or calcium hydrogen phosphate, also binders, such as starches, for example corn, wheat, rice or potato starch, methylcellulose, hydroxypropylmethylcellulose, sodium carboxymethylcellulose or polyvinylpyrolidone, and/or, if desired, disintegrators, such as the above-mentioned starches, also carboxymethyl starch, cross-linked polyvinylpyrrolidone, alginic acid or a salt thereof, such as sodium alginate. Additional pharmaceutically acceptable carriers and their formulation are described in standard formulation treatises, such as *Remington's Pharmaceutical Sciences* by E. W. Martin. See also Wang, Y. J. and Hanson, M. A., *Journal of Parenteral Science and Technology*, Technical Report No. 10, Supp. 42:2S, 1988.

If desired, the disclosed pharmaceutical compositions can also contain minor amounts of non-toxic auxiliary substances, such as wetting or emulsifying agents, preservatives, and pH buffering agents and the like, for example sodium acetate or sorbitan monolaurate. Excipients that can be included in the disclosed compositions include flow conditioners and lubricants, for example silicic acid, talc, stearic acid or salts thereof, such as magnesium or calcium stearate, and/or polyethylene glycol, or derivatives thereof.

Compositions including the identified therapeutic agent can be administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral, otic, or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Sustained-release compositions include liposomes containing the identified therapeutic agent (see generally, Langer, *Science* 249:1527-1533, 1990; Treat et al., in *Liposomes in the Therapy of Infectious Disease and Cancer*, Lopez-Berestein and Fidler (eds.), Liss, New York, pp. 317-327 and 353-65, 1989). Liposomes containing the identified therapeutic agent thereof can be prepared by known methods: DE 3,218,121; Epstein et al., *Proc. Natl. Acad. Sci. U.S.A.* 82:3688-92, 1985; Hwang et al., *Proc. Natl. Acad. Sci. USA.* 77:4030-4034, 1980; EP 52,322; EP 36,676; EP 88,046; EP 143,949; EP 142,641; Japanese Patent Application No. 83-118008; U.S. Pat. No. 4,485,045, U.S. Pat. No. 4,544,545; and EP 102,324.

Preparations for administration can be suitably formulated to give controlled release of a therapeutic agent disclosed herein. For example, the pharmaceutical compositions can be in the form of particles comprising a biodegradable polymer or a polysaccharide jellifying or bioadhesive polymer, an amphiphilic polymer, an agent modifying the interface properties of the particles and a pharmacologically active substance. These compositions exhibit certain biocompatibility features that allow a controlled release of the active substance. See U.S. Pat. No. 5,700,486.

Compositions that include the identified therapeutic agent can be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321: 574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, the pump is implanted (for example see U.S. Pat. Nos. 6,436,091; 5,939,380; and 5,993,414). Implantable drug infusion devices are used to provide patients with a constant and long-term dosage or infusion of a drug or any other therapeutic agent. Such device can be categorized as either active or passive.

Active drug or programmable infusion devices feature a pump or a metering system to deliver the agent into the patient's system. An example of such an active infusion device currently available is the Medtronic SynchroMed™ programmable pump. Passive infusion devices, in contrast, do not feature a pump, but rather rely upon a pressurized drug reservoir to deliver the agent of interest. An example of such a device includes the Medtronic IsoMed™.

For oral administration, the pharmaceutical compositions can take the form of, for example, powders, pills, tablets, or capsules, prepared by conventional means with pharmaceutically acceptable excipients such as binding agents (such as pregelatinized maize starch, polyvinylpyrrolidone or hydroxypropyl methylcellulose); fillers (such as lactose, microcrystalline cellulose or calcium hydrogen phosphate); lubricants (such as magnesium stearate, talc or silica); disintegrants (such as potato starch or sodium starch glycolate); or wetting agents (such as sodium lauryl sulphate). The tablets can be coated by methods well known in the art.

For administration by inhalation, the compounds for use according to the present disclosure can be conveniently delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of for example gelatin for use in an inhaler or insufflator can be formulated containing a powder mix of the compound and a suitable powder base such as lactose or starch.

For inhalation, the composition of the present disclosure can also be administered as an aerosol or as a dispersion in a carrier. In one specific, non-limiting example, the identified therapeutic agent (alone or in combination with other therapeutic agents or pharmaceutically acceptable carriers), is administered as an aerosol from a conventional valve, such as, but not limited to, a metered dose valve, through an aerosol adapter also known as an actuator. A suitable fluid carrier can be also included in the formulation, such as, but not limited to, air, a hydrocarbon, such as n-butane, propane, isopentane, amongst others, or a propellant, such as, but not limited to a fluorocarbon. Optionally, a stabilizer is also included, or porous particles for deep lung delivery are included (for example, see U.S. Pat. No. 6,447,743).

In the disclosed methods of treating cardiac disorders that result from decreased sensitivity of NPR for NP, the method includes administering to a subject (such as a subject having cardiovascular disease) a therapeutically effective amount of a therapeutic agent identified using the methods disclosed herein. Such agents can be administered in a single or divided dose. In particular examples, suitable single or divided doses include, but are not limited to about 0.01, 0.1, 0.5, 1, 3, 5, 10, 15, 30, or 50 µg of agent/kg of subject/day.

The disclosure also provides a pharmaceutical pack or kit including one or more containers filled with one or more of the ingredients of the pharmaceutical compositions. Optionally associated with such container(s) can be a notice in the form prescribed by a governmental agency regulating the manufacture, use or sale of pharmaceuticals or biological products, which notice reflects approval by the agency of manufacture, use or sale for human administration. Instructions for use of the composition can also be included.

The disclosure provides compositions that include one or more of the identified therapeutic agents using the methods described in Example 14, one or more of the RNAi molecules described in Example 15, or combinations thereof, for example a composition that includes at least 50%, for example at least 90%, of the therapeutic agent in the composition. Such compositions are useful as therapeutic agents when constituted as pharmaceutical compositions with the appropriate carriers or diluents.

In view of the many possible embodiments to which the principles of the disclosed invention may be applied, it should be recognized that the illustrated examples are only examples of the invention and should not be taken as limiting the scope of the invention. Rather, the scope of the invention is defined by the following claims. We therefore claim as our invention all that comes within the scope and spirit of these claims.

We claim:

1. An assay for identifying an agent that increases biological activity of natriuretic peptide receptor A (NPRA) or natriuretic peptide receptor B (NPRB), decreases deleterious soluble natriuretic peptide receptor-related fragment (sNRF)-mediated growth factor activity, or increases biological activity of NPRA or NRPB and decreases deleterious sNRF-mediated growth factor activity, comprising:
    contacting a test agent with a cell, wherein the cell comprises a reporter, a NPRA or NPRB, and a sNRF that interferes with binding of cGMP-dependent kinase I (PKG) to the NPRA or NPRB, wherein the sNRF comprises the amino acid sequence shown in SEQ ID NO: 4 or 6;
    contacting the cell with a growth factor;
    contacting the cell with a natriuretic peptide (NP);
    measuring biological activity of the NPRA or NPRB, measuring sNRF-mediated growth factor activity, or measuring biological activity of the NPRA or NPRB and sNRF-mediated growth factor activity;
    comparing the biological activity of the NPRA or NPRB, the sNRF-mediated growth factor activity, or the biological activity of the NPRA or NPRB and sNRF-mediated growth factor activity, in the presence of the test agent to the biological activity of the NPRA or NPRB, the sNRF-mediated growth factor activity, or the biological activity of the NPRA or NPRB and sNRF-mediated growth factor activity, in the absence of the test agent; and
    determining whether the test agent increases biological activity of the NPRA or NPRB, decreases deleterious sNRF-mediated growth factor activity, or increases biological activity of the NPRA or NPRB and decreases sNRF-mediated growth factor activity.

2. The assay of claim 1, wherein the cell is a cardiac cell.

3. The assay of claim 2, wherein the cardiac cell is a cardiac fibroblast (CF) or a cardiac myocyte.

4. The assay of claim 3, wherein the CF is a primary CF cell isolated from a mammal.

5. The assay of claim 1, wherein the reporter comprises a promoter operably linked to a reporter nucleic acid sequence, and wherein the promoter is responsive to a growth factor and wherein growth factor activity is modulated by NP.

6. The assay of claim 5, wherein the promoter is activated in the presence of a growth factor, and wherein growth factor activity is reduced by NP.

7. The assay of claim 1, wherein the reporter comprises a cyclic nucleotide-gated (CNG) channel.

8. The assay of claim 1, wherein determining whether the test agent increases biological activity of the NPRA or NPRB comprises detecting a signal generated from a protein encoded by the reporter nucleic acid sequence, wherein a decrease in the signal in the presence of the test agent as compared to the signal in the absence of the test agent identifies the test agent as an agent that increases biological activity of the NPRA or NPRB.

9. The assay of claim 1, wherein increases in the biological activity of the NPRa or NPRB comprise increases in the sensitivity of the NPRA or NPRB for NP.

10. The assay of claim 1, wherein decreases in the deleterious sNRF-mediated growth factor activity comprise decreases in sNRF biological activity.

11. The assay of claim 1, wherein the sNRF that interferes with binding of PKG to NPR does not comprise an NPRA kinase-like domain.

12. The assay of claim 11, wherein the sNRF that interferes with binding of PKG to NPR comprises an NPRA hinge domain.

13. The assay of claim 1, wherein the sNRF that interferes with binding of PKG to NPR consists of the amino acid sequence shown in SEQ ID NO: 4 or 6.

14. The assay of claim 1, wherein the amino acid sequence comprising SEQ ID NO: 4 or 6 has 1-10 conservative amino acid substitutions.

15. The assay of claim 1, wherein the growth factor comprises EGF or transforming growth factor (TGF)-β.

16. The assay of claim 1, wherein the NP comprises atrial NP (ANP) or brain NP (BNP).

17. The assay of claim 1, further comprising:
administering a therapeutically effective amount of the test agent determined to increase biological activity of NPRA or NRPB, decrease deleterious sNRF-mediated growth factor activity, or increase biological activity of NPRA or NRPB and decrease deleterious sNRF-mediated growth factor activity, to a laboratory mammal having cardiovascular disease; and
measuring symptoms of the cardiovascular disease, wherein a decrease in symptoms of the cardiovascular disease in the presence of the test agent as compared to symptoms of the cardiovascular disease in the absence of the test agent indicates that the test agent treats cardiovascular disease in the laboratory mammal.

18. The assay of claim 1, wherein the test agent is a nucleic acid molecule, protein, organic compound, inorganic compound, or combinations thereof.

19. The assay of claim 1, wherein determining whether the test agent decreases deleterious sNRF-mediated growth factor activity comprises detecting a signal generated from a protein encoded by the reporter nucleic acid sequence, wherein no significant change in the signal in the presence of the test agent as compared to the signal in the absence of the test agent identifies the test agent as an agent that decreases deleterious sNRF-mediated growth factor activity.

20. An assay for identifying an agent that increases biological activity of natriuretic peptide receptor A (NPRA), decreases soluble natriuretic peptide receptor-related fragment (sNRF)-induced potentiation of harmful growth factor effects, or increases biological activity of NPRA and decreases sNRF-induced potentiation of harmful growth factor effects, comprising:
contacting a test agent with a cardiac fibroblast (CF), wherein the CF comprises (i) an alpha smooth muscle actin (α-SMA) promoter operably linked upstream to a reporter nucleic acid sequence, (ii) NPRA, and (iii) a recombinant sNRF amino acid sequence consisting of SEQ ID NO: 4 or 6;
contacting the CF with transforming growth factor (TGF)-β;
contacting the CF with atrial natriuretic peptide (ANP);
measuring a signal produced by a protein encoded by the reporter nucleic acid sequence; and
determining whether the signal produced in the presence of the test agent is decreased as compared to the signal produced in the absence of the test agent, wherein a decrease in the signal identifies the test agent as an agent that increases biological activity of NPRA, decreases sNRF-induced potentiation of harmful growth factor effects, or increases biological activity of NPRA and decreases sNRF-induced potentiation of harmful growth factor effects.

21. An assay for identifying an agent that decreases deleterious soluble natriuretic peptide receptor-related fragment (sNRF-mediated growth factor activity, comprising:
contacting a test agent with a cardiac fibroblast (CF), wherein the CF comprises (i) a cyclic nucleotide-gated (CNG) channel reporter nucleic acid sequence, (ii) natriuretic peptide receptor A (NPRA), and (iii) a recombinant sNRF amino acid sequence consisting of SEQ ID NO: 4 or 6;
contacting the CF with transforming growth factor (TGF-β);
contacting the CF with atrial natriuretic peptide (ANP);
measuring a signal produced when in the presence of intracellular calcium; and
determining whether the signal produced in the presence of the test agent is altered as compared to the signal produced in the absence of the test agent, wherein no significant change in the signal identifies the test agent as an agent that decreases deleterious sNRF-mediated growth factor activity.

* * * * *

SEQUENCE LISTING

```
<160> NUMBER OF SEQ ID NOS: 44

<210> SEQ ID NO 1
<211> LENGTH: 3186
<212> TYPE: DNA
<213> ORGANISM: Homo sapiens
<220> FEATURE:
<221> NAME/KEY: CDS
<222> LOCATION: (1)..(3186)

<400> SEQUENCE: 1 atg ccg ggg ccc cgg cgc ccc gct ggc tcc cgc ctg cgc ctg ctc ctg        48
Met Pro Gly Pro Arg Arg Pro Ala Gly Ser Arg Leu Arg Leu Leu Leu
1               5                   10                  15 ctc ctg ctg ctg ccg ccg ctg ctg ctg ctc cgg ggc agc cac gcg            96
Leu Leu Leu Leu Pro Pro Leu Leu Leu Leu Arg Gly Ser His Ala
            20                  25                  30 ggc aac ctg acg gta gcc gtg gta ctg ccg ctg gcc aat acc tcg tac       144
Gly Asn Leu Thr Val Ala Val Val Leu Pro Leu Ala Asn Thr Ser Tyr
        35                  40                  45 ccc tgg tcg tgg gcg cgc gtg gga ccc gcc gtg gag ctg gcc ctg gcc       192
Pro Trp Ser Trp Ala Arg Val Gly Pro Ala Val Glu Leu Ala Leu Ala
    50                  55                  60 cag gtg aag gcg cgc ccc gac ttg ctg ccg ggc tgg acg gtc cgc acg       240
Gln Val Lys Ala Arg Pro Asp Leu Leu Pro Gly Trp Thr Val Arg Thr
65                  70                  75                  80 gtg ctg ggc agc agc gaa aac gcg ctg ggc gtc tgc tcc gac acc gca       288
Val Leu Gly Ser Ser Glu Asn Ala Leu Gly Val Cys Ser Asp Thr Ala
                85                  90                  95 gcg ccc ctg gcc gcg gtg gac ctc aag tgg gag cac aac ccc gct gtg       336
Ala Pro Leu Ala Ala Val Asp Leu Lys Trp Glu His Asn Pro Ala Val
            100                 105                 110 ttc ctg ggc ccc ggc tgc gtg tac gcc gcc gcc cca gtg ggg cgc ttc       384
Phe Leu Gly Pro Gly Cys Val Tyr Ala Ala Ala Pro Val Gly Arg Phe
        115                 120                 125 acc gcg cac tgg cgg gtc ccg ctg ctg acc gcc ggc gcc ccg gcg ctg       432
Thr Ala His Trp Arg Val Pro Leu Leu Thr Ala Gly Ala Pro Ala Leu
    130                 135                 140 ggc ttc ggt gtc aag gac gag tat gcg ctg acc acc cgc gcg ggg ccc       480
Gly Phe Gly Val Lys Asp Glu Tyr Ala Leu Thr Thr Arg Ala Gly Pro
145                 150                 155                 160 agc tac gcc aag ctg ggg gac ttc gtg gcg gcg ctg cac cga cgg ctg       528
Ser Tyr Ala Lys Leu Gly Asp Phe Val Ala Ala Leu His Arg Arg Leu
                165                 170                 175 ggc tgg gag cgc caa gcg ctc atg ctc tac gcc tac cgg ccg ggt gac       576
Gly Trp Glu Arg Gln Ala Leu Met Leu Tyr Ala Tyr Arg Pro Gly Asp
            180                 185                 190
```

```
gaa gag cac tgc ttc ttc ctc gtg gag ggg ctg ttc atg cgg gtc cgc      624
Glu Glu His Cys Phe Phe Leu Val Glu Gly Leu Phe Met Arg Val Arg
        195                 200                 205 gac cgc ctc aat att acg gtg gac cac ctg gag ttc gcc gag gac gac      672
Asp Arg Leu Asn Ile Thr Val Asp His Leu Glu Phe Ala Glu Asp Asp
    210                 215                 220 ctc agc cac tac acc agg ctg ctg cgg acc atg ccg cgc aaa ggc cga      720
Leu Ser His Tyr Thr Arg Leu Leu Arg Thr Met Pro Arg Lys Gly Arg
225                 230                 235                 240 gtt atc tac atc tgc agc tcc cct gat gcc ttc aga acc ctc atg ctc      768
Val Ile Tyr Ile Cys Ser Ser Pro Asp Ala Phe Arg Thr Leu Met Leu
                245                 250                 255 ctg gcc ctg gaa gct ggc ttg tgt ggg gag gac tac gtt ttc ttc cac      816
Leu Ala Leu Glu Ala Gly Leu Cys Gly Glu Asp Tyr Val Phe Phe His
            260                 265                 270 ctg gat atc ttt ggg caa agc ctg caa ggt gga cag ggc cct gct ccc      864
Leu Asp Ile Phe Gly Gln Ser Leu Gln Gly Gly Gln Gly Pro Ala Pro
        275                 280                 285 cgc agg ccc tgg gag aga ggg gat ggg cag gat gtc agt gcc cgc cag      912
Arg Arg Pro Trp Glu Arg Gly Asp Gly Gln Asp Val Ser Ala Arg Gln
    290                 295                 300 gcc ttt cag gct gcc aaa atc att aca tat aaa gac cca gat aat ccc      960
Ala Phe Gln Ala Ala Lys Ile Ile Thr Tyr Lys Asp Pro Asp Asn Pro
305                 310                 315                 320 gag tac ttg gaa ttc ctg aag cag tta aaa cac ctg gcc tat gag cag     1008
Glu Tyr Leu Glu Phe Leu Lys Gln Leu Lys His Leu Ala Tyr Glu Gln
                325                 330                 335 ttc aac ttc acc atg gag gat gtc ctg gtg aac acc atc cca gca tcc     1056
Phe Asn Phe Thr Met Glu Asp Val Leu Val Asn Thr Ile Pro Ala Ser
            340                 345                 350 ttc cac gac ggg ctc ctc ctc tat atc cag gca gtg acg gag act ctg     1104
Phe His Asp Gly Leu Leu Leu Tyr Ile Gln Ala Val Thr Glu Thr Leu
        355                 360                 365 gca cat ggg gga act gtt act gat ggg gag aac atc act cag cgg atg     1152
Ala His Gly Gly Thr Val Thr Asp Gly Glu Asn Ile Thr Gln Arg Met
    370                 375                 380 tgg aac cga agc ttt caa ggt gtg aca gga tac ctg aaa att gat agc     1200
Trp Asn Arg Ser Phe Gln Gly Val Thr Gly Tyr Leu Lys Ile Asp Ser
385                 390                 395                 400 agt ggc gat cgg gaa aca gac ttc tcc ctc tgg gat atg gat ccc gag     1248
Ser Gly Asp Arg Glu Thr Asp Phe Ser Leu Trp Asp Met Asp Pro Glu
                405                 410                 415 aat ggt gcc ttc agg gtt gta ctg aac tac aat ggg act tcc caa gag     1296
Asn Gly Ala Phe Arg Val Val Leu Asn Tyr Asn Gly Thr Ser Gln Glu
            420                 425                 430 ctg gtg gct gtg tcg ggg cgc aaa ctg aac tgg ccc ctg ggg tac cct     1344
Leu Val Ala Val Ser Gly Arg Lys Leu Asn Trp Pro Leu Gly Tyr Pro
        435                 440                 445 cct cct gac atc ccc aaa tgt ggc ttt gac aac gaa gac cca gca tgc     1392
Pro Pro Asp Ile Pro Lys Cys Gly Phe Asp Asn Glu Asp Pro Ala Cys
    450                 455                 460 aac caa gat cac ctt tcc acc ctg gag gtg ctg gct ttg gtg ggc agc     1440
Asn Gln Asp His Leu Ser Thr Leu Glu Val Leu Ala Leu Val Gly Ser
465                 470                 475                 480 ctc tcc ttg ctc ggc att ctg att gtc tcc ttc ttc ata tac agg aag     1488
Leu Ser Leu Leu Gly Ile Leu Ile Val Ser Phe Phe Ile Tyr Arg Lys
                485                 490                 495 atg cag ctg gag aag gaa ctg gcc tcg gag ctg tgg cgg gtg cgc tgg     1536
Met Gln Leu Glu Lys Glu Leu Ala Ser Glu Leu Trp Arg Val Arg Trp
            500                 505                 510
```

```
gag gac gtt gag ccc agt agc ctt gag agg cac ctg cgg agt gca ggc    1584
Glu Asp Val Glu Pro Ser Ser Leu Glu Arg His Leu Arg Ser Ala Gly
        515                 520                 525 agc cgg ctg acc ctg agc ggg aga ggc tcc aat tac ggc tcc ctg cta    1632
Ser Arg Leu Thr Leu Ser Gly Arg Gly Ser Asn Tyr Gly Ser Leu Leu
530                 535                 540 acc aca gag ggc cag ttc caa gtc ttt gcc aag aca gca tat tat aag    1680
Thr Thr Glu Gly Gln Phe Gln Val Phe Ala Lys Thr Ala Tyr Tyr Lys
545                 550                 555                 560 ggc aac ctc gtg gct gtg aaa cgt gtg aac cgt aaa cgc att gag ctg    1728
Gly Asn Leu Val Ala Val Lys Arg Val Asn Arg Lys Arg Ile Glu Leu
                565                 570                 575 aca cga aaa gtc ctg ttt gaa ctg aag cat atg cgg gat gtg cag aat    1776
Thr Arg Lys Val Leu Phe Glu Leu Lys His Met Arg Asp Val Gln Asn
        580                 585                 590 gaa cac ctg acc agg ttt gtg gga gcc tgc acc gac ccc ccc aat atc    1824
Glu His Leu Thr Arg Phe Val Gly Ala Cys Thr Asp Pro Pro Asn Ile
            595                 600                 605 tgc atc ctc aca gag tac tgt ccc cgt ggg agc ctg cag gac att ctg    1872
Cys Ile Leu Thr Glu Tyr Cys Pro Arg Gly Ser Leu Gln Asp Ile Leu
    610                 615                 620 gag aat gag agc atc acc ctg gac tgg atg ttc cgg tac tca ctc acc    1920
Glu Asn Glu Ser Ile Thr Leu Asp Trp Met Phe Arg Tyr Ser Leu Thr
625                 630                 635                 640 aat gac atc gtc aag ggc atg ctg ttt cta cac aat ggg gct atc tgt    1968
Asn Asp Ile Val Lys Gly Met Leu Phe Leu His Asn Gly Ala Ile Cys
                645                 650                 655 tcc cat ggg aac ctc aag tca tcc aac tgc gtg gta gat ggg cgc ttt    2016
Ser His Gly Asn Leu Lys Ser Ser Asn Cys Val Val Asp Gly Arg Phe
            660                 665                 670 gtg ctc aag atc acc gac tat ggg ctg gag agc ttc agg gac ctg gac    2064
Val Leu Lys Ile Thr Asp Tyr Gly Leu Glu Ser Phe Arg Asp Leu Asp
    675                 680                 685 cca gag caa gga cac acc gtt tat gcc aaa aag ctg tgg acg gcc cct    2112
Pro Glu Gln Gly His Thr Val Tyr Ala Lys Lys Leu Trp Thr Ala Pro
690                 695                 700 gag ctc ctg cga atg gct tca ccc cct gtg cgg ggc tcc cag gct ggt    2160
Glu Leu Leu Arg Met Ala Ser Pro Pro Val Arg Gly Ser Gln Ala Gly
705                 710                 715                 720 gac gta tac agc ttt ggg atc atc ctt cag gag att gcc ctg agg agt    2208
Asp Val Tyr Ser Phe Gly Ile Ile Leu Gln Glu Ile Ala Leu Arg Ser
                725                 730                 735 ggg gtc ttc cac gtg gaa ggt ttg gac ctg agc ccc aaa gag atc atc    2256
Gly Val Phe His Val Glu Gly Leu Asp Leu Ser Pro Lys Glu Ile Ile
            740                 745                 750 gag cgg gtg act cgg ggt gag cag ccc ccc ttc cgg ccc tcc ctg gcc    2304
Glu Arg Val Thr Arg Gly Glu Gln Pro Pro Phe Arg Pro Ser Leu Ala
    755                 760                 765 ctg cag agt cac ctg gag gag ttg ggg ctg ctc atg cag cgg tgc tgg    2352
Leu Gln Ser His Leu Glu Glu Leu Gly Leu Leu Met Gln Arg Cys Trp
770                 775                 780 gct gag gac cca cag gag agg cca cca ttc cag cag atc cgc ctg acg    2400
Ala Glu Asp Pro Gln Glu Arg Pro Pro Phe Gln Gln Ile Arg Leu Thr
785                 790                 795                 800 ttg cgc aaa ttt aac agg gag aac agc agc aac atc ctg gac aac ctg    2448
Leu Arg Lys Phe Asn Arg Glu Asn Ser Ser Asn Ile Leu Asp Asn Leu
                805                 810                 815 ctg tcc cgc atg gag cag tac gcg aac aat ctg gag gaa ctg gtg gag    2496
Leu Ser Arg Met Glu Gln Tyr Ala Asn Asn Leu Glu Glu Leu Val Glu
            820                 825                 830
```

```
gag cgg acc cag gca tac ctg gag gag aag cgc aag gct gag gcc ctg      2544
Glu Arg Thr Gln Ala Tyr Leu Glu Glu Lys Arg Lys Ala Glu Ala Leu
        835                 840                 845 ctc tac cag atc ctg cct cac tca gtg gct gag cag ctg aag cgt ggg      2592
Leu Tyr Gln Ile Leu Pro His Ser Val Ala Glu Gln Leu Lys Arg Gly
    850                 855                 860 gag acg gtg cag gcc gaa gcc ttt gac agt gtt acc atc tac ttc agt      2640
Glu Thr Val Gln Ala Glu Ala Phe Asp Ser Val Thr Ile Tyr Phe Ser
865                 870                 875                 880 gac att gtg ggt ttc aca gcg ctg tcg gcg gag agc acg ccc atg cag      2688
Asp Ile Val Gly Phe Thr Ala Leu Ser Ala Glu Ser Thr Pro Met Gln
                885                 890                 895 gtg gtg acc ctg ctc aat gac ctg tac act tgc ttt gat gct gtc ata      2736
Val Val Thr Leu Leu Asn Asp Leu Tyr Thr Cys Phe Asp Ala Val Ile
        900                 905                 910 gac aac ttt gat gtg tac aag gtg gag aca att ggc gat gcc tac atg      2784
Asp Asn Phe Asp Val Tyr Lys Val Glu Thr Ile Gly Asp Ala Tyr Met
    915                 920                 925 gtg gtg tca ggg ctc cct gtg cgg aac ggg cgg cta cac gcc tgc gag      2832
Val Val Ser Gly Leu Pro Val Arg Asn Gly Arg Leu His Ala Cys Glu
930                 935                 940 gta gcc cgc atg gcc ctg gca ctg ctg gat gct gtg cgc tcc ttc cga      2880
Val Ala Arg Met Ala Leu Ala Leu Leu Asp Ala Val Arg Ser Phe Arg
945                 950                 955                 960 atc cgc cac cgg ccc cag gag cag ctg cgc ttg cgc att ggc atc cac      2928
Ile Arg His Arg Pro Gln Glu Gln Leu Arg Leu Arg Ile Gly Ile His
                965                 970                 975 aca gga cct gtg tgt gct gga gtg gtg gga ctg aag atg ccc cgt tac      2976
Thr Gly Pro Val Cys Ala Gly Val Val Gly Leu Lys Met Pro Arg Tyr
        980                 985                 990 tgt ctc ttt ggg gat aca gtc aac aca gcc tca aga atg gag tct aat      3024
Cys Leu Phe Gly Asp Thr Val Asn Thr Ala Ser Arg Met Glu Ser Asn
    995                 1000                1005 ggg gaa gcc ctg aag atc cac ttg tct tct gag acc aag gct gtc          3069
Gly Glu Ala Leu Lys Ile His Leu Ser Ser Glu Thr Lys Ala Val
1010                1015                1020 ctg gag gag ttt ggt ggt ttc gag ctg gag ctt cga ggg gat gta          3114
Leu Glu Glu Phe Gly Gly Phe Glu Leu Glu Leu Arg Gly Asp Val
    1025                1030                1035 gaa atg aag ggc aaa ggc aag gtt cgg acc tac tgg ctc ctt ggg          3159
Glu Met Lys Gly Lys Gly Lys Val Arg Thr Tyr Trp Leu Leu Gly
        1040                1045                1050 gag agg ggg agt agc acc cga ggc tga                                  3186
Glu Arg Gly Ser Ser Thr Arg Gly
    1055                1060

<210> SEQ ID NO 2
<211> LENGTH: 1061
<212> TYPE: PRT
<213> ORGANISM: Homo sapiens

<400> SEQUENCE: 2

Met Pro Gly Pro Arg Pro Ala Gly Ser Arg Leu Arg Leu Leu Leu
1               5                   10                  15

Leu Leu Leu Leu Pro Pro Leu Leu Leu Leu Leu Arg Gly Ser His Ala
                20                  25                  30

Gly Asn Leu Thr Val Ala Val Val Leu Pro Leu Ala Asn Thr Ser Tyr
            35                  40                  45

Pro Trp Ser Trp Ala Arg Val Gly Pro Ala Val Glu Leu Ala Leu Ala
        50                  55                  60
```

-continued

```
Gln Val Lys Ala Arg Pro Asp Leu Leu Pro Gly Trp Thr Val Arg Thr
 65                  70                  75                  80

Val Leu Gly Ser Ser Glu Asn Ala Leu Gly Val Cys Ser Asp Thr Ala
                 85                  90                  95

Ala Pro Leu Ala Ala Val Asp Leu Lys Trp Glu His Asn Pro Ala Val
            100                 105                 110

Phe Leu Gly Pro Gly Cys Val Tyr Ala Ala Pro Val Gly Arg Phe
        115                 120                 125

Thr Ala His Trp Arg Val Pro Leu Leu Thr Gly Ala Pro Ala Leu
    130                 135                 140

Gly Phe Gly Val Lys Asp Glu Tyr Ala Leu Thr Thr Arg Ala Gly Pro
145                 150                 155                 160

Ser Tyr Ala Lys Leu Gly Asp Phe Val Ala Ala Leu His Arg Arg Leu
                165                 170                 175

Gly Trp Glu Arg Gln Ala Leu Met Leu Tyr Ala Tyr Arg Pro Gly Asp
            180                 185                 190

Glu Glu His Cys Phe Phe Leu Val Glu Gly Leu Phe Met Arg Val Arg
        195                 200                 205

Asp Arg Leu Asn Ile Thr Val Asp His Leu Glu Phe Ala Glu Asp Asp
210                 215                 220

Leu Ser His Tyr Thr Arg Leu Leu Arg Thr Met Pro Arg Lys Gly Arg
225                 230                 235                 240

Val Ile Tyr Ile Cys Ser Ser Pro Asp Ala Phe Arg Thr Leu Met Leu
                245                 250                 255

Leu Ala Leu Glu Ala Gly Leu Cys Gly Glu Asp Tyr Val Phe Phe His
            260                 265                 270

Leu Asp Ile Phe Gly Gln Ser Leu Gln Gly Gly Gln Gly Pro Ala Pro
        275                 280                 285

Arg Arg Pro Trp Glu Arg Gly Asp Gly Gln Asp Val Ser Ala Arg Gln
    290                 295                 300

Ala Phe Gln Ala Ala Lys Ile Ile Thr Tyr Lys Asp Pro Asp Asn Pro
305                 310                 315                 320

Glu Tyr Leu Glu Phe Leu Lys Gln Leu Lys His Leu Ala Tyr Glu Gln
                325                 330                 335

Phe Asn Phe Thr Met Glu Asp Val Leu Val Asn Thr Ile Pro Ala Ser
            340                 345                 350

Phe His Asp Gly Leu Leu Leu Tyr Ile Gln Ala Val Thr Glu Thr Leu
        355                 360                 365

Ala His Gly Gly Thr Val Thr Asp Gly Glu Asn Ile Thr Gln Arg Met
    370                 375                 380

Trp Asn Arg Ser Phe Gln Gly Val Thr Gly Tyr Leu Lys Ile Asp Ser
385                 390                 395                 400

Ser Gly Asp Arg Glu Thr Asp Phe Ser Leu Trp Asp Met Asp Pro Glu
                405                 410                 415

Asn Gly Ala Phe Arg Val Val Leu Asn Tyr Asn Gly Thr Ser Gln Glu
            420                 425                 430

Leu Val Ala Val Ser Gly Arg Lys Leu Asn Trp Pro Leu Gly Tyr Pro
        435                 440                 445

Pro Pro Asp Ile Pro Lys Cys Gly Phe Asp Asn Glu Asp Pro Ala Cys
    450                 455                 460

Asn Gln Asp His Leu Ser Thr Leu Glu Val Leu Ala Leu Val Gly Ser
465                 470                 475                 480

Leu Ser Leu Leu Gly Ile Leu Ile Val Ser Phe Phe Ile Tyr Arg Lys
                485                 490                 495
```

```
Met Gln Leu Glu Lys Glu Leu Ala Ser Glu Leu Trp Arg Val Arg Trp
            500                 505                 510

Glu Asp Val Glu Pro Ser Ser Leu Glu Arg His Leu Arg Ser Ala Gly
            515                 520                 525

Ser Arg Leu Thr Leu Ser Gly Arg Gly Ser Asn Tyr Gly Ser Leu Leu
            530                 535                 540

Thr Thr Glu Gly Gln Phe Gln Val Phe Ala Lys Thr Ala Tyr Tyr Lys
545                 550                 555                 560

Gly Asn Leu Val Ala Val Lys Arg Val Asn Arg Lys Arg Ile Glu Leu
                565                 570                 575

Thr Arg Lys Val Leu Phe Glu Leu Lys His Met Arg Asp Val Gln Asn
            580                 585                 590

Glu His Leu Thr Arg Phe Val Gly Ala Cys Thr Asp Pro Pro Asn Ile
            595                 600                 605

Cys Ile Leu Thr Glu Tyr Cys Pro Arg Gly Ser Leu Gln Asp Ile Leu
            610                 615                 620

Glu Asn Glu Ser Ile Thr Leu Asp Trp Met Phe Arg Tyr Ser Leu Thr
625                 630                 635                 640

Asn Asp Ile Val Lys Gly Met Leu Phe Leu His Asn Gly Ala Ile Cys
                645                 650                 655

Ser His Gly Asn Leu Lys Ser Ser Asn Cys Val Val Asp Gly Arg Phe
            660                 665                 670

Val Leu Lys Ile Thr Asp Tyr Gly Leu Glu Ser Phe Arg Asp Leu Asp
            675                 680                 685

Pro Glu Gln Gly His Thr Val Tyr Ala Lys Lys Leu Trp Thr Ala Pro
690                 695                 700

Glu Leu Leu Arg Met Ala Ser Pro Pro Val Arg Gly Ser Gln Ala Gly
705                 710                 715                 720

Asp Val Tyr Ser Phe Gly Ile Ile Leu Gln Glu Ile Ala Leu Arg Ser
                725                 730                 735

Gly Val Phe His Val Glu Gly Leu Asp Leu Ser Pro Lys Glu Ile Ile
            740                 745                 750

Glu Arg Val Thr Arg Gly Glu Gln Pro Pro Phe Arg Pro Ser Leu Ala
            755                 760                 765

Leu Gln Ser His Leu Glu Glu Leu Gly Leu Leu Met Gln Arg Cys Trp
            770                 775                 780

Ala Glu Asp Pro Gln Glu Arg Pro Pro Phe Gln Gln Ile Arg Leu Thr
785                 790                 795                 800

Leu Arg Lys Phe Asn Arg Glu Asn Ser Ser Asn Ile Leu Asp Asn Leu
                805                 810                 815

Leu Ser Arg Met Glu Gln Tyr Ala Asn Asn Leu Glu Glu Leu Val Glu
            820                 825                 830

Glu Arg Thr Gln Ala Tyr Leu Glu Glu Lys Arg Lys Ala Glu Ala Leu
            835                 840                 845

Leu Tyr Gln Ile Leu Pro His Ser Val Ala Glu Gln Leu Lys Arg Gly
850                 855                 860

Glu Thr Val Gln Ala Glu Ala Phe Asp Ser Val Thr Ile Tyr Phe Ser
865                 870                 875                 880

Asp Ile Val Gly Phe Thr Ala Leu Ser Ala Glu Ser Thr Pro Met Gln
                885                 890                 895

Val Val Thr Leu Leu Asn Asp Leu Tyr Thr Cys Phe Asp Ala Val Ile
            900                 905                 910

Asp Asn Phe Asp Val Tyr Lys Val Glu Thr Ile Gly Asp Ala Tyr Met
```

-continued

```
                        915                 920                 925

Val Val Ser Gly Leu Pro Val Arg Asn Gly Arg Leu His Ala Cys Glu
    930                 935                 940

Val Ala Arg Met Ala Leu Ala Leu Leu Asp Ala Val Arg Ser Phe Arg
945                 950                 955                 960

Ile Arg His Arg Pro Gln Glu Gln Leu Arg Leu Arg Ile Gly Ile His
                965                 970                 975

Thr Gly Pro Val Cys Ala Gly Val Val Gly Leu Lys Met Pro Arg Tyr
            980                 985                 990

Cys Leu Phe Gly Asp Thr Val Asn  Thr Ala Ser Arg Met  Glu Ser Asn
        995                 1000                1005

Gly Glu  Ala Leu Lys Ile His  Leu Ser Ser Glu Thr  Lys Ala Val
    1010                1015                1020

Leu Glu  Glu Phe Gly Gly Phe  Glu Leu Glu Leu Arg  Gly Asp Val
1025                1030                1035

Glu Met  Lys Gly Lys Gly Lys  Val Arg Thr Tyr Trp  Leu Leu Gly
    1040                1045                1050

Glu Arg  Gly Ser Ser Thr Arg  Gly
    1055                1060
```

```
<210> SEQ ID NO 3
<211> LENGTH: 774
<212> TYPE: DNA
<213> ORGANISM: Homo sapiens
<220> FEATURE:
<221> NAME/KEY: CDS
<222> LOCATION: (1)..(774)

<400> SEQUENCE: 3 atg agg gag aac agc agc aac atc ctg gac aac ctg ctg tcc cgc atg       48
Met Arg Glu Asn Ser Ser Asn Ile Leu Asp Asn Leu Leu Ser Arg Met
1               5                   10                  15 gag cag tac gcg aac aat ctg gag gaa ctg gtg gag gag cgg acc cag       96
Glu Gln Tyr Ala Asn Asn Leu Glu Glu Leu Val Glu Glu Arg Thr Gln
            20                  25                  30 gca tac ctg gag gag aag cgc aag gct gag gcc ctg ctc tac cag atc      144
Ala Tyr Leu Glu Glu Lys Arg Lys Ala Glu Ala Leu Leu Tyr Gln Ile
        35                  40                  45 ctg cct cac tca gtg gct gag cag ctg aag cgt ggg gag acg gtg cag      192
Leu Pro His Ser Val Ala Glu Gln Leu Lys Arg Gly Glu Thr Val Gln
    50                  55                  60 gcc gaa gcc ttt gac agt gtt acc atc tac ttc agt gac att gtg ggt      240
Ala Glu Ala Phe Asp Ser Val Thr Ile Tyr Phe Ser Asp Ile Val Gly
65                  70                  75                  80 ttc aca gcg ctg tcg gcg gag agc acg ccc atg cag gtg gtg acc ctg      288
Phe Thr Ala Leu Ser Ala Glu Ser Thr Pro Met Gln Val Val Thr Leu
                85                  90                  95 ctc aat gac ctg tac act tgc ttt gat gct gtc ata gac aac ttt gat      336
Leu Asn Asp Leu Tyr Thr Cys Phe Asp Ala Val Ile Asp Asn Phe Asp
            100                 105                 110 gtg tac aag gtg gag aca att ggc gat gcc tac atg gtg gtg tca ggg      384
Val Tyr Lys Val Glu Thr Ile Gly Asp Ala Tyr Met Val Val Ser Gly
        115                 120                 125 ctc cct gtg cgg aac ggg cgg cta cac gcc tgc gag gta gcc cgc atg      432
Leu Pro Val Arg Asn Gly Arg Leu His Ala Cys Glu Val Ala Arg Met
    130                 135                 140 gcc ctg gca ctg ctg gat gct gtg cgc tcc ttc cga atc cgc cac cgg      480
Ala Leu Ala Leu Leu Asp Ala Val Arg Ser Phe Arg Ile Arg His Arg
145                 150                 155                 160
```

```
ccc cag gag cag ctg cgc ttg cgc att ggc atc cac aca gga cct gtg      528
Pro Gln Glu Gln Leu Arg Leu Arg Ile Gly Ile His Thr Gly Pro Val
                165                 170                 175 tgt gct gga gtg gtg gga ctg aag atg ccc cgt tac tgt ctc ttt ggg      576
Cys Ala Gly Val Val Gly Leu Lys Met Pro Arg Tyr Cys Leu Phe Gly
            180                 185                 190 gat aca gtc aac aca gcc tca aga atg gag tct aat ggg gaa gcc ctg      624
Asp Thr Val Asn Thr Ala Ser Arg Met Glu Ser Asn Gly Glu Ala Leu
        195                 200                 205 aag atc cac ttg tct tct gag acc aag gct gtc ctg gag gag ttt ggt      672
Lys Ile His Leu Ser Ser Glu Thr Lys Ala Val Leu Glu Glu Phe Gly
    210                 215                 220 ggt ttc gag ctg gag ctt cga ggg gat gta gaa atg aag ggc aaa ggc      720
Gly Phe Glu Leu Glu Leu Arg Gly Asp Val Glu Met Lys Gly Lys Gly
225                 230                 235                 240 aag gtt cgg acc tac tgg ctc ctt ggg gag agg ggg agt agc acc cga      768
Lys Val Arg Thr Tyr Trp Leu Leu Gly Glu Arg Gly Ser Ser Thr Arg
                245                 250                 255 ggc tga                                                              774
Gly

<210> SEQ ID NO 4
<211> LENGTH: 257
<212> TYPE: PRT
<213> ORGANISM: Homo sapiens

<400> SEQUENCE: 4

Met Arg Glu Asn Ser Ser Asn Ile Leu Asp Asn Leu Leu Ser Arg Met
1               5                   10                  15

Glu Gln Tyr Ala Asn Asn Leu Glu Glu Leu Val Glu Glu Arg Thr Gln
            20                  25                  30

Ala Tyr Leu Glu Glu Lys Arg Lys Ala Glu Ala Leu Leu Tyr Gln Ile
        35                  40                  45

Leu Pro His Ser Val Ala Glu Gln Leu Lys Arg Gly Glu Thr Val Gln
    50                  55                  60

Ala Glu Ala Phe Asp Ser Val Thr Ile Tyr Phe Ser Asp Ile Val Gly
65                  70                  75                  80

Phe Thr Ala Leu Ser Ala Glu Ser Thr Pro Met Gln Val Val Thr Leu
                85                  90                  95

Leu Asn Asp Leu Tyr Thr Cys Phe Asp Ala Val Ile Asp Asn Phe Asp
            100                 105                 110

Val Tyr Lys Val Glu Thr Ile Gly Asp Ala Tyr Met Val Val Ser Gly
        115                 120                 125

Leu Pro Val Arg Asn Gly Arg Leu His Ala Cys Glu Val Ala Arg Met
    130                 135                 140

Ala Leu Ala Leu Leu Asp Ala Val Arg Ser Phe Arg Ile Arg His Arg
145                 150                 155                 160

Pro Gln Glu Gln Leu Arg Leu Arg Ile Gly Ile His Thr Gly Pro Val
                165                 170                 175

Cys Ala Gly Val Val Gly Leu Lys Met Pro Arg Tyr Cys Leu Phe Gly
            180                 185                 190

Asp Thr Val Asn Thr Ala Ser Arg Met Glu Ser Asn Gly Glu Ala Leu
        195                 200                 205

Lys Ile His Leu Ser Ser Glu Thr Lys Ala Val Leu Glu Glu Phe Gly
    210                 215                 220

Gly Phe Glu Leu Glu Leu Arg Gly Asp Val Glu Met Lys Gly Lys Gly
225                 230                 235                 240
```

```
Lys Val Arg Thr Tyr Trp Leu Leu Gly Glu Arg Gly Ser Ser Thr Arg
            245                 250                 255
Gly
```

<210> SEQ ID NO 5
<211> LENGTH: 291
<212> TYPE: DNA
<213> ORGANISM: Homo sapiens
<220> FEATURE:
<221> NAME/KEY: CDS
<222> LOCATION: (1)..(291)

<400> SEQUENCE: 5

```
atg agg gag aac agc agc aac atc ctg gac aac ctg ctg tcc cgc atg      48
Met Arg Glu Asn Ser Ser Asn Ile Leu Asp Asn Leu Leu Ser Arg Met
1               5                   10                  15 gag cag tac gcg aac aat ctg gag gaa ctg gtg gag gag cgg acc cag      96
Glu Gln Tyr Ala Asn Asn Leu Glu Glu Leu Val Glu Glu Arg Thr Gln
                20                  25                  30 gca tac ctg gag gag aag cgc aag gct gag gcc ctc tac cag atc         144
Ala Tyr Leu Glu Glu Lys Arg Lys Ala Glu Ala Leu Leu Tyr Gln Ile
            35                  40                  45 ctg cct cac tca gtg gct gag cag ctg aag cgt ggg gag acg gtg cag     192
Leu Pro His Ser Val Ala Glu Gln Leu Lys Arg Gly Glu Thr Val Gln
        50                  55                  60 gcc gaa gcc ttt gac agt gtt acc atc tac ttc agt gac att gtg ggt     240
Ala Glu Ala Phe Asp Ser Val Thr Ile Tyr Phe Ser Asp Ile Val Gly
65                  70                  75                  80 ttc aca gcg ctg tcg gcg gag agc acg ccc atg cag gtg gtg acc ctg     288
Phe Thr Ala Leu Ser Ala Glu Ser Thr Pro Met Gln Val Val Thr Leu
                85                  90                  95 tga                                                                  291
```

<210> SEQ ID NO 6
<211> LENGTH: 96
<212> TYPE: PRT
<213> ORGANISM: Homo sapiens

<400> SEQUENCE: 6

```
Met Arg Glu Asn Ser Ser Asn Ile Leu Asp Asn Leu Leu Ser Arg Met
1               5                   10                  15

Glu Gln Tyr Ala Asn Asn Leu Glu Glu Leu Val Glu Glu Arg Thr Gln
                20                  25                  30

Ala Tyr Leu Glu Glu Lys Arg Lys Ala Glu Ala Leu Leu Tyr Gln Ile
            35                  40                  45

Leu Pro His Ser Val Ala Glu Gln Leu Lys Arg Gly Glu Thr Val Gln
        50                  55                  60

Ala Glu Ala Phe Asp Ser Val Thr Ile Tyr Phe Ser Asp Ile Val Gly
65                  70                  75                  80

Phe Thr Ala Leu Ser Ala Glu Ser Thr Pro Met Gln Val Val Thr Leu
                85                  90                  95
```

<210> SEQ ID NO 7
<211> LENGTH: 168
<212> TYPE: DNA
<213> ORGANISM: Homo sapiens
<220> FEATURE:
<221> NAME/KEY: CDS
<222> LOCATION: (1)..(168)

<400> SEQUENCE: 7

```
atg agg gag aac agc agc aac atc ctg gac aac ctg ctg tcc cgc atg      48
```

```
Met Arg Glu Asn Ser Ser Asn Ile Leu Asp Asn Leu Ser Arg Met
1               5                   10                  15 gag cag tac gcg aac aat ctg gag gaa ctg gtg gag gag cgg acc cag         96
Glu Gln Tyr Ala Asn Asn Leu Glu Glu Leu Val Glu Glu Arg Thr Gln
                20                  25                  30 gca tac ctg gag gag aag cgc aag gct gag gcc ctg ctc tac cag atc        144
Ala Tyr Leu Glu Glu Lys Arg Lys Ala Glu Ala Leu Leu Tyr Gln Ile
            35                  40                  45 ctg cct cac tca gtg gct gag tga                                        168
Leu Pro His Ser Val Ala Glu
        50                  55
```

<210> SEQ ID NO 8
<211> LENGTH: 55
<212> TYPE: PRT
<213> ORGANISM: Homo sapiens

<400> SEQUENCE: 8

```
Met Arg Glu Asn Ser Ser Asn Ile Leu Asp Asn Leu Ser Arg Met
1               5                   10                  15

Glu Gln Tyr Ala Asn Asn Leu Glu Glu Leu Val Glu Glu Arg Thr Gln
                20                  25                  30

Ala Tyr Leu Glu Glu Lys Arg Lys Ala Glu Ala Leu Leu Tyr Gln Ile
            35                  40                  45

Leu Pro His Ser Val Ala Glu
        50                  55
```

<210> SEQ ID NO 9
<211> LENGTH: 60
<212> TYPE: DNA
<213> ORGANISM: Artificial
<220> FEATURE:
<223> OTHER INFORMATION: primer

<400> SEQUENCE: 9
gggtggatcc accatggact acaaagacga tgacgacaag agggagaaca gcagcaacat        60

<210> SEQ ID NO 10
<211> LENGTH: 29
<212> TYPE: DNA
<213> ORGANISM: Artificial
<220> FEATURE:
<223> OTHER INFORMATION: primer

<400> SEQUENCE: 10
cgggaattct cagcctcggg tgctactcc                                          29

<210> SEQ ID NO 11
<211> LENGTH: 32
<212> TYPE: DNA
<213> ORGANISM: Artificial
<220> FEATURE:
<223> OTHER INFORMATION: primer

<400> SEQUENCE: 11
cgggaattct gacagggtca ccacctgcat gg                                      32

<210> SEQ ID NO 12
<211> LENGTH: 32
<212> TYPE: DNA
<213> ORGANISM: Artificial
<220> FEATURE:
<223> OTHER INFORMATION: primer

<400> SEQUENCE: 12
cgggaattct gactcagcca ctgagtgagg ca                                    32

<210> SEQ ID NO 13
<211> LENGTH: 21
<212> TYPE: DNA
<213> ORGANISM: Artificial
<220> FEATURE:
<223> OTHER INFORMATION: sense strand

<400> SEQUENCE: 13
gaattgaact ttcttccttc t                                                21

<210> SEQ ID NO 14
<211> LENGTH: 21
<212> TYPE: DNA
<213> ORGANISM: Artificial
<220> FEATURE:
<223> OTHER INFORMATION: antisense siRNA

<400> SEQUENCE: 14
ttcttaactt gaaagaagga a                                                21

<210> SEQ ID NO 15
<211> LENGTH: 21
<212> TYPE: DNA
<213> ORGANISM: Artificial
<220> FEATURE:
<223> OTHER INFORMATION: sense strand

<400> SEQUENCE: 15
gaagcttcat acttgacctt g                                                21

<210> SEQ ID NO 16
<211> LENGTH: 21
<212> TYPE: DNA
<213> ORGANISM: Artificial
<220> FEATURE:
<223> OTHER INFORMATION: antisense siRNA

<400> SEQUENCE: 16
gacttcgaag tatgaactgg a                                                21

<210> SEQ ID NO 17
<211> LENGTH: 21
<212> TYPE: DNA
<213> ORGANISM: Artificial
<220> FEATURE:
<223> OTHER INFORMATION: sense strand

<400> SEQUENCE: 17
gtatcctgct atgccctcaa c                                                21

<210> SEQ ID NO 18
<211> LENGTH: 21
<212> TYPE: DNA
<213> ORGANISM: Artificial
<220> FEATURE:
<223> OTHER INFORMATION: antisense siRNA

<400> SEQUENCE: 18
gccataggac gatacgggag t                                                21

<210> SEQ ID NO 19
<211> LENGTH: 21
<212> TYPE: DNA
<213> ORGANISM: Artificial

```
<220> FEATURE:
<223> OTHER INFORMATION: sense strand

<400> SEQUENCE: 19
ctctagagac ctcactgcag t                                              21

<210> SEQ ID NO 20
<211> LENGTH: 21
<212> TYPE: DNA
<213> ORGANISM: Artificial
<220> FEATURE:
<223> OTHER INFORMATION: antisense siRNA

<400> SEQUENCE: 20
cagagatctc tggagtgacg t                                              21

<210> SEQ ID NO 21
<211> LENGTH: 21
<212> TYPE: DNA
<213> ORGANISM: Artificial
<220> FEATURE:
<223> OTHER INFORMATION: sense strand

<400> SEQUENCE: 21
ctagagacct cactgcagtc t                                              21

<210> SEQ ID NO 22
<211> LENGTH: 21
<212> TYPE: DNA
<213> ORGANISM: Artificial
<220> FEATURE:
<223> OTHER INFORMATION: antisense siRNA

<400> SEQUENCE: 22
gagatctctg gagtgacgtc a                                              21

<210> SEQ ID NO 23
<211> LENGTH: 21
<212> TYPE: DNA
<213> ORGANISM: Artificial
<220> FEATURE:
<223> OTHER INFORMATION: sense strand

<400> SEQUENCE: 23
aagcttcata cttgaccttg g                                              21

<210> SEQ ID NO 24
<211> LENGTH: 21
<212> TYPE: DNA
<213> ORGANISM: Artificial
<220> FEATURE:
<223> OTHER INFORMATION: antisense siRNA

<400> SEQUENCE: 24
acttcgaagt atgaactgga a                                              21

<210> SEQ ID NO 25
<211> LENGTH: 21
<212> TYPE: DNA
<213> ORGANISM: Artificial
<220> FEATURE:
<223> OTHER INFORMATION: sense strand

<400> SEQUENCE: 25
tgaactttct tccttctgtt t                                              21
```

```
<210> SEQ ID NO 26
<211> LENGTH: 21
<212> TYPE: DNA
<213> ORGANISM: Artificial
<220> FEATURE:
<223> OTHER INFORMATION: antisense siRNA

<400> SEQUENCE: 26
taacttgaaa gaaggaagac a                                              21

<210> SEQ ID NO 27
<211> LENGTH: 21
<212> TYPE: DNA
<213> ORGANISM: Artificial
<220> FEATURE:
<223> OTHER INFORMATION: sense strand

<400> SEQUENCE: 27
ctgaagcttc atacttgacc t                                              21

<210> SEQ ID NO 28
<211> LENGTH: 20
<212> TYPE: DNA
<213> ORGANISM: Artificial
<220> FEATURE:
<223> OTHER INFORMATION: antisense siRNA

<400> SEQUENCE: 28
agacttcgaa gtatgaactg                                                20

<210> SEQ ID NO 29
<211> LENGTH: 21
<212> TYPE: DNA
<213> ORGANISM: Artificial
<220> FEATURE:
<223> OTHER INFORMATION: sense strand

<400> SEQUENCE: 29
agaattgaac tttcttcctt c                                              21

<210> SEQ ID NO 30
<211> LENGTH: 21
<212> TYPE: DNA
<213> ORGANISM: Artificial
<220> FEATURE:
<223> OTHER INFORMATION: antisense siRNA

<400> SEQUENCE: 30
tttcttaact tgaaagaagg a                                              21

<210> SEQ ID NO 31
<211> LENGTH: 21
<212> TYPE: DNA
<213> ORGANISM: Artificial
<220> FEATURE:
<223> OTHER INFORMATION: sense strand

<400> SEQUENCE: 31
attgaacttt cttccttctg t                                              21

<210> SEQ ID NO 32
<211> LENGTH: 21
<212> TYPE: DNA
<213> ORGANISM: Artificial
<220> FEATURE:
<223> OTHER INFORMATION: antisense siRNA

<400> SEQUENCE: 32
```

```
cttaacttga aagaaggaag a                                              21

<210> SEQ ID NO 33
<211> LENGTH: 20
<212> TYPE: DNA
<213> ORGANISM: Artificial
<220> FEATURE:
<223> OTHER INFORMATION: forward primer to amplify sNRF

<400> SEQUENCE: 33
cctctcttac cacccccacc                                                20

<210> SEQ ID NO 34
<211> LENGTH: 20
<212> TYPE: DNA
<213> ORGANISM: Artificial
<220> FEATURE:
<223> OTHER INFORMATION: reverse primer to amplify sNRF

<400> SEQUENCE: 34
tgcgcttctc ctccaggtat                                                20

<210> SEQ ID NO 35
<211> LENGTH: 195
<212> TYPE: DNA
<213> ORGANISM: Artificial
<220> FEATURE:
<223> OTHER INFORMATION: Northern probe for intron 15 of NPRA

<400> SEQUENCE: 35
tctgaagctt catacttgac cttggggtct cagaaaagaa ttgaactttc ttccttctgt    60
tttcccctgc tccccggtat cctgctatgc cctcaaccct gagcgtctct agagacctca   120
ctgcagtctg aggggaag tgcctagggg cgggcgctca cggtaggctg tgctgctcct    180
ctcttaccac cccca                                                   195

<210> SEQ ID NO 36
<211> LENGTH: 23
<212> TYPE: DNA
<213> ORGANISM: Artificial
<220> FEATURE:
<223> OTHER INFORMATION: TaqMan Probe for quantitation of sNRF RNA.

<400> SEQUENCE: 36
cctctgcccc cagggagaac agc                                            23

<210> SEQ ID NO 37
<211> LENGTH: 816
<212> TYPE: DNA
<213> ORGANISM: Homo sapiens
<220> FEATURE:
<221> NAME/KEY: CDS
<222> LOCATION: (256)..(816)

<400> SEQUENCE: 37
tctgaagctt catacttgac cttggggtct cagaaaagaa ttgaactttc ttccttctgt    60
tttcccctgc tccccggtat cctgctatgc cctcaaccct gagcgtctct agagacctca   120
ctgcagtctg aggggaag tgcctagggg cgggcgctca cggtaggctg tgctgctcct    180
ctcttaccac ccccaccgcc accctctgcc cccagggaga acagcagcaa catcctggac   240
aacctgctgt cccgc atg gag cag tac gcg aac aat ctg gag gaa ctg gtg    291
                Met Glu Gln Tyr Ala Asn Asn Leu Glu Glu Leu Val
                 1               5                  10
```

```
gag gag cgg acc cag gca tac ctg gag gag aag cgc aag gct gag gcc      339
Glu Glu Arg Thr Gln Ala Tyr Leu Glu Glu Lys Arg Lys Ala Glu Ala
        15                  20                  25 ctg ctc tac cag atc ctg cct cac tca gtg gct gag cag ctg aag cgt      387
Leu Leu Tyr Gln Ile Leu Pro His Ser Val Ala Glu Gln Leu Lys Arg
    30                  35                  40 ggg gag acg gtg cag gcc gaa gcc ttt gac agt gtt acc atc tac ttc      435
Gly Glu Thr Val Gln Ala Glu Ala Phe Asp Ser Val Thr Ile Tyr Phe
45                  50                  55                  60 agt gac att gtg ggt ttc aca gcg ctg tcg gcg gag agc aca ccc atg      483
Ser Asp Ile Val Gly Phe Thr Ala Leu Ser Ala Glu Ser Thr Pro Met
                65                  70                  75 cag gtg gtg acc ctg ctc aat gac ctg tac act tgc ttt gat gct gtc      531
Gln Val Val Thr Leu Leu Asn Asp Leu Tyr Thr Cys Phe Asp Ala Val
            80                  85                  90 ata gac aac ttt gat gtg tac aag gtg gag aca att ggc gat gcc tac      579
Ile Asp Asn Phe Asp Val Tyr Lys Val Glu Thr Ile Gly Asp Ala Tyr
        95                 100                 105 atg gtg gtg tca ggg ctc cct gtg cgg aac ggg cgg cta cac gcc tgc      627
Met Val Val Ser Gly Leu Pro Val Arg Asn Gly Arg Leu His Ala Cys
    110                 115                 120 gag gta gcc cgc atg gcc ctg gca ctg ctg gat gct gtg cgc tcc ttc      675
Glu Val Ala Arg Met Ala Leu Ala Leu Leu Asp Ala Val Arg Ser Phe
125                 130                 135                 140 cga atc cgc cac cgg ccc cag gag cag ctg cgc ttg cgc att ggc atc      723
Arg Ile Arg His Arg Pro Gln Glu Gln Leu Arg Leu Arg Ile Gly Ile
                145                 150                 155 cac aca gga cct gtg tgt gct gga gtg gtg gga ctg aag atg ccc cgt      771
His Thr Gly Pro Val Cys Ala Gly Val Val Gly Leu Lys Met Pro Arg
            160                 165                 170 tac tgt ctc ttt ggg gat aca gtc aac aca gcc tca aga atg gag           816
Tyr Cys Leu Phe Gly Asp Thr Val Asn Thr Ala Ser Arg Met Glu
        175                 180                 185

<210> SEQ ID NO 38
<211> LENGTH: 187
<212> TYPE: PRT
<213> ORGANISM: Homo sapiens

<400> SEQUENCE: 38

Met Glu Gln Tyr Ala Asn Asn Leu Glu Glu Leu Val Glu Glu Arg Thr
1               5                   10                  15

Gln Ala Tyr Leu Glu Glu Lys Arg Lys Ala Glu Ala Leu Leu Tyr Gln
            20                  25                  30

Ile Leu Pro His Ser Val Ala Glu Gln Leu Lys Arg Gly Glu Thr Val
        35                  40                  45

Gln Ala Glu Ala Phe Asp Ser Val Thr Ile Tyr Phe Ser Asp Ile Val
    50                  55                  60

Gly Phe Thr Ala Leu Ser Ala Glu Ser Thr Pro Met Gln Val Val Thr
65                  70                  75                  80

Leu Leu Asn Asp Leu Tyr Thr Cys Phe Asp Ala Val Ile Asp Asn Phe
                85                  90                  95

Asp Val Tyr Lys Val Glu Thr Ile Gly Asp Ala Tyr Met Val Val Ser
            100                 105                 110

Gly Leu Pro Val Arg Asn Gly Arg Leu His Ala Cys Glu Val Ala Arg
        115                 120                 125

Met Ala Leu Ala Leu Leu Asp Ala Val Arg Ser Phe Arg Ile Arg His
    130                 135                 140

Arg Pro Gln Glu Gln Leu Arg Leu Arg Ile Gly Ile His Thr Gly Pro
```

```
             145                 150                 155                 160
Val Cys Ala Gly Val Val Gly Leu Lys Met Pro Arg Tyr Cys Leu Phe
                165                 170                 175

Gly Asp Thr Val Asn Thr Ala Ser Arg Met Glu
                180                 185

<210> SEQ ID NO 39
<211> LENGTH: 729
<212> TYPE: DNA
<213> ORGANISM: Homo sapiens
<220> FEATURE:
<221> NAME/KEY: CDS
<222> LOCATION: (1)..(726)

<400> SEQUENCE: 39 atg gag cag tac gcg aac aat ctg gag gaa ctg gtg gag gag cgg acc       48
Met Glu Gln Tyr Ala Asn Asn Leu Glu Glu Leu Val Glu Glu Arg Thr
1               5                   10                  15 cag gca tac ctg gag gag aag cgc aag gct gag gcc ctg ctc tac cag       96
Gln Ala Tyr Leu Glu Glu Lys Arg Lys Ala Glu Ala Leu Leu Tyr Gln
            20                  25                  30 atc ctg cct cac tca gtg gct gag cag ctg aag cgt ggg gag acg gtg      144
Ile Leu Pro His Ser Val Ala Glu Gln Leu Lys Arg Gly Glu Thr Val
        35                  40                  45 cag gcc gaa gcc ttt gac agt gtt acc atc tac ttc agt gac att gtg      192
Gln Ala Glu Ala Phe Asp Ser Val Thr Ile Tyr Phe Ser Asp Ile Val
    50                  55                  60 ggt ttc aca gcg ctg tcg gcg gag agc acg ccc atg cag gtg gtg acc      240
Gly Phe Thr Ala Leu Ser Ala Glu Ser Thr Pro Met Gln Val Val Thr
65                  70                  75                  80 ctg ctc aat gac ctg tac act tgc ttt gat gct gtc ata gac aac ttt      288
Leu Leu Asn Asp Leu Tyr Thr Cys Phe Asp Ala Val Ile Asp Asn Phe
                85                  90                  95 gat gtg tac aag gtg gag aca att ggc gat gcc tac atg gtg gtg tca      336
Asp Val Tyr Lys Val Glu Thr Ile Gly Asp Ala Tyr Met Val Val Ser
            100                 105                 110 ggg ctc cct gtg cgg aac ggg cgg cta cac gcc tgc gag gta gcc cgc      384
Gly Leu Pro Val Arg Asn Gly Arg Leu His Ala Cys Glu Val Ala Arg
        115                 120                 125 atg gcc ctg gca ctg ctg gat gct gtg cgc tcc ttc cga atc cgc cac      432
Met Ala Leu Ala Leu Leu Asp Ala Val Arg Ser Phe Arg Ile Arg His
    130                 135                 140 cgg ccc cag gag cag ctg cgc ttg cgc att ggc atc cac aca gga cct      480
Arg Pro Gln Glu Gln Leu Arg Leu Arg Ile Gly Ile His Thr Gly Pro
145                 150                 155                 160 gtg tgt gct gga gtg gtg gga ctg aag atg ccc cgt tac tgt ctc ttt      528
Val Cys Ala Gly Val Val Gly Leu Lys Met Pro Arg Tyr Cys Leu Phe
                165                 170                 175 ggg gat aca gtc aac aca gcc tca aga atg gag tct aat ggg gaa gcc      576
Gly Asp Thr Val Asn Thr Ala Ser Arg Met Glu Ser Asn Gly Glu Ala
            180                 185                 190 ctg aag atc cac ttg tct tct gag acc aag gct gtc ctg gag gag ttt      624
Leu Lys Ile His Leu Ser Ser Glu Thr Lys Ala Val Leu Glu Glu Phe
        195                 200                 205 ggt ggt ttc gag ctg gag ctt cga ggg gat gta gaa atg aag ggc aaa      672
Gly Gly Phe Glu Leu Glu Leu Arg Gly Asp Val Glu Met Lys Gly Lys
    210                 215                 220 ggc aag gtt cgg acc tac tgg ctc ctt ggg gag agg ggg agt agc acc      720
Gly Lys Val Arg Thr Tyr Trp Leu Leu Gly Glu Arg Gly Ser Ser Thr
225                 230                 235                 240 cga ggc tga                                                          729
```

Arg Gly

<210> SEQ ID NO 40
<211> LENGTH: 242
<212> TYPE: PRT
<213> ORGANISM: Homo sapiens

<400> SEQUENCE: 40

Met Glu Gln Tyr Ala Asn Asn Leu Glu Glu Leu Val Glu Glu Arg Thr
1               5                   10                  15

Gln Ala Tyr Leu Glu Glu Lys Arg Lys Ala Glu Ala Leu Leu Tyr Gln
            20                  25                  30

Ile Leu Pro His Ser Val Ala Glu Gln Leu Lys Arg Gly Glu Thr Val
        35                  40                  45

Gln Ala Glu Ala Phe Asp Ser Val Thr Ile Tyr Phe Ser Asp Ile Val
    50                  55                  60

Gly Phe Thr Ala Leu Ser Ala Glu Ser Thr Pro Met Gln Val Val Thr
65                  70                  75                  80

Leu Leu Asn Asp Leu Tyr Thr Cys Phe Asp Ala Val Ile Asp Asn Phe
                85                  90                  95

Asp Val Tyr Lys Val Glu Thr Ile Gly Asp Ala Tyr Met Val Val Ser
            100                 105                 110

Gly Leu Pro Val Arg Asn Gly Arg Leu His Ala Cys Glu Val Ala Arg
        115                 120                 125

Met Ala Leu Ala Leu Leu Asp Ala Val Arg Ser Phe Arg Ile Arg His
    130                 135                 140

Arg Pro Gln Glu Gln Leu Arg Leu Arg Ile Gly Ile His Thr Gly Pro
145                 150                 155                 160

Val Cys Ala Gly Val Val Gly Leu Lys Met Pro Arg Tyr Cys Leu Phe
                165                 170                 175

Gly Asp Thr Val Asn Thr Ala Ser Arg Met Glu Ser Asn Gly Glu Ala
            180                 185                 190

Leu Lys Ile His Leu Ser Ser Glu Thr Lys Ala Val Leu Glu Glu Phe
        195                 200                 205

Gly Gly Phe Glu Leu Glu Leu Arg Gly Asp Val Glu Met Lys Gly Lys
    210                 215                 220

Gly Lys Val Arg Thr Tyr Trp Leu Leu Gly Glu Arg Gly Ser Ser Thr
225                 230                 235                 240

Arg Gly

<210> SEQ ID NO 41
<211> LENGTH: 243
<212> TYPE: DNA
<213> ORGANISM: Homo sapiens
<220> FEATURE:
<221> NAME/KEY: CDS
<222> LOCATION: (1)..(243)

<400> SEQUENCE: 41 atg gag cag tac gcg aac aat ctg gag gaa ctg gtg gag gag cgg acc     48
Met Glu Gln Tyr Ala Asn Asn Leu Glu Glu Leu Val Glu Glu Arg Thr
1               5                   10                  15 cag gca tac ctg gag gag aag cgc aag gct gag gcc ctg ctc tac cag    96
Gln Ala Tyr Leu Glu Glu Lys Arg Lys Ala Glu Ala Leu Leu Tyr Gln
            20                  25                  30 atc ctg cct cac tca gtg gct gag cag ctg aag cgt ggg gag acg gtg   144
Ile Leu Pro His Ser Val Ala Glu Gln Leu Lys Arg Gly Glu Thr Val
        35                  40                  45

-continued

```
cag gcc gaa gcc ttt gac agt gtt acc atc tac ttc agt gac att gtg    192
Gln Ala Glu Ala Phe Asp Ser Val Thr Ile Tyr Phe Ser Asp Ile Val
     50                  55                  60 ggt ttc aca gcg ctg tcg gcg gag agc acg ccc atg cag gtg gtg acc    240
Gly Phe Thr Ala Leu Ser Ala Glu Ser Thr Pro Met Gln Val Val Thr
 65                  70                  75                  80 ctg                                                                 243
Leu
```

<210> SEQ ID NO 42
<211> LENGTH: 81
<212> TYPE: PRT
<213> ORGANISM: Homo sapiens

<400> SEQUENCE: 42

```
Met Glu Gln Tyr Ala Asn Asn Leu Glu Glu Leu Val Glu Glu Arg Thr
 1               5                  10                  15

Gln Ala Tyr Leu Glu Glu Lys Arg Lys Ala Glu Ala Leu Leu Tyr Gln
            20                  25                  30

Ile Leu Pro His Ser Val Ala Glu Gln Leu Lys Arg Gly Glu Thr Val
        35                  40                  45

Gln Ala Glu Ala Phe Asp Ser Val Thr Ile Tyr Phe Ser Asp Ile Val
    50                  55                  60

Gly Phe Thr Ala Leu Ser Ala Glu Ser Thr Pro Met Gln Val Val Thr
 65                  70                  75                  80

Leu
```

<210> SEQ ID NO 43
<211> LENGTH: 20
<212> TYPE: DNA
<213> ORGANISM: Artificial
<220> FEATURE:
<223> OTHER INFORMATION: forward primer to amplify sNRF

<400> SEQUENCE: 43
ttgaactttc ttccttctgt                                              20

<210> SEQ ID NO 44
<211> LENGTH: 20
<212> TYPE: DNA
<213> ORGANISM: Artificial
<220> FEATURE:
<223> OTHER INFORMATION: reverse primer to amplify sNRF

<400> SEQUENCE: 44
agatggtaac actgtcaaag                                              20